United States Patent
Tolia et al.

(10) Patent No.: US 10,273,468 B2
(45) Date of Patent: Apr. 30, 2019

(54) INHIBITION AND DIAGNOSTICS OF EMERGING TETRACYCLINE RESISTANCE ENZYMES

(71) Applicants: Niraj Tolia, St. Louis, MO (US); Gautam Dantas, St. Louis, MO (US); Timothy Wencewicz, St. Louis, MO (US); Jooyoung Park, St. Louis, MO (US); Andrew Gasparrini, St. Louis, MO (US); Kevin Forsberg, St. Louis, MO (US); Joseph Vogel, St. Louis, MO (US); Margaret Ruth Reck, St. Louis, MO (US); Chanez Tiffany Symister, St. Louis, MO (US); Jana L. Markley, St. Louis, MO (US)

(72) Inventors: Niraj Tolia, St. Louis, MO (US); Gautam Dantas, St. Louis, MO (US); Timothy Wencewicz, St. Louis, MO (US); Jooyoung Park, St. Louis, MO (US); Andrew Gasparrini, St. Louis, MO (US); Kevin Forsberg, St. Louis, MO (US); Joseph Vogel, St. Louis, MO (US); Margaret Ruth Reck, St. Louis, MO (US); Chanez Tiffany Symister, St. Louis, MO (US); Jana L. Markley, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/633,254

(22) Filed: Jun. 26, 2017

(65) Prior Publication Data
US 2017/0369864 A1 Dec. 28, 2017

Related U.S. Application Data

(60) Provisional application No. 62/354,404, filed on Jun. 24, 2016.

(51) Int. Cl.
| | |
|---|---|
| *C12N 9/99* | (2006.01) |
| *C12Q 1/04* | (2006.01) |
| *A61K 39/40* | (2006.01) |
| *A61K 38/00* | (2006.01) |
| *A61K 31/65* | (2006.01) |
| *A61K 47/00* | (2006.01) |
| *C12N 9/00* | (2006.01) |
| *A61K 47/68* | (2017.01) |

(52) U.S. Cl.
CPC .............. *C12N 9/99* (2013.01); *A61K 31/65* (2013.01); *A61K 38/005* (2013.01); *A61K 39/40* (2013.01); *A61K 47/6809* (2017.08); *C12Q 1/04* (2013.01); *A61K 47/00* (2013.01); *C12N 9/00* (2013.01); *Y02A 50/478* (2018.01)

(58) Field of Classification Search
CPC ...... C12N 9/99; A61K 31/65; A61K 47/6809; A61K 38/005; A61K 39/40; C12Q 1/04
USPC ........................................................ 514/152
See application file for complete search history.

(56) References Cited

FOREIGN PATENT DOCUMENTS

WO WO 2014118361 A1 * 8/2014 ............. A61K 31/16

OTHER PUBLICATIONS

Sengelov et al. Veterinary Microbiology, (2013), 95, p. 91-101.*
Adams, P. et al., "PHENIX: a comprehensive Python-based system for macromolecular structure solution," Acta Crystallogr. D, Biol. Crystallogr., 2010, pp. 213-221, vol. D66.
Allen, H. et al., "Call of the wild: antibiotic resistance genes in natural environments," Nat. Rev. Microbiol., 2010, pp. 251-259, vol. 8, Advance Online Publication, pp. 1-9, Macmillan Publishers Limited.
Ballou, D. et al., "Dynamics involved in catalysis by singlecomponent and two-component flavin-dependent aromatic hydroxylases," Biochem. Biophys. Res. Commun., 2005, pp. 590-598, vol. 338.
Benveniste, R. et al., "Aminoglycoside Antibiotic-Inactivating Enzymes in Actinomycetes Similar to Those Present in Clinical Isolates of Antibiotic-Resistant Bacteria," PNAS, Aug. 1973, pp. 2276-2280, vol. 70, No. 8.
Berenbaum, M., "A Method for Testing for Synergy with Any Number of Agents," J. Infect. Dis., Feb. 1978, pp. 122-130, vol. 137, No. 2, Oxford University Press.
Berendonk, T. et al., "Tackling antibiotic resistance: the environmental framework," Nat. Rev. Microbiol., Apr. 2015, pp. 310-317, vol. 13, Macmillan Publishers Limited.
Berger, K. et al., "Two distinct defects in intracellular growth complemented by a single genetic locus in Legionella pneumophila," Mol. Microbiol., 1993, pp. 7-19, vol. 7, No. 1.
Boucher, H. et al., "Bad bugs, no drugs: no ESKAPE! An update from the Infectious Diseases Society of America," Clin. Infect. Dis., Jan. 1, 2009, pp. 1-12, vol. 48.
Cazalet, C. et al., "Analysis of the Legionella longbeachae Genome and Transcriptome Uncovers Unique Strategies to Cause Legionnaires' Disease," PLoS Genet, Feb. 2010, pp. 1-16, vol. 6, No. 2, e1000851.

(Continued)

Primary Examiner — Yong L Chu
(74) Attorney, Agent, or Firm — Polsinelli PC

(57) ABSTRACT

The present disclosure provides compositions and methods for treating bacterial infections in a subject. The methods comprise administering a compound that binds a FAD-dependent flavoenzyme and a tetracycline, analog, derivative, or pharmaceutically acceptable salt thereof.

6 Claims, 36 Drawing Sheets
(26 of 36 Drawing Sheet(s) Filed in Color)
Specification includes a Sequence Listing.

(56) References Cited

OTHER PUBLICATIONS

Chen, V. et al., "MolProbity: all-atom structure validation for macromolecular crystallography," Acta Crystallogr. D Biol. Crystallogr., 2010, pp. 12-21, vol. D66.

Chopra, I. et al., "Tetracycline antibiotics: mode of action, applications, molecular biology, and epidemiology of bacterial resistance," Microbial Mol Biol Rev, Jun. 2001, pp. 232-260, vol. 65, No. 2, American Society for Microbiology.

Davies, J., "Inactivation of Antibiotics and the Dissemination of Resistance Genes," Sci., Apr. 15, 1994, pp. 375-382, vol. 264.

D'Costa, V. et al., "Antibiotic resistance is ancient," Nature, 2011, pp. 457-461, vol. 477.

Deng, M. et al., "Molecular Epidemiology and Mechanisms of Tigecycline Resistance in Clinical Isolates of Acinetobacter baumannii from a Chinese University Hospital," Antimicrob. Agents Chemother., Jan. 2014, pp. 297-303, vol. 58, No. 1.

Diaz-Torres, M. et al., "Novel Tetracycline Resistance Determinant from the Oral Metagenome," Antimicrob. Agents Chemother., Apr. 2003, pp. 1430-1432, vol. 47, No. 4, American Society for Microbiology.

Drawz, S. et al., "New beta-Lactamase Inhibitors: a Therapeutic Renaissance in an MDR World," Antimicrob. Agents Chemother., Apr. 2014, pp. 1835-1846, vol. 58, No. 4, American Society for Microbiology.

Emsley, R et al., "Coot: model-building tools for molecular graphics," Acta Crystallogr. D Biol. Crystallogr., 2004, pp. 2126-2132, vol. D60.

Feeley, J. et al., "Charcoal-Yeast Extract Agar: Primary Isolation Medium for Legionella pneumophila," J. Clin. Microbiol., Oct. 1979, pp. 437-441, vol. 10, No. 4.

Forsberg, K. et al., "Bacterial phylogeny structures soil resistomes across habitats," Nature, May 29, 2014, pp. 612-616, vol. 509, with Methods, 13 pgs.

Forsberg, K. et al., "The shared antibiotic resistome of soil bacteria and human pathogens," NIH Public Access Author Manuscript, available in PMC Jun. 25, 2014; published in final edited form as: Sci., Aug. 31, 2012, pp. 1107-1111, vol. 337, No. 6098.

Forsberg, K. et al., "The Tetracycline Destructases: A Novel Family of Tetracycline-Inactivating Enzymes," Chemistry & Biology, Jul. 23, 2015, pp. 888-897, vol. 22, Elsevier Ltd.

Gatti, D. et al., "The Mobile Flavin of 4-OH Benzoate Hydroxylase," Sci., Oct. 7, 1994, pp. 110-114, vol. 266, No. 5182, American Society for the Advancement of Science.

Gelband, H. et al., "The State of the World's Antibiotics 2015," Center for Disease Dynamics, Economics & Policy, 2015, pp. 1-79.

Ghosh, S. et al., "*Sphingobacterium* sp. strain PM2-P1-29 harbours a functional tet(X) gene encoding for the degradation of tetracycline," J. Appl. Microbiol., 2009, pp. 1336-1342, vol. 106.

Gibson, M. et al., "Characterization of Kinetics and Products of the Baeyer-Villiger Oxygenase MtmOIV, the Key Enzyme of the Biosynthetic Pathway toward the Natural Product Anticancer Drug Mithramycin from Streptomyces argillaceus," J. Am. Chem. Soc., 2005, pp. 17594-17595, vol. 127, No. 50.

Hornak, V. et al., "HIV-1 protease flaps spontaneously close to the correct structure in simulations following manual placement of an inhibitor into the open state," NIH Public Access Author Manuscript, available in PMC Sep. 29, 2008; published in final edited form as: J Am Chem Soc, Mar. 8, 2006, pp. 2812-2813, vol. 128, No. 9.

Kabsch, W., "XDS," Acta Crystallogr. D Biol. Crystallogr., Feb. 1, 2010, pp. 125-132, vol. D66, Part 2.

Kasbekar, N., "Tigecycline: A new glycylcycline antimicrobial agent," Am. J. Health-Syst. Pharm., Jul. 1, 2006, pp. 1235-1243, vol. 63.

Kinch, M. et al., "An analysis of FDA-approved drugs for infectious disease: antibacterial agents," Drug Discov. Today, Sep. 2014, pp. 1283-1287, vol. 19, No. 9.

Knapp, C. et al., "Evidence of Increasing Antibiotic Resistance Gene Abundances in Archived Soils since 1940," Environ. Sci. Technol., 2010, pp. 580-587, vol. 44, No. 2.

Leski, T. et al., "Multidrug-resistant tet(X)-containing hospital isolates in Sierra Leone," Int. J. Antimicrob. Agents, 2013, pp. 83-86, vol. 42, Elsevier B.V. on behalf of International Society of Chemotherapy.

Lienhart, W. et al., "The human flavoproteome," Arch. Biochem. .Biophys., 2013, pp. 150-162, vol. 535.

Liu, F. et al., "Development of a platform for the discovery and practical synthesis of new tetracycline antibiotics," Curr. Opin. Chem. Biol., 2016, pp. 48-57, vol. 32.

Liu, L. et al., "The Structure of the Antibiotic Deactivating, N-hydroxylating Rifampicin Monooxygenase," J. Biol. Chem., Oct. 7, 2016, pp. 21553-21562, vol. 291, No. 41.

Liu, Y. et al., "Emergence of plasmid-mediated colistin resistance mechanism MCR-1 in animals and human beings in China: a microbiological and molecular biological study," Lancet Infect. Dis., Feb. 2016, pp. 161-168, vol. 16.

Macone, A. et al., "The In Vitro and In Vivo Antibacterial Activities of Omadacycline, a Novel Aminomethylcycline," Antimicrob Agents Chemother, Feb. 2014, pp. 1127-1135, vol. 58, No. 2.

Massey, V., "Activation of Molecular Oxygen by Flavins and Flavoproteins," J. Biol. Chem., Sep. 9, 1994, pp. 22459-22462, vol. 269, No. 36.

Merriam, J. et al., "Analysis of the Legionella pneumophila flil Gene: Intracellular Growth of a Defined Mutant Defective for Flagellum Biosynthesis," Infect. Immun., Jun. 1997, pp. 2497-2501, vol. 65, No. 6, American Society for Microbiology.

Moore, I. et al., "Tigecycline Is Modified by the Flavin-Dependent Monooxygenase TetX," Biochem., 2005, pp. 11829-11835, vol. 44, No. 35.

Nonaka, L. et al., "New Mg2+-Dependent Oxytetracycline Resistance Determinant Tet 34 in Vibrio Isolates from Marine Fish Intestinal Contents," Antimicrob. Agents Chemother., May 2002, pp. 1550-1552, vol. 46, No. 5.

Palmer, A. et al., "Chemical decay of an antibiotic inverts selection for resistance," Nat. Chem. Biol., Feb. 2010, pp. 105-107, vol. 6, with Corrigendum, 1 pg., Nature America, Inc.

Park, B. et al., "The Cryptic Tetracycline Resistance Determinant on Tn4400 Mediates Tetracycline Degradation as well as Tetracycline Efflux," Antimicrob. Agents Chemother., Dec. 1988, pp. 1797-1800, vol. 32, No. 12, American Society for Microbiology.

Patel, J. et al., "Methods for Dilution Antimicrobial Susceptibility Testing for Bacteria That Grow Aerobically; Approved Standard—Tenth Edition," Clinical and Laboratory Standards Institute, M07-A10, Jan. 2015, pp. 1-92, vol. 35, No. 2.

Pesnot, T. et al., "Structural and mechanistic basis for a new mode of glycosyltransferase inhibition," Europe PMC Funders Group, Author Manuscript, available in PMC Nov. 1, 2010, pp. 1-11, published in final form as: Nat. Chem. Biol., May 2010, pp. 321-323, vol. 6, No. 5.

Poirel, L. et al., "Origin of Plasmid-Mediated Quinolone Resistance Determinant QnrA," Antimicrob. Agents Chemother., Aug. 2005, pp. 3523-3525, vol. 49, No. 8.

Sexton, J. et al., "The Legionella pneumophila PilT Homologue DotB Exhibits ATPase Activity That Is Critical for Intracellular Growth," J. Bacteriol., Mar. 2004, pp. 1658-1666, vol. 186, No. 6, American Society for Microbiology.

Speer, B. et al., "Characterization of a Novel Tetracycline Resistance That Functions Only in Aerobically Grown *Escherichia coli*," J. .Bacteriol, Apr. 1988, pp. 1423-1429, vol. 170, No. 4, American Society for Microbiology.

Sutcliffe, J.et al., "Antibacterial activity of eravacycline (TP-434), a novel fluorocycline, against hospital and community pathogens," Antimicrob Agents Chemother, 2013, pp. 5548-5558, vol. 57, published online ahead of print on Aug. 26, 2013.

Thaker, M. et al., "The tetracycline resistome," Cell Mol. Life Sci., 2010, pp. 419-431, vol. 67, Birkhauser Verlag, Basel, Switzerland.

Van Berkel, W. et al., "Flavoprotein monooxygenases, a diverse class of oxidative biocatalysts," J. Biotechnol., 2006, pp. 670-689, vol. 124, Elsevier B.V.

Volkers, G. et al., "Putative dioxygen-binding sites and recognition of tigecycline and minocycline in the tetracycline-Degrading

(56) References Cited

OTHER PUBLICATIONS monooxygenase TetX," Acta Crystallogr. D Biol. Crystallogr., 2013, pp. 1758-1767, vol. D69, International Union of Crystallography.

Volkers, G. et al., "Structural basis for a new tetracycline resistance mechanism relying on the TetX monooxygenase," FEBS Lett., 2011, pp. 1061-1066, vol. 585, Elsevier B.V. on behalf of Federation of European Biochemical Societies.

Walsh, C. et al., "Flavoenzymes: versatile catalysts in biosynthetic pathways," NIH Public Access Author Manuscript, available in PMC Jan. 1, 2014, pp. 1-53; published in final edited form as: Nat. Prod. Rep., Jan. 2013, pp. 175-200, vol. 30, No. 1.

Wang, P. et al., "Uncovering the Enzymes that Catalyze the Final Steps in Oxytetracycline Biosynthesis," J. Am. Chem. Soc., 2013, pp. 7138-7141, vol. 135.

Whiley, H. et al., "Legionella longbeachae and legionellosis," Emerg. Infect. Dis., Apr. 2011, pp. 579-583, vol. 17, No. 4.

Whittle, G. et al., "Characterization of the 13-kilobase ermF region of the Bacteroides conjugative transposon CTnDOT," Appl. Environ. Microbiol., Aug. 2001, pp. 3488-3495, vol. 67, No. 8, American Society for Microbiology.

Winn, M. et al., "Overview of the CCP4 suite and current developments," Acta Crystallogr. D Biol. Crystallogr., 2011, pp. 235-242, vol. D67.

Yang, W. et al., "TetX Is a Flavin-dependent Monooxygenase Conferring Resistance to Tetracycline Antibiotics," J. Biol. Chem., Dec. 10, 2004, pp. 52346-52352, vol. 279, No. 50, The American Society for Biochemistry and Molecular Biology, Inc.

Yong, D. et al., "Characterization of a new metallo-beta-lactamase gene, bla(NDM1), and a novel erythromycin esterase gene carried on a unique genetic structure in Klebsiella pneumoniae sequence type 14 from India," Antimicrob. Agents Chemother., Dec. 2009, pp. 5046-5054, vol. 53, No. 12, American Society for Microbiology.

Yuen, P. et al., "Kinetics of Concomitant Degradation of Tetracycline to Epitetracycline, Anhydrotetracycline, and Epianhydrotetracycline in Acid Phosphate Solution," J. Pharm. Sci., Nov. 1977, pp. 1648-1650, vol. 66, No. 11.

* cited by examiner

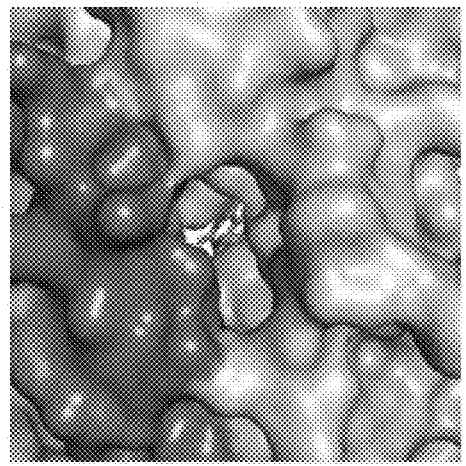 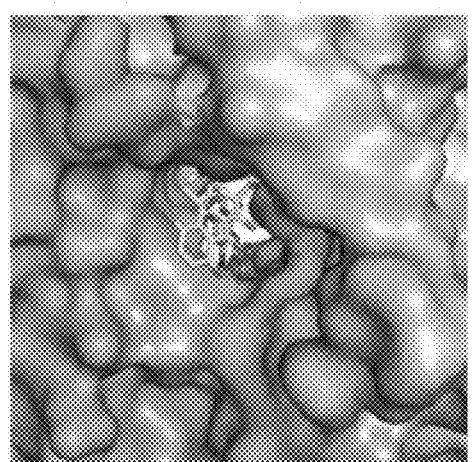
FIG. 2F     FIG. 2G

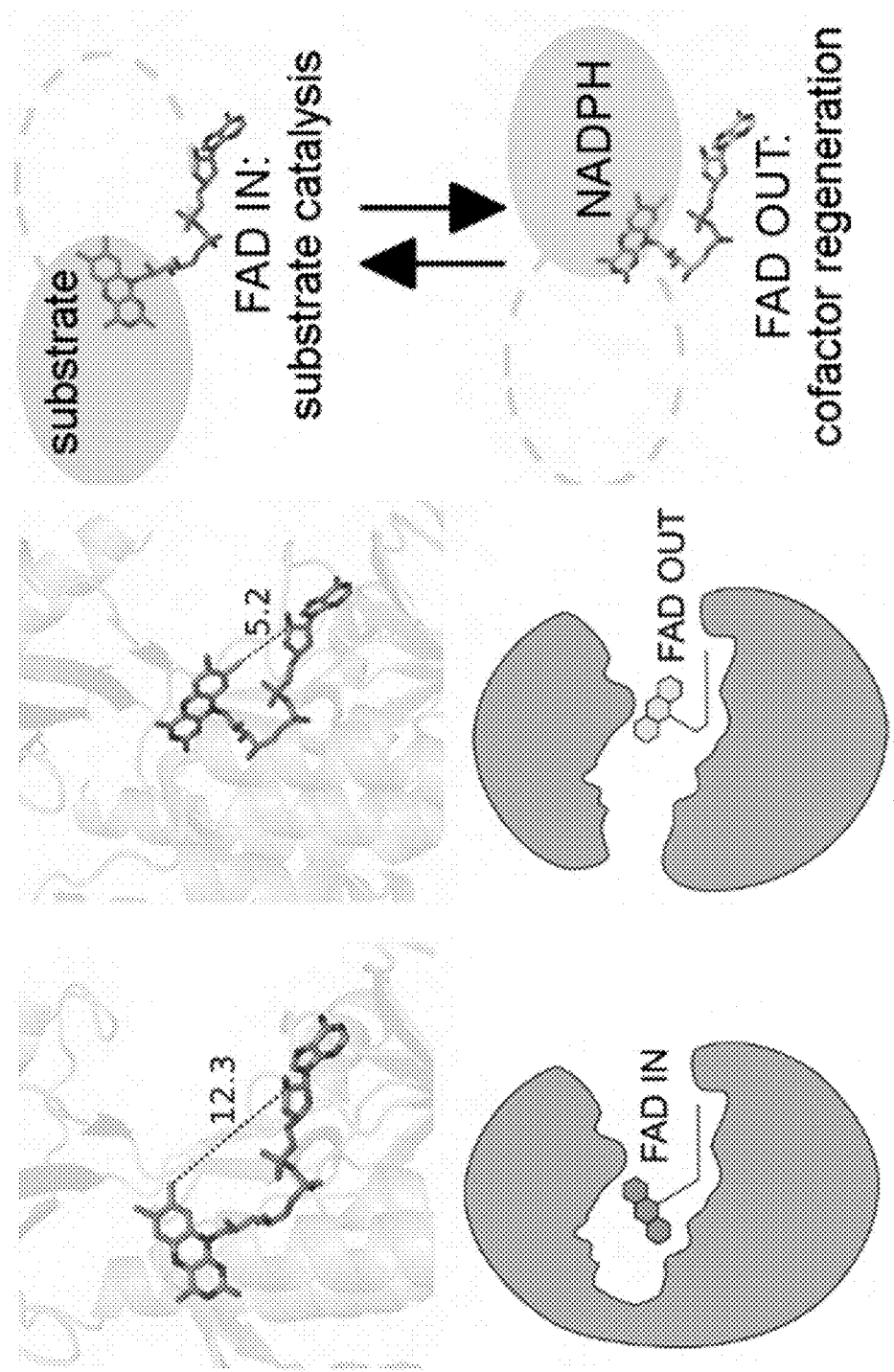

FIG. 11A  FIG. 11B

```
                      SEQUENCE LISTING

<160> NUMBER OF SEQ ID NOS: 10

<210> SEQ ID NO 1
   <211> LENGTH: 39
   <212> TYPE: DNA
   <213> ORGANISM: Artificial Sequence
   <220> FEATURE:
   <223> OTHER INFORMATION: SYNTHESIZED

<400> SEQUENCE: 1
gcagtcgacg ctcaattgta tgttcgttat gaagatggg                              39

<210> SEQ ID NO 2
   <211> LENGTH: 42
   <212> TYPE: DNA
   <213> ORGANISM: Artificial Sequence
   <220> FEATURE:
   <223> OTHER INFORMATION: SYNTHESIZED

<400> SEQUENCE: 2
gcagcggccg cgccaatgac gagaattttg atatttttag ac                         42

<210> SEQ ID NO 3
   <211> LENGTH: 38
   <212> TYPE: DNA
   <213> ORGANISM: Artificial Sequence
   <220> FEATURE:
   <223> OTHER INFORMATION: SYNTHESIZED

<400> SEQUENCE: 3
gcagcggccg ccaatttcga atgggattac cttacctc                              38

<210> SEQ ID NO 4
   <211> LENGTH: 44
   <212> TYPE: DNA
   <213> ORGANISM: Artificial Sequence
   <220> FEATURE:
   <223> OTHER INFORMATION: SYNTHESIZED

<400> SEQUENCE: 4
gcagagctcg cttaatgata tcaagattaa tacaattcca atcc                       44

<210> SEQ ID NO 5
   <211> LENGTH: 54
   <212> TYPE: DNA
   <213> ORGANISM: Artificial Sequence
   <220> FEATURE:
   <223> OTHER INFORMATION: SYNTHESIZED
```

```
<400> SEQUENCE: 5
ccaggatcct aagaggagaa attaactatg tctaaaaata tcaaaattct cgtc         54

<210> SEQ ID NO 6
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 6
ccagtcgacg tccactatga tgattcatat tgagg                             35

<210> SEQ ID NO 7
<211> LENGTH: 6585
<212> TYPE: DNA
<213> ORGANISM: Artificial Sequence
<220> FEATURE:
<223> OTHER INFORMATION: SYNTHESIZED

<400> SEQUENCE: 7
gtcgacggta tcgataagct tgatatcgaa ttcctgcagc ccgggggatc cactagttct   60
agagcggccg ccaccgcggt ggagctccag cttttgttcc ctttagtgag ggttaatttc  120
gagcttggcg taatcatggt catagctgtt tcctgtgtga attgttatc cgctcacaat  180
tccacacaac atacgagccg gaagcataaa gtgtaaagcc tggggtgcct aatgagtgag  240
ctaactcaca ttaattgcgt tgcgctcact gcccgctttc cagtcgggaa acctgtcgtg  300
ccagctgcat taatgaatcg gccaacgcta caattcccat gtcagccgtt aagtgttcct  360
gtgtcactca aaattgcttt gagaggctct aagggcttct cagtgcgtta catccctggc  420
ttgttgtcca accgttaa accttaaaag ctttaaaagc cttatatatt cttttttttc   480
ttataaaact taaaaccttg gaggctattt aagttgctga tttatattaa ttttattgtt   540
caaacatgag agcttagtac gtgaaacatg agagcttagt acgttagcca tgagagctta   600
gtacgttagc catgagggtt tagttcgtta acatgagag cttagtacgt taaacatgag   660
agcttagtac gtgaaacatg agagcttagt acgtactatc aacaggttga actgctgatc   720
ttcagatcct ctacgccgga cgcatcgtgg ccggatcggg gggggggaa agccacgttg   780
tgtctcaaaa tctctgatgt tacattgcac aagataaaaa tatatcatca tgaacaataa   840
aactgtctgc ttacataaac agtaatacaa ggggtgttat gagccatatt caacgggaaa   900
cgtcttgctc gaggccgcga ttaaattcca acatggatgc tgatttatat gggtataaat   960
gggctcgcga taatgtcggg caatcaggtg cgacaatcta tcgattgtat gggaagcccg  1020
atgcgccaga gttgtttctg aaacatggca aaggtagcgt tgccaatgat gttacagatg  1080
agatggtcag actaaactgg ctgacggaat ttatgcctct tccgaccatc aagcatttta  1140
tccgtactcc tgatgatgca tggttactca ccactgcgat ccccgggaaa acagcattcc  1200
aggtattaga agaatatcct gattcaggtg aaaatattgt tgatgcgctg gcagtgttcc  1260
tgcgccggtt gcattcgatt cctgtttgta attgtccttt taacagcgat cgcgtatttc  1320
gtctcgctca ggcgcaatca cgaatgaata acggtttggt tgatgcgagt gattttgatg  1380
acgagcgtaa tggctggcct gttgaacaag tctggaaaga atgcataag cttttgccat  1440
tctcaccgga ttcagtcgtc actcatggtg atttctcact tgataacctt attttttgacg  1500
aggggaaatt aataggttgt attgatgttg gacgagtcgg aatcgcagac cgataccagg  1560
atcttgccat cctatggaac tgcctcggtg agttttctcc ttcattacag aaacggcttt  1620
```

```
ttcaaaaata tggtattgat aatcctgata tgaataaatt gcagtttcat ttgatgctcg    1680
atgagttttt ctaatcagaa ttggttaatt ggttgtaaca ctggcagagc attacgctga    1740
cttgacggga cggcggcttt gttgaataaa tcgaactttt gctgagttga aggatcagat    1800
cacgcatctt cccgacaacg cagaccgttc cgtggcaaag caaaagttca aaatcaccaa    1860
ctggtccacc tacaacaaag ctctcatcaa ccgtggctcc ctcactttct ggctggatga    1920
tggggcgatt caggcctggt atgagtcagc aacaccttct tcacgaggca gacctcagcg    1980
ccccccccc gatccagccg accaggcttt ccacgcccgc gtgccgctcc atgtcgttcg    2040
cgcggttctc ggaaacgcgc tgccgcgttt cgtgattgtc acgctcaagc ccgtagtccc    2100
gttcgagcgt cgcgcagagg tcagcgaggg cgcggtaggc ccgatacggc tcatggatgg    2160
tgtttcgggt cgggtgaatc ttgttgatgg cgatatggat gtgcaggttg tcggtgtcgt    2220
gatgcacggc actgacgcgc tgatgctcgg cgaagccaag cccagcgcag atgcggtcct    2280
caatcgcgcg caacgtctcc gcgtcgggct tctctcccgc gcggaagcta accagcaggt    2340
gataggtctt gtcggcctcg gaacgggtgt tgccgtgctg ggtcgccatc acctcggcca    2400
tgacagcggg cagggtgttt gcctcgcagt tcgtgacgcg cacgtgaccc aggcgctcgg    2460
tcttgccttg ctcgtcggtg atgtacttca ccagctccgc gaagtcgctc ttcttgatgg    2520
agcgcatggg gacgtgcttg gcaatcacgc gcacccccg gccgttttag cggctaaaaa    2580
agtcatggct ctgccctcgg gcggaccacg cccatcatga ccttgccaag ctcgtcctgc    2640
ttctcttcga tcttcgccag cagggcgagg atcgtggcat caccgaaccg cgccgtgcgc    2700
gggtcgtcgg tgagccagag tttcagcagg ccgcccaggc ggcccaggtc gccattgatg    2760
cgggccagct cgcggacgtg ctcatagtcc acgacgcccg tgattttgta gccctggccg    2820
acggccagca ggtaggccga caggctcatg ccggccgccg ccgccttttc ctcaatcgct    2880
cttcgttcgt ctggaaggca gtacaccttg ataggtgggc tgcccttcct ggttggcttg    2940
gtttcatcag ccatccgctt gccctcatct gttacgccgg cggtagccgg ccagcctcgc    3000
agagcaggat tcccgttgag caccgccagg tgcgaataag ggacagtgaa gaaggaacac    3060
ccgctcgcgg gtgggcctac ttcacctatc ctgcccggct gacgccgttg gatacaccaa    3120
ggaaagtcta cacgaaccct ttggcaaaat cctgtatatc gtgcgaaaaa ggatggatat    3180
accgaaaaaa tcgctataat gaccccgaag cagggttatg cagcggaaaa gcgctgcttc    3240
cctgctgttt tgtggaatat ctaccgactg gaaacaggca aatgcaggaa attactgaac    3300
tgaggggaca ggcgagagac gatgccaaag agctacaccg acgagctggc cgagtgggtt    3360
gaatcccgcg cggccaagaa gcgccggcgt gatgaggctg cggttgcgtt cctggcggtg    3420
agggcggatg tcgaggcggc gttagcgtcc ggctatgcgc tcgtcaccat ttgggagcac    3480
atgcgggaaa cggggaaggt caagttctcc tacgagacgt tccgctcgca cgccaggcgg    3540
cacatcaagg ccaagcccgc cgatgtgccc gcaccgcagg ccaaggctgc ggaacccgcg    3600
ccggcaccca agacgccgga gccacggcgg ccgaagcagg ggggcaaggc tgaaaagccg    3660
gcccccgctg cggcccccgac cggcttcacc ttcaacccaa caccggacaa aaaggatcga    3720
tccggcccct tcgtcttcaa gaattgtacc attcgccatt caggctgcgc aactgttggg    3780
aagggcgatc ggtgcgggcc tcttcgctat tacgccagct ggcgaaaggg ggatgtgctg    3840
caaggcgatt aagttgggta acgccagggt tttcccagtc acgacgttgt aaaacgacgg    3900
ccagtgaatt gtaatacgac tcactatagg gcgaattggg taccgggccc cccctcgagg    3960
```

```
tcgatcgacc tgcagttcat tacaccgctt ctcaacccgg tacgcaccag aaaatcattg    4020
atatggccat gaatggcgtt ggatgccggg caacagcccg cattatgggc gttggcctca    4080
acacgatttt acgtcactta aaaaactcag gccgcagtcg gtaacctcgc gcatacagcc    4140
gggcagtgac gtcatcgtct gcgcggaaat ggacgaacag tggggctatg tcggggctaa    4200
atcgcgccag cgctggctgt tttacgcgta tgacagtctc cggaagacgg ttgttgcgca    4260
cgtattcggt gaacgcacta tggcgacgct ggggcgtctt atgagcctgc tgtcacccct    4320
tgacgtggtg atatggatga cggatggctg gccgctgtat gaatcccgcc tgaagggaaa    4380
gctgcacgta atcagcaagc gatatacgca gcgaattgag cggcataacc tgaatctgag    4440
gcagcacctg gcacggctgg gacggaagtc gctgtcgttc tcaaaatcgg tggagctgca    4500
tgacaaagtc atcgggcatt atctgaacat aaaacactat caataagttg gagtcattac    4560
caaaaggtta ggaatacggt tagccatttg cctgctttta tatagttcat atgggattca    4620
cctttatgtt gataagaaat aaaagaaaat gccaatagga tatcggcatt ttcttttgcg    4680
tttttatttg ttaactgtta attgtccttg ttcaaggatg ctgtctttga caacagatgt    4740
tttcttgcct ttgatgttca gcaggaagct tggcgcaaac gttgattgtt tgtctgcgta    4800
gaatcctctg tttgtcatat agcttgtaat cacgacattg tttcctttcg cttgaggtac    4860
agcgaagtgt gagtaagtaa aggttacatc gttaggatca agatccattt ttaacacaag    4920
gccagttttg ttcagcggct tgtatgggcc agttaaagaa ttagaaacat aaccaagcat    4980
gtaaatatcg ttagacgtaa tgccgtcaat cgtcattttt gatccgcggg agtcagtgaa    5040
caggtaccat ttgccgttca ttttaaagac gttcgcgcgt tcaatttcat ctgttactgt    5100
gttagatgca atcagcggtt tcatcacttt tttcagtgtg taatcatcgt ttagctcaat    5160
cataccgaga gcgccgtttg ctaactcagc cgtgcgtttt ttatcgcttt gcagaagttt    5220
ttgactttct tgacggaaga atgatgtgct tttgccatag tatgctttgt taaataaaga    5280
ttcttcgcct tggtagccat cttcagttcc agtgtttgct tcaaatacta agtatttgtg    5340
gcctttatct tctacgtagt gaggatctct cagcgtatgg ttgtcgcctg agctgtagtt    5400
gccttcatcg atgaactgct gtacattttg atacgttttt ccgtcaccgt caaagattga    5460
tttataatcc tctacaccgt tgatgttcaa agagctgtct gatgctgata cgttaacttg    5520
tgcagttgtc agtgtttgtt tgccgtaatg tttaccggag aaatcagtgt agaataaacg    5580 gattttccg tcagatgtaa atgtggctga acctgaccat tcttgtgttt ggtcttttag     5640
gatagaatca tttgcatcga atttgtcgct gtctttaaag acgcggccag cgttttcca    5700 gctgtcaata gaagtttcgc cgactttttg atagaacatg taaatcgatg tgtcatccgc    5760
atttttagga tctccggcta atgcaaagac gatgtggtag ccgtgatagt ttgcgacagt    5820
gccgtcagcg ttttgtaatg gccagctgtc ccaaacctcc aggcctttg cagaagagat    5880 attttaatt gtggacgaat cgaattcagg aacttgatat ttttcatttt tttgctgttc    5940
agggatttgc agcatatcat ggcgtgtaat atgggaaatg ccgtatgttt ccttatatgg    6000
cttttggttc gtttctttcg caaacgcttg agttgcgcct cctgccagca gtgcggtagt    6060
aaaggttaat actgttgctt gttttgcaaa cttttttgatg ttcatcgttc atgtctcctt    6120
ttttatgtac tgtgttagcg gtctgcttct tccagccctc ctgtttgaag atggcaagtt    6180
agttacgcac aataaaaaaa gacctaaaat atgtaagggg tgacgccaaa gtatacactt    6240
tgccctttac acatttagg tcttgcctgc tttatcagta caaacccgc gcgatttact      6300 tttcgacctc attctattag actctcgttt ggattgcaac tggtctattt tcctcttttg    6360
```

| | | | | |
|---|---|---|---|---|
| tttgatagaa | aatcataaaa | ggatttgcag | actacgggcc | taaagaacta aaaaatctat | 6420 |
| ctgtttcttt | tcattctctg | tatttttat | agtttctgtt | gcatgggcat aaagttgcct | 6480 |
| ttttaatcac | aattcagaaa | atatcataat | atctcatttc | actaaataat agtgaacggc | 6540 |
| aggtatatgt | gatgggttaa | aaaggatcga | tcctctagag | tcgac | 6585 |

<210> SEQ ID NO 8
<211> LENGTH: 11370
<212> TYPE: DNA
<213> ORGANISM: Artificial Sequence
<220> FEATURE:
<223> OTHER INFORMATION: SYNTHESIZED

<400> SEQUENCE: 8

| | | | | |
|---|---|---|---|---|
| gaattcgagc | tcggtacccg | ggatcctct | agagtcgacc | tgcaggcatg caagcttgta | 60 |
| agaggttcca | actttcacca | taatgaaata | agatcactac | cgggcgtatt ttttgagtta | 120 |
| tcgagatttt | caggagctaa | ggaagctaaa | atggagaaaa | aaatcactgg atataccacc | 180 |
| gttgatatat | cccaatggca | tcgtaaagaa | cattttgagg | catttcagtc agttgctcaa | 240 |
| tgtacctata | accagaccgt | tcagctggat | attacggcct | ttttaaagac cgtaaagaaa | 300 |
| aataagcaca | agttttatcc | ggcctttatt | cacattcttg | cccgcctgat gaatgctcat | 360 |
| ccggaatttc | gtatggcaat | gaaagacggt | gagctggtga | tatgggatag tgttcaccct | 420 |
| tgttacaccg | ttttccatga | gcaaactgaa | acgttttcat | cgctctggag tgaataccac | 480 |
| gacgatttcc | ggcagtttct | acacatatat | tcgcaagatg | tggcgtgtta cggtgaaaac | 540 |
| ctggcctatt | tccctaaagg | gtttattgag | aatatgtttt | tcgtctcagc caatccctgg | 600 |
| gtgagtttca | ccagttttga | tttaaacgtg | gccaatatgg | acaacttctt cgcccccgtt | 660 |
| ttcaccatgg | gcaaatatta | tacgcaaggc | gacaaggtgc | tgatgccgct ggcgattcag | 720 |
| gttcatcatg | ccgtctgtga | tggcttccat | gtcggcagaa | tgcttaatga attacaacag | 780 |
| tactgcgatg | agtggcaggg | cggggcgtaa | tttttttaag | gcagttattg gtgcctagaa | 840 |
| atatttatc | tgattaataa | gatgatcttc | ttgagatcgt | tttggtctgc gaagcttggc | 900 |
| tgttttggcg | gatgagagaa | gattttcagc | ctgatacaga | ttaaatcaga acgcagaagc | 960 |
| ggtctgataa | aacagaattt | gcctggcggc | agtagcgcgg | tggtcccacc tgaccccatg | 1020 |
| ccgaactcag | aagtgaaacg | ccgtagcgcc | gatggtagtg | tggggtctcc ccatgcgaga | 1080 |
| gtagggaact | gccaggcatc | aaataaaacg | aaaggctcag | tcgaaagact gggcctttcg | 1140 |
| ttttatctgt | tgtttgtcgg | tgaacgctct | cctgagtagg | acaaatccgc cgggagcgga | 1200 |
| tttgaacgtt | gcgaagcaac | ggcccggagg | gtggcgggca | ggacgcccgc cataaactgc | 1260 |
| caggcatcaa | attaagcaga | aggccatcct | gacggatggc | cttttgcgt ttctacaaac | 1320 |
| tcttttgttt | attttctaa | atacattcaa | atatgtatcc | gctcatgaga caataaccct | 1380 |
| gataaatgct | tcaataatat | tgaaaaagga | agagtatgag | tattcaacat ttccgtgtcg | 1440 |
| cccttattcc | cttttttgcg | gcattttgcc | ttcctgtttt | tgctcaccca gaaacgctgg | 1500 |
| tgaaagtaaa | agatgctgaa | gatcagttgg | gtgcacgagt | gggttacatc gaactggatc | 1560 |
| tcaacagcgg | taagatcctt | gagagttttc | gccccgaaga | acgttttcca atgatgagca | 1620 |
| cttttaaagt | tctgctatgt | ggcgcggtat | tatcccgtgt | tgacgccggg caagagcaac | 1680 |
| tcggtcgccg | catacactat | tctcagaatg | acttggttga | gtactcacca gtcacagaaa | 1740 |
| agcatcttac | ggatggcatg | acagtaagag | aattatgcag | tgctgccata accatgagtg | 1800 |

```
ataacactgc ggccaactta cttctgacaa cgatcggagg accgaaggag ctaaccgctt    1860
ttttgcacaa catgggggat catgtaactc gccttgatcg ttgggaaccg gagctgaatg    1920
aagccatacc aaacgacgag cgtgacacca cgatgcctgt agcaatggca caacgttgc    1980 gcaaactatt aactggcgaa ctacttactc tagcttcccg gcaacaatta atagactgga    2040
tggaggcgga taaagttgca ggaccacttc tgcgctcggc ccttccggct ggctggttta    2100
ttgctgataa atctggagcc ggtgagcgtg gtctcgcgg tatcattgca gcactggggc    2160
cagatggtaa gccctcccgt atcgtagtta tctacacgac ggggagtcag gcaactatgg    2220
atgaacgaaa tagacagatc gctgagatag gtgcctcact gattaagcat tggtaactgt    2280
cagaccaagt ttactcatat atactttaga ttgatttctg aaagcgacca ggtgctcggc    2340
gtggcaagac tcgcagcgaa cccgtagaaa gccatgctcc agccgcccgc attggagaaa    2400
ttcttcaaat tcccgttgca catagcccgg caattccttt ccctgctctg ccataagcgc    2460
agcgaatgcc gggtaatact cgtcaacgat ctgatagaga agggtttgct cgggtcggtg    2520
gctctggtaa cgaccagtat cccgatcccg gctggccgtc ctggccgcca catgaggcat    2580
gttccgcgtc cttgcaatac tgtgtttaca tacagtctat cgcttagcgg aaagttcttt    2640
taccctcagc cgaaatgcct gccgttgcta gacattgcca gccagtgccc gtcactcccg    2700
tactaactgt cacgaacccc tgcaataact gtcacgcccc cctgcaataa ctgtcacgaa    2760
cccctgcaat aactgtcacg ccccaaacc tgcaaaccca gcagggcgg gggctggcgg    2820 ggtgttggaa aaatccatcc atgattatct aagaataatc cactaggcgc ggttatcagc    2880
gcccttgtgg ggcgctgctg cccttgccca atatgcccgg ccagaggccg gatagctggt    2940
ctattcgctg cgctaggcta cacaccgccc caccgctgcg cggcagggg aaaggcgggc    3000 aaagcccgct aaaccccaca ccaaacccg cagaaatacg ctggagcgct tttagccgct    3060
ttagcggcct ttccccctac ccgaagggtg ggggcgcgtg tgcagccccg cagggcctgt    3120
ctcggtcgat cattcagccc ggctcatcct tctggcgtgg cggcagaccg aacaaggcgc    3180
ggtcgtggtc gcgttcaagg tacgcatcca ttgccgccat gagccgatcc tccggccact    3240
cgctgctgtt caccttggcc aaaatcatgg ccccaccag caccttgcgc cttgtttcgt    3300
tcttgcgctc ttgctgctgt tcccttgccc gctcccgctg aatttcggca ttgattcgcg    3360
ctcgttgttc ttcgagcttg gccagccgat ccgccgcctt gttgctcccc ttaaccatct    3420
tgacacccca ttgttaatgt gctgtctcgt aggctatcat ggcgaaaagc aaaagcaaca    3480
gcgaggcagc atggcgattt atcaccttac ggcgaaaacc ggcagcaggt cgggcggcca    3540
atcggccagg gccaaggccg actacatcca gcgcgaaggc aagtatgccc gcgacatgga    3600
tgaagtcttg cacgccgaat ccgggcacat gccggagttc gtcgagcggc ccgccgacta    3660
ctgggatgct gccgacctgt atgaacgcgc caatggcgg ctgttcaagg aggtcgaatt    3720
tgccctgccg gtcgagctga ccctcgacca gcagaaggcg ctggcgtccg agttcgccca    3780
gcacctgacc ggtgccgagc gcctgccgta cgctggcc atccatgccg gtggcggcga    3840
gaacccgcac tgccacctga tgatctccga gcggatcaat gacggcatcg agcggcccgc    3900
cgctcagtgg ttcaagcggt acaacggcaa gaccccggag aagggcgggg cacagaagac    3960
cgaagcgctc aagcccaagg catggcttga gcagacccgc gaggcatggg ccgaccatgc    4020
caaccgggca ttagagcggg ctggccacga cgcccgcatt gaccacagaa cacttgaggc    4080
gcagggcatc gagcgcctgc ccggtgttca cctggggccg aacgtggtgg agatggaagg    4140
ccggggcatc cgcaccgacc gggcagacgt ggccctgaac atcgacaccg ccaacgccca    4200
```

```
gatcatcgac ttacaggaat accgggaggc aatagaccat gaacgcaatc gacagagtga    4260
agaaatccag aggcatcaac gagttagcgg agcagatcga accgctggcc cagagcatgg    4320
cgacactggc cgacgaagcc cggcaggtca tgagccagac caagcaggcc agcgaggcgc    4380
aggcggcgga gtggctgaaa gcccagcgcc agacaggggc ggcatggdtg gagctggcca    4440
aagagttgcg ggaggtagcc gccgaggtga gcagcgccgc gcagagcgcc cggagcgcgt    4500
cgcggggctg gcactggaag ctatggctaa ccgtgatgct ggcttccatg atgcctacgg    4560
tggtgctgct gatcgcatcg ttgctcttgc tcgacctgac gccactgaca accgaggacg    4620
gctcgatctg gctgcgcttg gtggcccgat gaagaacgac aggactttgc aggccatagg    4680
ccgacagctc aaggccatgg gctgtgagcg cttcgatatc ggcgtcaggg acgcacccac    4740
cggccagatg atgaacccgg aatggtcagc cgccgaagtg ctccagaaca cgccatggct    4800
caagcggatg aatgcccagg gcaatgacgt gtatatcagg cccgccgagc aggagcggca    4860
tggtctggtg ctggtggacg acctcagcga gtttgacctg gatgacatga aagccgaggg    4920
ccgggagcct gccctggtag tggaaaccag cccgaagaac tatcaggcat gggtcaaggt    4980
ggccgacgcc gcaggcggtg aacttcgggg gcagattgcc cggacgctgg ccagcgagta    5040
cgacgccgac ccggccagcg ccgacagccg ccactatggc cgcttggcgg gcttcaccaa    5100
ccgcaaggac aagcacacca cccgcgccgg ttatcagccg tgggtgctgc tgcgtgaatc    5160
caagggcaag accgccaccg ctggcccggc gctggtgcag caggctggcc agcagatcga    5220
gcaggcccag cggcagcagg agaaggcccg caggctggcc agcctcgaac tgcccgagcg    5280
gcagcttagc cgccaccggc gcacggcgct ggacgagtac cgcagcgaga tggccgggct    5340
ggtcaagcgc ttcggtcatg acctcagcaa gtgcgacttt atcgccgcgc agaagctggc    5400
cagccggggc cgcagtgccg aggaaatcgg caaggccatg gccgaggcca gcccagcgct    5460
ggcagagcgc aagcccggcc acgaagcgga ttacatcgag cgcaccgtca gcaaggtcat    5520
gggtctgccc agcgtccagc ttgcgcgggc cgagctggca cgggcaccgg caccccgcca    5580
gcgaggcatg gacaggggcg ggccagattt cagcatgtag tgcttgcgtt ggtactcacg    5640
cctgttatac tatgagtact cacgcacaga agggggtttt atggaatacg aaaaaagcgc    5700
ttcagggtcg gtctacctga tcaaaagtga caagggctat tggttgcccg gtggctttgg    5760
ttatacgtca aacaaggccg aggctggccg ctttttcagtc gctgatatgg ccagccttaa    5820
ccttgacggc tgcaccttgt ccttgttccg cgaagacaag cctttcggcc ccggcaagtt    5880
tctcggtgac tgatatgaaa gaccaaaagg acaagcagac cggcgacctg ctggccagcc    5940
ctgacgctgt acgccaagcg cgatatgccg agcgcatgaa ggccaaaggg atgcgtcagc    6000
gcaagttctg gctgaccgac gacgaatacg aggcgctgcg cgagtgcctg aagaactca    6060 gagcggcgca gggcgggggt agtgaccccg ccagcgccta accaccaact gcctgcaaag    6120
gaggcaatca atggctaccc ataagcctat caatattctg gaggcgttcg cagcagcgcc    6180
gccaccgctg gactacgttt tgcccaacat ggtggccggt acggtcgggg cgctggtgtc    6240
gcccggtggt gccggtaaat ccatgctggc cctgcaactg gccgcacaga ttgcaggcgg    6300
gccggatctg ctggaggtgg cgaactgcc caccggcccg gtgatctacc tgcccgccga    6360
agacccgccc accgccattc atcaccgcct gcacgccctt ggggcgcacc tcagcgccga    6420
ggaacggcaa gccgtggctg acggcctgct gatccagccg ctgatcggca gcctgcccaa    6480
catcatggcc ccggagtggt tcgacggcct caagcgcgcc gccgagggcc gccgcctgat    6540
```

```
ggtgctggac acgctgcgcc ggttccacat cgaggaagaa aacgccagcg gccccatggc    6600
ccaggtcatc ggtcgcatgg aggccatcgc cgccgatacc gggtgctcta tcgtgttcct    6660
gcaccatgcc agcaagggcg cggccatgat gggcgcaggc gaccagcagc aggccagccg    6720
gggcagctcg gtactggtcg ataacatccg ctggcagtcc tacctgtcga gcatgaccag    6780
cgccgaggcc gaggaatggg gtgtggacga cgaccagcgc cggttcttcg tccgcttcgg    6840
tgtgagcaag gccaactatg cgcaccgtt cgctgatcgg tggttcaggc ggcatgacgg    6900
cggggtgctc aagcccgccg tgctggagag gcagcgcaag agcaaggggg tgccccgtgg    6960
tgaagcctaa gaacaagcac agcctcagcc acgtccggca cgacccggcg cactgtctgg    7020
cccccggcct gttccgtgcc ctcaagcggg gcgagcgcaa gcgcagcaag ctggacgtga    7080
cgtatgacta cggcgacggc aagcggatcg agttcagcgg cccggagccg ctgggcgctg    7140
atgatctgcg catcctgcaa gggctggtgg ccatggctgg gcctaatggc ctagtgcttg    7200
gcccggaacc caagaccgaa ggcggacggc agctccggct gttcctggaa cccaagtggg    7260
aggccgtcac cgctgaatgc catgtggtca aggtagctga tcgggcgctg gcaaaggaaa    7320
tcggggcaga ggtcgatagt ggtgggcgc tcaagcacat acaggactgc atcgagcgcc    7380
tttggaaggt atccatcatc gcccagaatg gccgcaagcg gcaggggttt cggctgctgt    7440
cggagtacgc cagcgacgag gcggacgggc gcctgtacgt ggccctgaac cccttgatcg    7500
cgcaggccgt catgggtggc ggccagcatg tgcgcatcag catggacgag gtgcgggcgc    7560
tggacagcga aaccgcccgc ctgctgcacc agcggctgtg tggctggatc gaccccggca    7620
aaaccggcaa ggcttccata gataccttgt gcggctatgt ctggccgtca gaggccagtg    7680
gttcgaccat gcgcaagcgc cgcaagcggg tgcgcgaggc gttgccggag ctggtcgcgc    7740
tgggctggac ggtaaccgag ttcgcggcgg gcaagtacga catcacccgg cccaaggcgg    7800
caggctgacc cccccactc tattgtaaac aagacatttt tatcttttat attcaatggc    7860
ttatttcct gctaattggt aataccatga aaaataccat gctcagaaaa ggcttaacaa    7920
tattttgaaa aattgcctac tgagcgctgc cgcacagctc cataggccgc tttcctggct    7980
ttgcttccag atgtatgctc ttctgctccc gaacgccagc aagacgtagc ccagcgcgtc    8040
ggccagcttg caattcgcgc taacttacat taattgcgtt gcgctcactg cccgctttcc    8100
agtcgggaaa cctgtcgtgc cagctgcatt aatgaatcgg ccaacgcgcg gggagaggcg    8160
gtttgcgtat gggcgccag ggtggttttt ctttttcacca gtgagacggg caacagctga    8220
ttgcccttca ccgcctggcc ctgagagagt gcagcaagc ggtccacgtg gtttgcccca    8280
gcaggcgaaa atcctgtttg atggtggtta acggcgggat ataacatgag ctgtcttcgg    8340
tatcgtcgta tcccactacc gagatatccg caccaacgcg cagcccggac tcggtaatgg    8400
cgcgcattgc gcccagcgcc atctgatcgt tggcaaccag catcgcagtg gaacgatgc    8460
cctcattcag catttgcatg gtttgttgaa aaccggacat ggcactccag tcgccttccc    8520
gttccgctat cggctgaatt tgattgcgag tgagatattt atgccagcca gccagacgca    8580
gacgcgccga gacagaactt aatgggcccg ctaacagcgc gatttgctgg tgacccaatg    8640
cgaccagatg ctccacgccc agtcgcgtac cgtcttcatg ggagaaaata atactgttga    8700
tgggtgtctg gtcagagaca tcaagaaata acgccggaac attagtgcag gcagcttcca    8760
cagcaatggc atcctggtca tccagcggat agttaatgat cagcccactg acgcgttgcg    8820
cgagaagatt gtgcaccgcc gctttacagg cttcgacgcc gcttcgttct accatcgaca    8880
ccaccacgct ggcacccagt tgatcggcgc gagatttaat cgccgcgaca atttgcgacg    8940
```

```
gcgcgtgcag ggccagactg gaggtggcaa cgccaatcag caacgactgt ttgcccgcca    9000
gttgttgtgc cacgcggttg ggaatgtaat tcagctccgc catcgccgct tccactttt     9060 cccgcgtttt cgcagaaacg tggctggcct ggttcaccac gcgggaaacg gtctgataag    9120
agacaccggc atactctgcg acatcgtata acgttactgg tttcacattc accaccctga    9180
attgactctc ttccgggcgc tatcatgcca taccgcgaaa ggttttgcac cattcgatgg    9240
tgtcaacgta aatgccgctt cgccttcgcg cgcgaattgc aagctgatcc gggcttatcg    9300
actgcacggt gcaccaatgc ttctggcgtc aggcagccat cggaagctgt ggtatggctg    9360
tgcaggtcgt aaatcactgc ataattcgtg tcgctcaagg cgcactcccg ttctggataa    9420
tgttttttgc gccgacatca taacggttct ggcaaatatt ctgaaatgag ctgttgacaa    9480
ttaatcatcg gctcgtataa tgtgtggaat tgtgagcgga taacaatttc acacaggaaa    9540
cagaattcta agtaagtgt  aattggcggg cctgctctgt tatatgctgc attaccttat    9600
gcagatgaag tagttgtttc tcgcatcgtt aaaaggcatc gtgttaattc aacagttcaa    9660
ttagacgcaa gttttcttga tgatataagc aagcgtgaaa tggttgaaac gcattggtat    9720
aaaatagatg aagtaacaac ccttacggaa tcagtatata aatgaaacaa taccaagatt    9780
taattaaaga cattttgaa  aatggttatg aaaccgatga tcgtacaggc acaggaacaa    9840
ttgctctgtt cggatctaaa ttcgctggg  atttaactaa aggttttcct gcggtaacaa    9900
ctaagaagct cgcctggaaa gcttgcattg ctgagctaat atggttttta tcaggaagca    9960
caaatgtcaa tgatttacga ttaattcaac acgattcgtt aatccaaggc aaaacagtct   10020
gggatgaaaa ttacgaaaat caagcaaaag atttaggata ccatagcggt gaacttggtc   10080
caatttatgg aaaacagtgg cgtgattttg gtggtgtaga ccaaattata gaagttattg   10140
atcgtattaa aaaactgcca aatgataggc gtcaaattgt ttctgcatgg aatccagctg   10200
aacttaaata tatggcatta ccgccttgtc atatgttcta tcagtttaat gtgcgtaatg   10260
gctatttgga tttgcagtgg tatcaacgct cagtagatgt tttcttgggt ctaccgttta   10320
atattgcgtc atatgctacg ttagttcata ttgtagctaa gatgtgtaat cttattccag   10380
gggatttgat attttctggt ggtaatactc atatctatat gaatcacgta gaacaatgta   10440
aagaaatttt gaggcgtgaa cctaaagagc tttgtgagct ggtaataagt ggtctaccttt  10500 ataaattccg atatctttct actaaagaac aattaaaata tgttcttaaa cttaggccta   10560
aagatttcgt tcttaacaac tatgtatcac accctcctat taaaggaaag atggcggtgt   10620
aattttatta ttgcgaggat atatgatttt acgatttaaa gatacttctg gtgtagttct   10680
ttttacactt cctaacccaa gcgagttaga agttccagga ccagaacagc ctattaccat   10740
ttatggtaaa aaatactata ctcataaaat gacctcgtga gtattttgat aataaaaatt   10800
tccacagtta aaacttcttc tgactgttac tacgatatta ctgttttaac ggaaaacaat   10860
atgacgaatt attccagcgt gggccgtcta tgccggtag  tgaataaata taatccgac    10920 tttgatgtta atattcaccg cggtacattt tggggaaatt acgtcggtaa agatgctggc   10980
agccgggagg ctgccattga attattcaaa aaagatttat acgtcgaatt aaatccggag   11040
aaataactaa agcacattta gagcctttac gtggaatgag gctaggatgc acatgtaaac   11100
caaagccgtg tcatggtgat ataatagctc atatagttaa ccgattgttt aaagacgatt   11160
ttcaagttga ggacttatgc aattaattaa tgttatcaaa agtagtggtg tttctcagag   11220
ctttgaccca caaaaaatta ttaaagtttt atcttgggca gctgaaggaa catcagtaga   11280
```

| | |
|---|---|
| tccttatgaa ttatatgaaa atattaaatc ttatctccgt gatggaatga caactgatga | 11340 |
| tattcagact attgtcatta aggctgctgc | 11370 |

<210> SEQ ID NO 9
<211> LENGTH: 10547
<212> TYPE: DNA
<213> ORGANISM: Artificial Sequence
<220> FEATURE:
<223> OTHER INFORMATION: SYNTHESIZED

<400> SEQUENCE: 9

| | |
|---|---|
| gtcgacgctc aattgtatgt tcgttatgaa gatgggactt taaaaaaagt tctatttaca | 60 |
| ggcaatgaat acattaatat caaaaaacct gccgccggaa attatcatat tttaataaag | 120 |
| ggaattgctg cgaatacagt taacttaact gcttttttatg gcaatttaca gtaatgcagt | 180 |
| atgaaataat ttcttatagg gattggctat ttaagacatc aattgccaat cctatttaaa | 240 |
| ctgttagatg taaaatcaat tcaaatgagc aatcacaaaa aggccatgta aggaaaatat | 300 |
| ataattcaag tgaactcaat agaggttttt tttaactatt tgattcatta tttatttcga | 360 |
| tgaatcaaaa aatccatcta taactcaaac tttataaagt taagaatgag tatgaatttg | 420 |
| aggataaatg atgcaaagca taaaaaaacg aatggcagaa gtaaagtcaa tacatgagtt | 480 |
| aaatactcta ttaaaaaatt attttttggag tataagtata aaaagctttg cctttaccta | 540 |
| ttataatcaa cacaccaaaa caggaagcaa attggtatat gagtgggcaa ctacacccct | 600 |
| ggatgcgtgg cataaatatt atctgcaaga aggttatgct gatattgatc gtactcttga | 660 |
| agccacagaa caatctttat tgcctatttt ttgggatgtg aaagaacaat tacgtttggc | 720 |
| taaaaataaa agaatgcggc ggtttaaaca agagtctctt atctttgggc ttgataaggg | 780 |
| attatgcatt cctttacatg gtcctaaagg tgaatttgtc attttggtgt tacatcagcg | 840 |
| aattaatgaa catggtttaa aaaattggga aaatcatgtg gatacttggc ttggcatctt | 900 |
| acacacctat tttcatttt taaggttact gttgaatgaa aaaaaaatag gtgtagtgcc | 960 |
| tctgacaaaa cgtgaacaag aatgcttgag actaactgcc gagggattcc gtttggaact | 1020 |
| gattgcacaa ttattaaaaa ttagtaagcg taccgtgaat tttcatttac aaaacgccaa | 1080 |
| taaaaaactc ggggttacca ataaatattt agctattatg gctctatgga atcatgatcc | 1140 |
| tcgagtaaac cataataagc ccaataaaat ttgaatccaa taataaaaaa taagtttcaa | 1200 |
| gattaccgaa aagatcagac atatccagca atcgactatc atgtatacac aaataaagaa | 1260 |
| aggactgctc tagctctgga atacaacgaa ccccaaaagt gccattgtat ccttttttgt | 1320 |
| attttattag ttacctcttc tcttaaaagg gatccgccgg cgaaatggtt tcaacctgag | 1380 |
| ccgtttgtat caattcacct catgaattac tccccttttcc ccttttttgca atggattaag | 1440 |
| ccattcacaa gtaaaacatc ctgatcatgt gaacgatgtc attagatctt tcaatttggt | 1500 |
| ataataaagc taaagtttga ttgctcttca agatgctgta gataacaaaa ccaacaacac | 1560 |
| caaaaaaatt tatcatgtac gcaatttaaa agtaatgctg gatagcgagc ctctaagggt | 1620 |
| cgatggaatt gtctcaaaat ttttaacca ggcaattaaa cgaactattg ataaatttcc | 1680 |
| tgatgagttc atgttccaac ttaatgaaac tgagtttgat tgcttttgat caccaataga | 1740 |
| tatctcaagt tggcatgaag ggtagaagat atttgcccta tgtttttaaa gaacaaggta | 1800 |
| ttgccatgct ttctgcagca ttaagaagtg aaactgcaat tgacgttagt atccacagga | 1860 |
| atatgggcga ggaatgcatt cagcaataaa gcaatcaatt ttattcaata tacaataaca | 1920 |
| gaaatatcaa aaatgagtta tttaaaataa ttaaatctaa taaggtaatt atcaatgtct | 1980 |

```
aaaaatatca aaattctcgt cattggcgcg gccgccaatt tcgaatggga ttaccttacc    2040
tcaatatgaa tcatcatagt ggactatgga gtttaattat cagacactca ttttgagtgt    2100
ttgaatttgc ttatcagcac tgagtagatt ggatattctt gtcaatgata atgtcgccgc    2160
ggaagcaaca aaaattccta gcgtgaatgt aagaataaat aagattaatc agctaacgcc    2220
cttaaatgta taccttgaga ttttggggca tatgttcaat tgcaggtgtt tgttcctaaa    2280
tgtaaaagtt aaggaacaaa tcgctgtaaa gtccaatttt catcagtaca tattgcagtt    2340
attgagtccg acaaccgatg ctcatttaat tgataaagtt ttatctcgtc aggaacaatc    2400
atataaccaa tatactctcg cggtcgttct gggagtgttt ttttatattg ctcctttaag    2460
gtaaataact cttcatctaa ctcctgttgt ttctttatca attgcccaga ctttgtgcca    2520
tagactaaaa aacgtaacct gcgctcttga tcataagtat cccagttttt taaattttca    2580
tgttccccaa gtgcccttac tctaccaaaa accgtaattt gtctttgtgt attcggtaac    2640 ataaagtaa aagaagtata gggattaaca aaaatatgcg ctactttgc gctacccagc     2700 tgcgtaaaaa aagaaaccc gtgttcgttt atttcacgaa tagctactgt gcggcttctt    2760
ggcaatccat tttcatctac tgtggctaaa ccccccatca taaagggtag attttctgcc    2820
tctacccaaa ccttaattaa tcttaacaac caaccaaaat caacttgttc aggtaactct    2880
tctagaaaac agtctctgtc agtgaatcgc atttttatat cacttttcct actcagatga    2940
gttgaattat attactactt aagcaatcat cataattcaa tctttaactc ttctcatttt    3000
atgtgtaagt taatgtgtgt tatttttgata gagttttttt tagcggtaat aataatcgtt    3060
tctgagtttg acagaatagt ttttgatcaa ctaaaaagca catcccctg aatcatcgta     3120 cgaagtttag gcttgttata attcctatgt tgtagcttgc tctcctgtag cttaatcata    3180
gctcatcact tagcatgagt atcgccattg caaacccgtt tgagtagttg ctatgagaac    3240
taccctaata tgggtttact actatttatc aatccattag agcgccgaat tcattcaaa     3300 cgtttcctgg atttgggta ccatttgtca acacacccta atagatgaaa actcaaaagt     3360
ttgggataga taaaaaattg gattaactgg caatagctcc ataaatggct ttatattcat    3420
ttgttaaggc agcccataat cgatcaccat atgagaaatg ccaccattca ttaggataat    3480
taacaaaacc aagatcgagc attatctcta aaagaatcat tctatttta aatgctactc     3540 ttgaaatatt tttagagtgc gttttacaaa tatcgggatc gactttatac caatctttaa    3600
tttccatgcc taaattaatt aaattgccat tgatatcaat taactctaaa tcaactgcgc    3660
cacctgtact atgtggtgga ataatcggtg taccatcata tgagtatatt ggacaaacaa    3720
gtttgctggc gtcaatgaaa agttcctctt catttctgtg aggcttttgg gattttaacc    3780
tattgatttg ttggttaaat aatattttt gaacacgtag acttcgcaat ccttcgtata     3840
ctttaaattt ccaattacaa ggaagcatgt tttgagcgat aagaagtttt tcataaactg    3900
attttcgaat ttttgtgtaa tcattatatg ttaatggggt atcaggtgga gagccaaata    3960
acaaatattg ttgatccttt aaatccacta gaggttcatt gttttcatgg attggaattg    4020
tattaatctt gatatcatta agcgagctcc agcttttgtt cccttagtg agggttaatt     4080 tcgagcttgg cgtaatcatg gtcatagctg tttcctgtgt gaaattgtta ccgctcaca    4140 attccacaca acatacgagc cggaagcata aagtgtaaag cctggggtgc ctaatgagtg    4200
agctaactca cattaattgc gttgcgctca ctgcccgctt tccagtcggg aaacctgtcg    4260
tgccagctgc attaatgaat cggccaacgc tacaattccc atgtcagccg ttaagtgttc    4320
```

```
ctgtgtcact caaaattgct ttgagaggct ctaagggctt ctcagtgcgt tacatccctg    4380
gcttgttgtc cacaaccgtt aaaccttaaa agctttaaaa gccttatata ttcttttttt    4440
tcttataaaa cttaaaacct tagaggctat ttaagttgct gatttatatt aattttattg    4500
ttcaaacatg agagcttagt acgtgaaaca tgagagctta gtacgttagc catgagagct    4560
tagtacgtta gccatgaggg tttagttcgt taaacatgag agcttagtac gttaaacatg    4620
agagcttagt acgtgaaaca tgagagctta gtacgtacta tcaacaggtt gaactgctga    4680
tcttcagatc ctctacgccg gacgcatcgt ggccggatcg gggggggggg aaagccacgt    4740
tgtgtctcaa aatctctgat gttacattgc acaagataaa aatatatcat catgaacaat    4800
aaaactgtct gcttacataa acagtaatac aaggggtgtt atgagccata ttcaacggga    4860
aacgtcttgc tcgaggccgc gattaaattc caacatggat gctgatttat atgggtataa    4920
atgggctcgc gataatgtcg ggcaatcagg tgcgacaatc tatcgattgt atgggaagcc    4980
cgatgcgcca gagttgtttc tgaaacatgg caaaggtagc gttgccaatg atgttacaga    5040
tgagatggtc agactaaact ggctgacgga atttatgcct cttccgacca tcaagcattt    5100
tatccgtact cctgatgatg catggttact caccactgcg atccccggga aaacagcatt    5160
ccaggtatta gaagaatatc ctgattcagg tgaaaatatt gttgatgcgc tggcagtgtt    5220
cctgcgccgg ttgcattcga ttcctgtttg taattgtcct tttaacagcg atcgcgtatt    5280
tcgtctcgct caggcgcaat cacgaatgaa taacggtttg gttgatgcga gtgattttga    5340
tgacgagcgt aatggctggc ctgttgaaca gtctggaaa gaaatgcata agcttttgcc    5400
attctcaccg gattcagtcg tcactcatgg tgatttctca cttgataacc ttatttttga    5460
cgaggggaaa ttaataggtt gtattgatgt tggacgagtc ggaatcgcag accgatacca    5520
ggatcttgcc atcctatgga actgcctcgg tgagttttct ccttcattac agaaacggct    5580
ttttcaaaaa tatggtattg ataatcctga tatgaataaa ttgcagtttc atttgatgct    5640
cgatgagttt ttctaatcag aattggttaa ttggttgtaa cactggcaga gcattacgct    5700
gacttgacgg gacggcggct ttgttgaata atcgaacttt tgctgagtt gaaggatcag    5760 atcacgcatc ttcccgacaa cgcagaccgt tccgtggcaa agcaaaagtt caaaatcacc    5820
aactggtcca cctacaacaa agctctcatc aaccgtggct ccctcacttt ctggctggat    5880 gatgggcgatt caggcctg gtatgagtca gcaacaccttt cttcacgagg cagacctcag    5940 cgccccccccc ccgatccagc cgaccaggct ttccacgccc gcgtgccgct ccatgtcgtt    6000
cgcgcggttc tcggaaacgc gctgccgcgt ttcgtgattg tcacgctcaa gcccgtagtc    6060
ccgttcgagc gtcgcgcaga ggtcagcgag ggcgcggtag gcccgatacg gctcatggat    6120
ggtgtttcgg gtcgggtgaa tcttgttgat ggcgatatgg atgtgcaggt tgtcggtgtc    6180
gtgatgcacg gcactgacgc gctgatgctc ggcgaagcca agcccagcgc agatgcggtc    6240
ctcaatcgcg cgcaacgtct ccgcgtcggg cttctctccc gcgcggaagc taaccagcag    6300
gtgataggtc ttgtcggcct cggaacgggt gttgccgtgc tgggtcgcca tcacctcggc    6360
catgacagcg gcagggtgt tgcctcgca gttcgtgacg cgcacgtgac ccaggcgctc    6420
ggtcttgcct tgctcgtcgg tgatgtactt caccagctcc gcgaagtcgc tcttcttgat    6480
ggagcgcatg gggacgtgct tggcaatcac gcgcaccccc cggccgtttt agcggctaaa    6540
aaagtcatgg ctctgccctc gggcggacca cgcccatcat gaccttgcca agctcgtcct    6600
gcttctcttc gatcttcgcc agcagggcga ggatcgtggc atcaccgaac cgcgccgtgc    6660
gcgggtcgtc ggtgagccag agtttcagca ggccgcccag gcggcccagg tcgccattga    6720
```

```
tgcgggccag ctcgcggacg tgctcatagt ccacgacgcc cgtgattttg tagccctggc    6780
cgacggccag caggtaggcc gacaggctca tgccggccgc cgccgccttt tcctcaatcg    6840
ctcttcgttc gtctggaagg cagtacacct tgataggtgg gctgcccttc ctggttggct    6900
tggtttcatc agccatccgc ttgccctcat ctgttacgcc ggcggtagcc ggccagcctc    6960
gcagagcagg attcccgttg agcaccgcca ggtgcgaata agggacagtg aagaaggaac    7020
acccgctcgc gggtgggcct acttcaccta tcctgcccgg ctgacgccgt tggatacacc    7080
aaggaaagtc tacacgaacc ctttggcaaa atcctgtata tcgtgcgaaa aaggatggat    7140
ataccgaaaa aatcgctata atgacccccga agcagggtta tgcagcggaa aagcgctgct    7200
tccctgctgt tttgtggaat atctaccgac tggaaacagg caaatgcagg aaattactga    7260 actgaggggda caggcgagag acgatgccaa agagctacac cgacgagctg gccgagtggg    7320
ttgaatcccg cgcggccaag aagcgccggc gtgatgaggc tgcggttgcg ttcctggcgg    7380
tgagggcgga tgtcgaggcg gcgttagcgt ccggctatgc gctcgtcacc atttgggagc    7440
acatgcggga aacggggaag gtcaagttct cctacgagac gttccgctcg cacgccaggc    7500
ggcacatcaa ggccaagccc gccgatgtgc ccgcaccgca ggccaaggct gcggaacccg    7560
cgccggcacc caagacgccg gagccacggc ggccgaagca gggggggcaag gctgaaaagc    7620 cggcccccgc tgcggccccg accggcttca ccttcaaccc aacaccggac aaaaaggatc    7680
gatccggccc tttcgtcttc aagaattgta ccattcgcca ttcaggctgc gcaactgttg    7740
ggaagggcga tcggtgcggg cctcttcgct attacgccag ctggcgaaag ggggatgtgc    7800
tgcaaggcga ttaagttggg taacgccagg gttttcccag tcacgacgtt gtaaaacgac    7860
ggccagtgaa ttgtaatacg actcactata gggcgaattg ggtaccgggc cccccctcga    7920
ggtcgatcga cctgcagttc attacaccgc ttctcaaccc ggtacgcacc agaaaatcat    7980
tgatatggcc atgaatggcg ttggatgccg ggcaacagcc cgcattatgg gcgttggcct    8040
caacacgatt ttacgtcact aaaaaactc aggccgcagt cggtaacctc gcgcatacag    8100
ccgggcagtg acgtcatcgt ctgcgcggaa atggacgaac agtggggcta tgtcggggct    8160
aaatcgcgcc agcgctggct gttttacgcg tatgacagtc tccggaagac ggttgttgcg    8220
cacgtattcg gtgaacgcac tatggcgacg ctggggcgtc ttatgagcct gctgtcaccc    8280
tttgacgtgg tgatatggat gacggatggc tgccgctgt atgaatcccg cctgaaggga    8340
aagctgcacg taatcagcaa gcgatatacg cagcgaattg agcggcataa cctgaatctg    8400
aggcagcacc tggcacggct gggacggaag tcgctgtcgt tctcaaaatc ggtggagctg    8460
catgacaaag tcatcgggca ttatctgaac ataaacact atcaataagt tggagtcatt    8520
accaaaaggt taggaatacg gttagccatt tgcctgcttt tatatagttc atatgggatt    8580
cacctttatg ttgataagaa ataaaagaaa atgccaatag gatatcggca ttttcttttg    8640 cgttttatt tgttaactgt taattgtcct tgttcaagga tgctgtcttt gacaacagat    8700
gttttcttgc ctttgatgtt cagcaggaag cttggcgcaa acgttgattg tttgtctgcg    8760
tagaatcctc tgtttgtcat atagcttgta atcacgacat tgtttccttt cgcttgaggt    8820
acagcgaagt gtgagtaagt aaaggttaca tcgttaggat caagatccat ttttaacaca    8880
aggccagttt tgttcagcgg cttgtatggg ccagttaaag aattagaaac ataaccaagc    8940
atgtaaatat cgttagacgt aatgccgtca atcgtcattt ttgatccgcg ggagtcagtg    9000
aacaggtacc atttgccgtt cattttaaag acgttcgcgc gttcaatttc atctgttact    9060
```

```
gtgttagatg caatcagcgg tttcatcact tttttcagtg tgtaatcatc gtttagctca      9120
atcataccga gagcgccgtt tgctaactca gccgtgcgtt ttttatcgct ttgcagaagt      9180
ttttgacttt cttgacggaa gaatgatgtg cttttgccat agtatgcttt gttaaataaa      9240
gattcttcgc cttggtagcc atcttcagtt ccagtgtttg cttcaaatac taagtatttg      9300
tggcctttat cttctacgta gtgaggatct ctcagcgtat ggttgtcgcc tgagctgtag      9360
ttgccttcat cgatgaactg ctgtacattt tgatacgttt ttccgtcacc gtcaaagatt      9420
gatttataat cctctacacc gttgatgttc aaagagctgt ctgatgctga tacgttaact      9480
tgtgcagttg tcagtgtttg tttgccgtaa tgtttaccgg agaaatcagt gtagaataaa      9540
cggattttcc cgtcagatgt aaatgtggct gaacctgacc attcttgtgt ttggtctttt      9600
aggatagaat catttgcatc gaatttgtcg ctgtctttaa agacgcggcc agcgtttttc      9660
cagctgtcaa tagaagtttc gccgactttt tgatagaaca tgtaaatcga tgtgtcatcc      9720
gcatttttag gatctccggc taatgcaaag acgatgtggt agccgtgata gtttgcgaca      9780
gtgccgtcag cgttttgtaa tggccagctg tcccaaacct ccaggccttt tgcagaagag      9840 atattttttaa ttgtggacga atcgaattca ggaacttgat attttttcatt tttttgctgt      9900 tcagggattt gcagcatatc atggcgtgta atatgggaaa tgccgtatgt ttccttatat      9960
ggcttttggt tcgtttcttt cgcaaacgct tgagttgcgc ctcctgccag cagtgcggta     10020
gtaaaggtta atactgttgc ttgttttgca aacttttttga tgttcatcgt tcatgtctcc     10080
ttttttatgt actgtgttag cggtctgctt cttccagccc tcctgtttga agatggcaag     10140
ttagttacgc acaataaaaa aagacctaaa atatgtaagg ggtgacgcca aagtatacac     10200
tttgcccttt acacatttta ggtcttgcct gctttatcag taacaaaccc gcgcgattta     10260
cttttcgacc tcattctatt agactctcgt ttggattgca actggtctat tttcctcttt     10320
tgtttgatag aaaatcataa aaggatttgc agactacggg cctaaagaac taaaaaatct     10380
atctgtttct tttcattctc tgtattttt atagtttctg ttgcatgggc ataaagttgc     10440 cttttttaatc acaattcaga aaatatcata atatctcatt tcactaaata atagtgaacg     10500
gcaggtatat gtgatgggtt aaaaaggatc gatcctctag agtcgac                    10547
```

<210> SEQ ID NO 10
<211> LENGTH: 12557
<212> TYPE: DNA
<213> ORGANISM: Artificial Sequence
<220> FEATURE:
<223> OTHER INFORMATION: SYNTHESIZED

<400> SEQUENCE: 10

```
gaattcgagc tcggtacccg gggatcctaa gaggagaaat taactatgtc taaaaatatc        60
aaaattctcg tcattggcgc tggtgtagct ggccctgctg tttgttattg gctaagaagg       120
tttggttttt ctcctgtttt gattgaaaaa tatgcgtcta ttagaaaagg gggtcaggca       180
ctggatgttc gtggcatagc aactcatatc gccagagaaa tgggtatcta tgatcaaata       240
tgtgagatgc gcacgcgaat agagcgcggt cgctttgtag actcatcggg taaagtgctg       300
catgaagaac agggtgagaa attcgggttt aggcaagatg acgaagtcga aattctccgt       360
ggtgatttgg ttgaaatcct gatgaaaaca attgctgatg tcccttgtta tttcaatcaa       420
tccattatta gcattgagca gaatgctgat aacgttaccg ttattttcat ggatggcagg       480
attgaacaat atgatctggt gatcgctgca gatgggattc actctgctat aaggcgcatg       540
atttttgaaa aaaatgaata tcagttaatt caccttggcg catatctcag tacatttacc       600
```

```
attccaaatt accttggctt gagtcacata gatctggaat gtgaggctaa taataaatta      660
gtctcaataa atagcgataa caatcctgaa atagcaagag caggatttat gttccgttcc      720
cagcatctcc tgaatgacat ccgtgatgag caggaacaaa agcaattcct acgtgatact      780
tttcgcgatt ttggctggga aacacaaaat attttaaatc gaatgccaga aagcaatgat      840
ttttattttg atgcgattac gcaagtaaaa atgaatagtt ggaccaaagg tcgaatagcg      900
cttgtcggtg atgcaggcta ttgtccttct ccgttatctg gccaagggaa taatttggca      960
ttcgttggag catatatact ggcgggagaa ttaaaagttg ctaatggaaa ttatacccga     1020
gcgtttactc gttataatgc actgctacgt tccttcgttg atgccaatca aaaatttggt     1080
gtttgggtca gtgaatcatt ccttgtaaaa gatgaagttt ccaaggaaat tgcagaagaa     1140
cgctcgaaca aaatcctagc catgataaaa tcaatttcga atgggattac cttacctcaa     1200
tatgaatcat catagtggac gtcgacctgc aggcatgcaa gcttgtaaga ggttccaact     1260
ttcaccataa tgaaataaga tcactaccgg gcgtattttt tgagttatcg attttcag     1320 gagctaagga agctaaaatg gagaaaaaaa tcactggata taccaccgtt gatatatccc     1380
aatggcatcg taaagaacat tttgaggcat ttcagtcagt tgctcaatgt acctataacc     1440
agaccgttca gctggatatt acggcctttt taaagaccgt aaagaaaaat aagcacaagt     1500
tttatccggc cttttattcac attcttgccc gcctgatgaa tgctcatccg gaatttcgta     1560
tggcaatgaa agacggtgag ctggtgatat gggatagtgt tcacccttgt tacaccgttt     1620
tccatgagca aactgaaacg ttttcatcgc tctggagtga ataccacgac gatttccggc     1680
agtttctaca catatattcg caagatgtgg cgtgttacgg tgaaaacctg gcctatttcc     1740
ctaaagggtt tattgagaat atgttttcg tctcagccaa tccctgggtg agtttcacca     1800
gttttgattt aaacgtggcc aatatggaca acttcttcgc cccgttttc accatgggca     1860 aatattatac gcaaggcgac aaggtgctga tgccgctggc gattcaggtt catcatgccg     1920
tctgtgatgg cttccatgtc ggcagaatgc ttaatgaatt acaacagtac tgcgatgagt     1980
ggcagggcgg ggcgtaattt ttttaaggca gttattggtg cctagaaata ttttatctga     2040
ttaataagat gatcttcttg agatcgtttt ggtctgcgaa gcttggctgt tttggcggat     2100
gagagaagat tttcagcctg atacagatta aatcagaacg cagaagcggt ctgataaaac     2160
agaatttgcc tggcggcagt agcgcggtgg tcccacctga ccccatgccg aactcagaag     2220
tgaaacgccg tagcgccgat ggtagtgtgg ggtctcccca tgcgagagta gggaactgcc     2280
aggcatcaaa taaaacgaaa ggctcagtcg aaagactggg cctttcgttt tatctgttgt     2340
ttgtcggtga acgctctcct gagtaggaca atccgccgg gagcggattt gaacgttgcg     2400
aagcaacggc ccgagggtg gcgggcagga cgcccgccat aaactgccag gcatcaaatt     2460
aagcagaagg ccatcctgac ggatggcctt tttgcgtttc tacaaactct tttgtttatt     2520
tttctaaata cattcaaata tgtatccgct catgagacaa taaccctgat aaatgcttca     2580
ataatattga aaaggaaga gtatgagtat tcaacatttc cgtgtcgccc ttattccctt     2640
ttttgcggca ttttgccttc ctgttttgc tcacccagaa acgctggtga agtaaaaga     2700 tgctgaagat cagttgggtg cacgagtggg ttacatcgaa ctggatctca acagcggtaa     2760
gatccttgag agttttcgcc ccgaagaacg ttttccaatg atgagcactt ttaaagttct     2820
gctatgtggc gcggtattat cccgtgttga cgccgggcaa gagcaactcg gtcgccgcat     2880
acactattct cagaatgact tggttgagta ctcaccagtc acagaaaagc atcttacgga     2940
```

```
tggcatgaca gtaagagaat tatgcagtgc tgccataacc atgagtgata acactgcggc    3000
caacttactt ctgacaacga tcggaggacc gaaggagcta accgcttttt tgcacaacat    3060
gggggatcat gtaactcgcc ttgatcgttg gaaccggag ctgaatgaag ccataccaaa    3120
cgacgagcgt gacaccacga tgcctgtagc aatggcaaca acgttgcgca aactattaac    3180
tggcgaacta cttactctag cttcccggca acaattaata gactggatgg aggcggataa    3240
agttgcagga ccacttctgc gctcggccct tccggctggc tggtttattg ctgataaatc    3300
tggagccggt gagcgtgggt ctcgcggtat cattgcagca ctggggccag atggtaagcc    3360
ctcccgtatc gtagttatct acacgacggg gagtcaggca actatggatg aacgaaatag    3420
acagatcgct gagataggtg cctcactgat taagcattgg taactgtcag accaagttta    3480
ctcatatata ctttagattg atttctgaaa gcgaccaggt gctcggcgtg caagactcg    3540 cagcgaaccc gtagaaagcc atgctccagc cgcccgcatt ggagaaattc ttcaaattcc    3600
cgttgcacat agcccggcaa ttccttccc tgctctgcca taagcgcagc gaatgccggg    3660
taatactcgt caacgatctg atagagaagg gtttgctcgg gtcggtggct ctggtaacga    3720
ccagtatccc gatcccggct ggccgtcctg gccgccacat gaggcatgtt ccgcgtcctt    3780
gcaatactgt gtttacatac agtctatcgc ttagcggaaa gttcttttac cctcagccga    3840
aatgcctgcc gttgctagac attgccagcc agtgcccgtc actcccgtac taactgtcac    3900 gaaccctgc aataactgtc acgcccccct gcaataactg tcacgaaccc ctgcaataac    3960
tgtcacgccc ccaaacctgc aaacccagca ggggcggggg ctggcggggt gttggaaaaa    4020
tccatccatg attatctaag aataatccac taggcgcggt tatcagcgcc cttgtggggc    4080
gctgctgccc ttgcccaata tgcccggcca gaggccggat agctggtcta ttcgctgcgc    4140
taggctacac accgccccac cgctgcgcgg caggggaaa ggcgggcaaa gcccgctaaa    4200
ccccacacca aaccccgcag aaatacgctg gagcgctttt agccgcttta gcggcctttc    4260
cccctacccg aagggtgggg gcgcgtgtgc agccccgcag gcctgtctc ggtcgatcat    4320 tcagcccggc tcatccttct ggcgtggcgg cagaccgaac aaggcgcggt cgtggtcgcg    4380
ttcaaggtac gcatccattg ccgccatgag ccgatcctcc ggccactcgc tgctgttcac    4440
cttggccaaa atcatggccc ccaccagcac cttgcgcctt gtttcgttct tgcgctcttg    4500
ctgctgttcc cttgcccgct cccgctgaat ttcggcattg attcgcgctc gttgttcttc    4560
gagcttggcc agccgatccg ccgccttgtt gctcccctta accatcttga caccccattg    4620
ttaatgtgct gtctcgtagg ctatcatggc gaaaagcaaa agcaacagcg aggcagcatg    4680
gcgatttatc accttacggc gaaaaccggc agcaggtcgg gcggccaatc ggccagggcc    4740
aaggccgact acatccagcg cgaaggcaag tatgcccgcg acatggatga agtcttgcac    4800
gccgaatccg ggcacatgcc ggagttcgtc gagcggcccg ccgactactg ggatgctgcc    4860
gacctgtatg aacgcgccaa tgggcggctg ttcaaggagg tcgaatttgc cctgccggtc    4920
gagctgaccc tcgaccagca gaaggcgctg gcgtccgagt tcgcccagca cctgaccggt    4980
gccgagcgcc tgccgtatac gctggccatc catgccggtg gcggcgagaa cccgcactgc    5040
cacctgatga tctccgagcg gatcaatgac ggcatcgagc ggcccgccgc tcagtggttc    5100
aagcggtaca acggcaagac cccggagaag ggcgggcac agaagaccga agcgctcaag    5160
cccaaggcat ggcttgagca gacccgcgag catgggccg accatgccaa ccgggcatta    5220
gagcgggctg gccacgacgc ccgcattgac cacagaacac ttgaggcgca gggcatcgag    5280
cgcctgcccg gtgttcacct ggggccgaac gtggtggaga tggaaggccg gggcatccgc    5340
```

```
accgaccggg cagacgtggc cctgaacatc gacaccgcca acgcccagat catcgactta    5400
caggaatacc gggaggcaat agaccatgaa cgcaatcgac agagtgaaga aatccagagg    5460
catcaacgag ttagcggagc agatcgaacc gctggcccag agcatggcga cactggccga    5520
cgaagcccgg caggtcatga gccagaccaa gcaggccagc gaggcgcagg cggcggagtg    5580
gctgaaagcc cagcgccaga caggggcggc atgggtggag ctggccaaag agttgcggga    5640
ggtagccgcc gaggtgagca gcgccgcgca gagcgcccgg agcgcgtcgc gggggtggca    5700
ctggaagcta tggctaaccg tgatgctggc ttccatgatg cctacggtgg tgctgctgat    5760
cgcatcgttg ctcttgctcg acctgacgcc actgacaacc gaggacggct cgatctggct    5820
gcgcttggtg gcccgatgaa gaacgacagg actttgcagg ccataggccg acagctcaag    5880
gccatgggct gtgagcgctt cgatatcggc gtcaggacg cacccaccgg ccagatgatg    5940
aaccgggaat ggtcagccgc cgaagtgctc cagaacacgc catggctcaa gcggatgaat    6000
gcccagggca atgacgtgta tatcaggccc gccgagcagg agcggcatgg tctggtgctg    6060
gtggacgacc tcagcgagtt tgacctggat gacatgaaag ccgagggccg ggagcctgcc    6120
ctggtagtgg aaaccagccc gaagaactat caggcatggg tcaaggtggc cgacgccgca    6180
ggcggtgaac ttcgggggca gattgcccgg acgctggcca gcgagtacga cgccgacccg    6240
gccagcgccg acagccgcca ctatggccgc ttggcgggct tcaccaaccg caaggacaag    6300
cacaccaccc gcgccggtta tcagccgtgg gtgctgctgc gtgaatccaa gggcaagacc    6360
gccaccgctg gcccggcgct ggtgcagcag gctggccagc agatcgagca ggcccagcgg    6420
cagcaggaga aggcccgcag gctggccagc ctcgaactgc ccgagcggca gcttagccgc    6480
caccggcgca cggcgctgga cgagtaccgc agcgagatgg ccgggctggt caagcgcttc    6540
ggtcatgacc tcagcaagtg cgactttatc gccgcgcaga gctggccag ccggggccgc    6600 agtgccgagg aaatcggcaa ggccatggcc gaggccagcc cagcgctggc agagcgcaag    6660
cccggccacg aagcggatta catcgagcgc accgtcagca aggtcatggg tctgcccagc    6720
gtccagcttg cgcgggccga gctggacacg gcaccggcac cccgccagcg aggcatggac    6780
aggggcgggc cagatttcag catgtagtgc ttgcgttggt actcacgcct gttatactat    6840
gagtactcac gcacagaagg gggttttatg gaatacgaaa aaagcgcttc agggtcggtc    6900
tacctgatca aaagtgacaa gggctattgg ttgcccggtg gctttggtta acgtcaaac    6960 aaggccgagg ctggccgctt ttcagtcgct gatatggcca gccttaacct tgacggctgc    7020
accttgtcct tgttccgcga agacaagcct ttcggccccg gcaagtttct cggtgactga    7080
tatgaaagac caaaggaca agcagaccgg cgacctgctg ccagccctg acgctgtacg    7140 ccaagcgcga tatgccgagc gcatgaaggc caaaggatg cgtcagcgca agttctggct    7200
gaccgacgac gaatacgagg cgctgcgcga gtgcctggaa gaactcagag cggcgcaggg    7260
cgggggtagt gaccccgcca gcgcctaacc accaactgcc tgcaaaggag gcaatcaatg    7320
gctacccata agcctatcaa tattctggag gcgttcgcag cagcgccgcc accgctggac    7380
tacgttttgc ccaacatggt ggccggtacg gtcggggcgc tggtgtcgcc cggtggtgcc    7440
ggtaaatcca tgctggccct gcaactggcc gcacagattg caggcgggcc ggatctgctg    7500
gaggtgggcg aactgcccac cggccccggtg atctacctgc ccgccgaaga cccgcccacc    7560
gccattcatc accgcctgca cgcccttggg gcgcacctca gcgccgagga acggcaagcc    7620
gtggctgacg gcctgctgat ccagccgctg atcggcagcc tgcccaacat catggccccg    7680
```

```
gagtggttcg acggcctcaa gcgcgccgcc gagggccgcc gcctgatggt gctggacacg   7740
ctgcgccggt tccacatcga ggaagaaaac gccagcggcc ccatggccca ggtcatcggt   7800
cgcatggagg ccatcgccgc cgataccggg tgctctatcg tgttcctgca ccatgccagc   7860
aagggcgcgg ccatgatggg cgcaggcgac cagcagcagg ccagccgggg cagctcggta   7920
ctggtcgata acatccgctg gcagtcctac ctgtcgagca tgaccagcgc cgaggccgag   7980
gaatggggtg tggacgacga ccagcgccgg ttcttcgtcc gcttcggtgt gagcaaggcc   8040
aactatggcg caccgttcgc tgatcggtgg ttcaggcggc atgacggcgg ggtgctcaag   8100
cccgccgtgc tggagaggca gcgcaagagc aaggggtgc cccgtggtga agcctaagaa    8160
caagcacagc ctcagccacg tccggcacga cccggcgcac tgtctggccc ccggcctgtt   8220
ccgtgccctc aagcggggcg agcgcaagcg cagcaagctg gacgtgacgt atgactacgg   8280
cgacggcaag cggatcgagt tcagcggccc ggagccgctg ggcgctgatg atctgcgcat   8340
cctgcaaggg ctggtggcca tggctgggcc taatggccta gtgcttggcc cggaacccaa   8400
gaccgaaggc ggacggcagc tccggctgtt cctggaaccc aagtgggagg ccgtcaccgc   8460
tgaatgccat gtggtcaaag gtagctatcg ggcgctggca aaggaaatcg ggcagaggt   8520
cgatagtggt ggggcgctca agcacataca ggactgcatc gagcgccttt ggaaggtatc   8580
catcatcgcc cagaatggcc gcaagcggca ggggtttcgg ctgctgtcgg agtacgccag   8640
cgacgaggcg gacgggcgcc tgtacgtggc cctgaacccc ttgatcgcgc aggccgtcat   8700
gggtggcggc cagcatgtgc gcatcagcat ggacgaggtg cgggcgctgg acagcgaaac   8760
cgcccgcctg ctgcaccagc ggctgtgtgg ctggatcgac cccggcaaaa ccggcaaggc   8820
ttccatagat accttgtgcg gctatgtctg gccgtcagag gccagtggtt cgaccatgcg   8880
caagcgccag aagcgggtgc gcgaggcgtt gccggagctg gtcgcgctgg gctggacggt   8940
aaccgagttc gcggcgggca agtacgacat caccccggcc aaggcggcag gctgaccccc   9000
cccactctat tgtaaacaag acatttttat cttttatatt caatggctta ttttcctgct   9060
aattggtaat accatgaaaa ataccatgct cagaaaaggc ttaacaatat tttgaaaaat   9120
tgcctactga gcgctgccgc acagctccat aggccgcttt cctggctttg cttccagatg   9180
tatgctcttc tgctcccgaa cgccagcaag acgtagccca gcgcgtcggc cagcttgcaa   9240
ttcgcgctaa cttacattaa ttgcgttgcg ctcactgccc gctttccagt cgggaaacct   9300
gtcgtgccag ctgcattaat gaatcggcca acgcgcgggg agaggcggtt tgcgtattgg   9360
gcgccagggt ggttttctt ttcaccagtg agacgggcaa cagctgattg cccttcaccg    9420
cctggccctg agagagttgc agcaagcggt ccacgtggtt gccccagca ggcgaaaatc    9480
ctgtttgatg gtggttaacg gcgggatata acatgagctg tcttcggtat cgtcgtatcc   9540
cactaccgag atatccgcac caacgcgcag cccggactcg gtaatggcgc gcattgcgcc   9600
cagcgccatc tgatcgttgg caaccagcat cgcagtggga acgatgccct cattcagcat   9660
ttgcatggtt tgttgaaaac cggacatggc actccagtcg ccttcccgtt ccgctatcgg   9720
ctgaatttga ttgcgagtga gatatttatg ccagccagcc agacgcagac gcgccgagac   9780
agaacttaat gggcccgcta acagcgcgat ttgctggtga cccaatgcga ccagatgctc   9840
cacgcccagt cgcgtaccgt cttcatggga gaaaataata ctgttgatgg gtgtctggtc   9900
agagacatca agaaataacg ccggaacatt agtgcaggca gcttccacag caatggcatc   9960
ctggtcatcc agcggatagt taatgatcag cccactgacg cgttgcgcga aagattgtg   10020
caccgccgct ttacaggctt cgacgccgct tcgttctacc atcgacacca ccacgctggc   10080
```

```
acccagttga tcggcgcgag atttaatcgc cgcgacaatt tgcgacggcg cgtgcagggc   10140
cagactggag gtggcaacgc caatcagcaa cgactgtttg cccgccagtt gttgtgccac   10200
gcggttggga atgtaattca gctccgccat cgccgcttcc acttttttccc gcgttttcgc   10260 agaaacgtgg ctggcctggt tcaccacgcg ggaaacggtc tgataagaga caccggcata   10320
ctctgcgaca tcgtataacg ttactggttt cacattcacc accctgaatt gactctcttc   10380
cgggcgctat catgccatac cgcgaaaggt tttgcaccat tcgatggtgt caacgtaaat   10440
gccgcttcgc cttcgcgcgc gaattgcaag ctgatccggg cttatcgact gcacggtgca   10500
ccaatgcttc tggcgtcagg cagccatcgg aagctgtggt atggctgtgc aggtcgtaaa   10560
tcactgcata attcgtgtcg ctcaaggcgc actcccgttc tggataatgt tttttgcgcc   10620
gacatcataa cggttctggc aaatattctg aaatgagctg ttgacaatta atcatcggct   10680
cgtataatgt gtggaattgt gagcggataa caatttcaca caggaaacag aattctaaag   10740
taagtgtaat tggcgggcct gctctgttat atgctgcatt accttatgca gatgaagtag   10800
ttgtttctcg catcgttaaa aggcatcgtg ttaattcaac agttcaatta gacgcaagtt   10860
ttcttgatga tataagcaag cgtgaaatgg ttgaaacgca ttggtataaa atagatgaag   10920
taacaaccct tacggaatca gtatataaat gaaacaatac caagatttaa ttaaagacat   10980
ttttgaaaat ggttatgaaa ccgatgatcg tacaggcaca ggaacaattg ctctgttcgg   11040
atctaaatta cgctgggatt taactaaagg ttttcctgcg gtaacaacta agaagctcgc   11100
ctggaaagct tgcattgctg agctaatatg gtttttatca ggaagcacaa atgtcaatga   11160
tttacgatta attcaacacg attcgttaat ccaaggcaaa acagtctggg atgaaaatta   11220
cgaaaatcaa gcaaaagatt taggatacca tagcggtgaa cttggtccaa tttatggaaa   11280
acagtggcgt gattttggtg gtgtagacca aattatagaa gttattgatc gtattaaaaa   11340
actgccaaat gataggcgtc aaattgtttc tgcatggaat ccagctgaac ttaaatatat   11400
ggcattaccg ccttgtcata tgttctatca gtttaatgtg cgtaatggct atttggattt   11460
gcagtggtat caacgctcag tagatgtttt cttgggtcta ccgtttaata ttgcgtcata   11520
tgctacgtta gttcatattg tagctaagat gtgtaatctt attccagggg atttgatatt   11580
ttctggtggt aatactcata tctatatgaa tcacgtagaa caatgtaaag aaattttgag   11640
gcgtgaacct aaagagcttt gtgagctggt aataagtggt ctaccttata aattccgata   11700
tctttctact aaagaacaat taaaatatgt tcttaaactt aggcctaaag atttcgttct   11760
taacaactat gtatcacacc ctcctattaa aggaaagatg gcggtgtaat tttattattg   11820
cgaggatata tgattttacg atttaaagat acttctggtg tagttctttt tacacttcct   11880
aacccaagcg agttagaagt tccaggacca gaacagccta ttaccattta tggtaaaaaa   11940
tactatactc ataaaatgac ctcgtgagta ttttgataat aaaaatttcc acagttaaaa   12000
cttcttctga ctgttactac gatattactg ttttaacgga aaacaatatg acgaattatt   12060
ccagcgtggg ccgtctatgc cgggtagtga ataaatataa atccgacttt gatgttaata   12120
ttcaccgcgg tacattttgg ggaaattacg tcggtaaaga tgctggcagc cgggaggctg   12180
ccattgaatt attcaaaaaa gatttatacg tcgaattaaa tccggagaaa taactaaagc   12240
acatttagag cctttacgtg gaatgaggct aggatgcaca tgtaaaccaa agccgtgtca   12300
tggtgatata atagctctca tagttaaccg attgtttaaa gacgattttc aagttgagga   12360
cttatgcaat taattaatgt tatcaaaagt agtggtgttt ctcagagctt tgacccacaa   12420
```

```
aaaattatta aagttttatc ttgggcagct gaaggaacat cagtagatcc ttatgaatta    12480
tatgaaaata ttaaatctta tctccgtgat ggaatgacaa ctgatgatat tcagactatt    12540
gtcattaagg ctgctgc                                                   12557
```

INHIBITION AND DIAGNOSTICS OF EMERGING TETRACYCLINE RESISTANCE ENZYMES

CROSS REFERENCE TO RELATED APPLICATIONS

This application claims the benefit of U.S. Provisional Application No. 62/354,404, filed Jun. 24, 2016, which is hereby incorporated by reference in its entirety.

GOVERNMENTAL RIGHTS

This invention was made with government support under AI123394 awarded by National Institutes of Health. The government has certain rights in the invention.

FIELD OF THE INVENTION

The present disclosure relates to methods for treating a bacterial infection in a subject.

BACKGROUND OF THE INVENTION

Tetracyclines are an important class of antibiotics in agriculture and the clinic; however, their efficacy is threatened by increasing resistance. Resistance to tetracyclines can occur through efflux, ribosomal protection, or enzymatic inactivation.

The tetracycline destructases are a recently-discovered family of tetracycline-inactivating flavoenzymes from pathogens and soil metagenomes with a high potential for broad dissemination. Tetracycline-inactivating enzymes represent an alarming emerging mechanism of antibiotic resistance to a crucial class of antibiotics (i.e., tetracyclines) that have been used for decades in the clinic, agriculture, and aquaculture. While tetracycline-resistant pathogens have canonically employed the mechanisms of drug efflux and target modification, enzymatic inactivation of tetracyclines appears to be on the rise in ESKAPE pathogens (*Enterococcus faecium, Staphylococcus aureus, Klebsiella pneumoniae, Acinetobacter baumannii, Pseudomonas aeruginosa,* and *Enterobacter* species).

What is needed, therefore, is tetracycline/tetracycline destructase inhibitor combination therapy to overcome resistance by enzyme inactivation.

SUMMARY OF THE INVENTION

One aspect of the present disclosure is directed to a method of treating a bacterial infection in a subject. The method comprises administering to a subject a therapeutically effective amount of a compound that binds to and inhibits a FAD-dependent flavoenzyme and a tetracycline, analog, derivative, or pharmaceutically acceptable salt thereof.

Another aspect of the present invention is directed to a method of treating a tetracycline bacterial infection in a subject. The method comprises administering to a subject a therapeutically effective amount of a compound that binds to and inhibits a FAD-dependent flavoenzyme and a tetracycline, analog, derivative, or pharmaceutically acceptable salt thereof.

An additional aspect of the present invention is directed a compound for binding to and inhibiting a FAD-dependent flavoenzyme. The compound is selected from the group consisting of aChlortetracycline, aIodotetracycline, aDemeclocycine, and combinations thereof.

Other aspects and iterations of the disclosure are described in more detail below.

BRIEF DESCRIPTION OF THE FIGURES

The application file contains at least one drawing executed in color. Copies of this patent application publication with color drawing(s) will be provided by the Office upon request and payment of the necessary fee.

(FIG. 4A) Chlortetracycline binds to Tet(50) in a ~180° rotated orientation relative to Tet(X)+chlortetracycline, with FAD IN (orange); a model of FAD OUT (grey) is overlaid. (FIG. 4B) The rotated orientation in the Tet(50)+chlortetracycline structure is supported by van der Waals contacts from Val-348 (cyan) and Ile371 (deep teal) of the two C-terminal α-helices in Tet(50) to the dimethylamine group of the A-ring of chlortetracycline. Additionally, Phe-95 from the flexible loop makes contacts with the dimethylamine group and closes off the substrate-binding site. (FIG. 4C) Chlortetracycline binds Tet(X) with the D-ring distal to FAD. The substrate-binding site is widely exposed to bulk solvent. (FIG. 4D) Met-375 from the first C-terminal α-helix in Tet(X) (cyan) makes van der Waals contacts to the D-ring of chlortetracycline. A second C-terminal helix (red dashed circle, colored in deep teal) does not exist in Tet(X), and substrate can potentially enter from various possible directions. (FIG. 4E) Surface representation of Tet(50)+chlortetracycline monomer A. (FIG. 4F) Surface representation of Tet(50)+chlortetracycline monomer B. (FIG. 4G) In Tet(50)+chlortetracycline monomer A, FAD is IN, the loop is closed, and no chlortetracycline is bound. (FIG. 4H) In Tet(50)+chlortetracycline monomer B, FAD is IN, the loop is closed, and chlortetracycline is bound. (FIG. 4I) While the substrate-loading channel is open in Tet(50) monomer B, with FAD OUT, in the absence of chlortetracycline (grey), the flexible loop containing Phe-95 closes over the channel in Tet(50)+chlortetracycline monomer B, with FAD now IN.

(FIG. 5A) The $F_o-F_c$ map (contoured at 2.0σ) before modeling of chlortetracycline. (FIG. 5B) The $2F_o-F_c$ map (contoured at 1.0σ) after modeling of chlortetracycline. (FIG. 5C) Rotated view of the $F_o-F_c$ map (contoured at 2.0σ) before modeling of chlortetracycline. (FIG. 5D) Rotated view of the $2F_o-F_c$ map (contoured at 1.0σ) after modeling of chlortetracycline.

FIG. 6A, FIG. 6B, FIG. 6C, FIG. 6D, and FIG. 64E show that chlortetracycline is degraded by tetracycline destructases despite the unusual binding mode. (FIG. 6A) HPLC chromatograms show the time and enzyme dependent consumption of chlortetracycline. (FIG. 6B) High-resolution MS-MS analysis of the tetracycline destructase reaction with chlortetracycline supports clean conversion to the m/z 467 oxidation product. MS-MS spectrum of the m/z 467 ion from the Tet(55) reaction with proposed fragmentation pathway. (FIG. 6C, FIG. 6D, and FIG. 6E) The closest reactive carbons to C4a of the FAD cofactor are C3 (FIG. 6C) and C1 (FIG. 6D) of the chlortetracycline A ring, both of which are closer than C11a (FIG. 6E), the hydroxylation site observed in Tet(X) mediated chlortetracycline degradation.

(FIG. 7A) LC-MS chromatograms taken after 10 minutes of the chlortetracycline no-enzyme control reaction. UV-Vis chromatograms show absorbance at 260 nm. The TIC (FIG. 7C) and EIC (FIG. 7E and FIG. 7G) chromatograms show that only chlortetracycline (m/z for [M+H]+=479; retention time=8.1 minutes) is present in the reaction mixture. (FIG. 7B) LC-MS chromatograms taken after 10 minutes of the chlortetracycline reaction with Tet(55). The TIC (FIG. 7D) and EIC (FIG. 7F and FIG. 7H) chromatograms show that the majority of the chlortetracycline (m/z for [M+H]+=479; retention time=8.1 minutes) was converted to the oxidation product (m/z for [M+H]+=467; retention time=8.3 minutes).

(FIG. 8A) MS spectrum of no enzyme control; HRMS (ESI) calculated for $C_{22}H_{24}ClN_2O_8$+(chlortetracycline): 479.1216 [(M+H)+], observed 479.1232. (FIG. 8B) MS spectrum of chlortetracycline after reaction with Tet(50). (FIG. 8C) MS spectrum of chlortetracycline after reaction with Tet(55). (FIG. 8D) MS spectrum of chlortetracycline after reaction with Tet(56). (FIG. 8E) Two proposed mechanisms for degradation of chlortetracycline, consistent with MS and crystallographic data. Addition of the C4a flavin peroxide to C3 generates intermediate 1, which can undergo epoxide formation to give an equilibrating mixture of intermediates 2 and 3. Intermediate 3 can also be generated via intermediate 4 arising from direct attack of the C4a flavin peroxide on carbonyl C1. Intermediate 3 can rearrange to cycloheptanone intermediate 5. Fragmentation will give intermediate 6 via loss of carbon monoxide followed by ring contraction resulting in formation of product 7 with m/z 467 for [M+H]+.

(FIG. 9A) Anhydrotetracycline binds the active site of Tet(50) and traps the FAD cofactor in the unproductive OUT conformation (orange) in monomer B. The IN conformation of FAD from monomer A is superimposed in grey for comparison, and sterically clashes with the D-ring hydroxyl of anhydrotetracycline. (FIG. 9B) Surface representation of Tet(50)+anhydrotetracycline reveals that the substrate-loading channel remains open, which corresponds to FAD locked in the OUT conformation. (FIG. 9C) In Tet(50)+anhydrotetracycline monomer B, FAD is OUT, the loop is open, and anhydrotetracycline is bound (not shown: in monomer A, FAD is IN, the loop is closed, no anhydrotetracycline is bound). (FIG. 9D) Residue Thr-207 in Tet(50) makes van der Waals interactions with the planar 6-methyl group of anhydrotetracycline (aTC) (yellow) in the bound orientation, but would sterically clash with the 6-methyl and 6-hydroxyl groups that branch from the C ring of tetracycline or chlortetracycline if bound in a flipped orientation.

(FIG. 10A) The $F_o-F_c$ map (contoured at 2.0σ) before modeling of anhydrotetracycline. (FIG. 10B) The $2F_o-F_c$ map (contoured at 1.0σ) after modeling of anhydrotetracycline. (FIG. 10C) Rotated view of the $F_o-F_c$ map (contoured at 2.0σ) before modeling of anhydrotetracycline. (FIG. 10D) Rotated view of the $2F_o-F_c$ map (contoured at 1.0σ) after modeling of anhydrotetracycline.

FIG. 11A, FIG. 11B, and FIG. 11C depict superimposition images of tetracycline compounds in substrate-bound structures. (FIG. 11A) Superimposition of the Tet(50)+chlortetracycline (yellow) and Tet(X)+chlortetracycline (cyan) structures. (FIG. 11B) Superimposition of the Tet(50)+chlortetracycline (yellow) and Tet(50)+anhydrotetracycline (magenta) structures. (FIG. 11C) Superimposition of the Tet (X)+chlortetracycline (cyan) and Tet(50)+ anhydrotetracycline (magenta) structures.

(FIG. 13A) Tetracycline (TC) is degraded by Tet(56) in vitro HPLC chromatograms show in vitro reactions with UV detection at 363 nm and separation on a C18 column. (FIG. 13B) TC degradation is attenuated by the addition of an excess of aTC. (FIG. 13C) Dose-dependent inhibition of Tet(50,51,56) activity by anhydrotetracycline. Velocity is determined by measuring tetracycline consumption via change in absorbance at 400 nm. Data are represented as mean±s.d. of three technical replicates. FIG. 13D) Dose-response curve showing effect of aTC on sensitivity of Tet(56)-expressing $E. coli$ to TC in liquid culture. Data are represented as mean±s.e.m. of three technical replicates. (FIG. 13E) TC and aTC synergistically inhibit growth of $E. coli$ expressing Tet(56), FICI=0.1875. Points show minimum inhibitory concentrations of two drugs in combination. Dashed line indicates the theoretical concentration of additive drug interaction. Data represented as mean±s.e.m. of three technical replicates.

(FIG. 16A) Substrate (e.g., chlortetracycline) can enter and bind the active site of a tetracycline destructase, resulting in a conformational switch from FAD OUT (grey) to FAD IN (orange) and closure of the substrate site. (FIG. 16B) A mechanistic inhibitor (e.g., anhydrotetracycline) enters and binds the active site, but sterically prevents the FAD cofactor from switching from the OUT to IN conformation and thereby preventing catalysis. Further, it can act synergistically to competitively prevent substrate from binding.

DETAILED DESCRIPTION OF THE INVENTION

Figure 1:
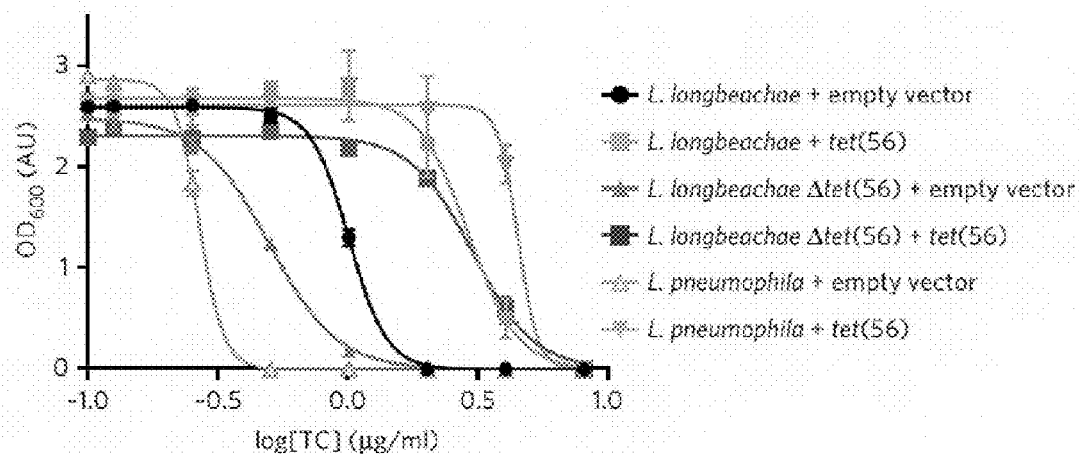
FIG. 1 depicts a dose-response curve showing the effect of tetracycline on growth of *Legionella* strains. Deletion of tet(56) from *L. longbeachae* causes an increase in tetracycline sensitivity. Complementation with a plasmid containing the tet(56) insert rescues the tetracycline resistance phenotype comp

Provided herein are methods for treating a bacterial infection in a subject. Suitable compositions and methods for treating a bacterial infection in a subject are detailed below.

(I) Compositions for Treating a Bacterial Infection

One aspect of the present disclosure encompasses a composition for treating a bacterial infection in a subject. In an embodiment, the composition may comprise a compound that binds and inhibits a FAD-dependent flavoenzyme and a tetracycline, a derivate, an analog, or pharmaceutical acceptable salt thereof.

(a) FAD-Dependent Flavoenzyme Binding Compounds

In an embodiment, the composition comprises a compound that binds to and inhibits a FAD-dependent flavoenzyme.

In some embodiments, the compound binds to a tetracycline destructase and locks the flavin adenine dinucleotide (FAD) cofactor in an inactive OUT conformation, thereby preventing the enzyme transition to the FAD IN conformation for catalysis. Further, this binding mode keeps the substrate-loading channel open and locks the isoalloxazine moiety of FAD away from the substrate-binding site and sterically blocks the transition to the FAD IN conformation for catalysis.

In some embodiments, the FAD-dependent flavoenzyme may be a tetracycline destructase enzyme. Suitable compounds that bind to FAD-dependent flavoenzymes include, without limit, anhydrotetracycline, aChlortetracycline, aIodotetracycline, aDemeclocycine, or pharmaceutical acceptable salts thereof. In an exemplary embodiment, the compound that binds to and inhibits a FAD-dependent flavoenzyme may be anhydrotetracycline, aChlortetracycline, aIodotetracycline, aDemeclocycine, and combinations thereof. In another exemplary embodiment, the compound that binds to and inhibits a FAD-dependent flavoenzyme may be anhydrotetracycline.

Pharmaceutical acceptable salts of a compound that binds to and inhibits a FAD-dependent flavoenzyme include, without limit, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like.

In an embodiment, the amount of a compound that binds a FAD-dependent flavoenzyme within the composition may and will vary depending on the identity and severity of the bacterial infection in a subject. In some embodiments, the amount of a tetracycline in the composition may be from about 0.05 wt. % to about 1 wt. %. In other embodiments, the amount of a tetracycline in the composition may be about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.55 wt. %, about 0.6 wt. %, about 0.75 wt. %, about 0.8 wt. %, about 0.85 wt. %, about 0.9 wt. %, or about 1 wt. %.

(b) Tetracyclines

In an embodiment, the composition comprises a tetracycline, derivate, analog, or pharmaceutical acceptable salt thereof. Tetracyclines are broad-spectrum antibiotics belonging to a subclass of polyketides having an octahydrotetracene-2-carboxamide skeleton. Suitable tetracyclines include, without limit, tetracycline, chlorotetracycline, demecocylcne, doxycycline, epi-tetracycline, epi-anhydrotetracycline, lymecycline, meclocycline, metacycline, methacycline, minocycline, oxytetracyline, tigecycline, a derivative, an analog, or pharmaceutically acceptable salt thereof. In an exemplary embodiment, the tetracycline may comprise tetracycline.

Pharmaceutical acceptable salts of tetracyclines include, without limit, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like.

In an embodiment, the amount of a tetracycline derivative, analog, or pharmaceutically acceptable salt thereof within the composition may and will vary depending on the identity and severity of the bacterial infection in a subject. In some embodiments, the amount of a tetracycline in the composition may be from about 0.05 wt. % to about 1 wt. %. In other embodiments, the amount of a tetracycline in the composition may be about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.55 wt. %, about 0.6 wt. %, about 0.75 wt. %, about 0.8 wt. %, about 0.85 wt. %, about 0.9 wt. %, or about 1 wt. %.

(c) Pharmaceutical Compositions

The present disclosure also provides pharmaceutical compositions. The pharmaceutical composition comprises a polynucleotide, polypeptide, vector or isolated cell of the invention which is detailed above, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline, or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate, or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(d) Dosage Forms

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

(II) Methods for Treating a Bacterial Infection

An additional aspect of the present disclosure encompasses methods for treating a bacterial infection in a subject. The method comprises administering to a subject a therapeutically effective amount of a compound that binds to and inhibits a FAD-dependent flavoenzyme and a tetracycline, analog, derivative, or pharmaceutically acceptable salt thereof.

(a) Bacterial Infection

In an embodiment, the bacterial infection may be tetracycline resistant.

In an embodiment, the bacterium may encode a tetracycline-inactivating enzyme or tetracycline destructase. In a further, embodiment, the bacterium may be mutated to overexpress a tetracycline-inactivating enzyme or tetracycline destructase as compared to the wild-type bacterium.

In an embodiment, the bacterial infection may be Pontiac Fever or Legionnaires' disease. In an embodiment, the bacterial infection may be caused by a bacterium. In an embodiment, the bacterium may be *Acinetobacter baumanii*, *Legionella* longbeachae. In a preferred embodiment, the bacterium may be *Legionella* longbeachae.

(b) Binding

In an embodiment, the compounds described in Section (I)(a) may bind to the active site of FAD-dependent flavoenzyme or tetracycline destructase. Suitable members of the tetracycline destructase family of enzymes include, without limit, Tet(49), Tet(50), Tet(51), Tet(55), Tet(56), Tet(X) (EC 1.14.13.8) and members of the flavin-dependent monooxygenases belonging to the oxiodoreductase subclasses 1.13 and 1.14.

In a preferred embodiment, the compounds described in Section (I)(a) bind to a tetracycline destructase and lock the flavin adenine dinucleotide (FAD) cofactor in an inactive OUT conformation, thereby preventing the enzyme transition to the FAD IN conformation for catalysis. Further, this binding mode keeps the substrate-loading channel open and locks the isoalloxazine moiety of FAD away from the substrate-binding site and sterically blocks the transition to the FAD IN conformation for catalysis.

In an embodiment, the compounds described in Section (I)(a) bind to a FAD-dependent flavoenzyme or tetracycline destructase at a different site than the compounds described in Section (I)(b).

(c) Administration

In certain aspects, a pharmacologically effective amount of a composition as described in Section (I) may be administered to a subject. Administration is performed using standard effective techniques, known to those skilled in the art.

A composition as described in Section (I) may be formulated and administered to a subject by several different means. For instance, a composition may generally be administered parenteraly, intraperitoneally, intravascularly, or intrapulmonarily in dosage unit formulations containing conventional nontoxic pharmaceutically acceptable adjuvants, carriers, excipients, and vehicles as desired. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

The amount of agent that is administered to the subject can and will vary depending upon the type of agent, the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

(d) Subject

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

(III) Compounds for Inhibiting a Fad-Dependent Flavoenzyme

In an additional aspect of the present disclosure encompasses compounds that bind and inhibit a FAD-dependent flavoenzyme. Non-limiting examples of such compounds include a compound selected from the group consisting of aChlortetracycline, aIodotetracycline, aDemeclocycine, and combinations thereof.

(a) FAD-Dependent Flavoenzyme Binding Compounds

In an embodiment, the composition comprises a compound that binds to and inhibits a FAD-dependent flavoenzyme.

In some embodiments, the compound binds to a tetracycline destructase and locks the flavin adenine dinucleotide (FAD) cofactor in an inactive OUT conformation, thereby preventing the enzyme transition to the FAD IN conformation for catalysis. Further, this binding mode keeps the substrate-loading channel open and locks the isoalloxazine moiety of FAD away from the substrate-binding site and sterically blocks the transition to the FAD IN conformation for catalysis.

In some embodiments, the FAD-dependent flavoenzyme may be a tetracycline destructase enzyme. In an exemplary embodiment, the compound that binds to and inhibits a FAD-dependent flavoenzyme may be aChlortetracycline, aIodotetracycline, aDemeclocycine, and combinations thereof.

Definitions

When introducing elements of the present disclosure or the preferred aspects(s) thereof, the articles "a," "an," "the" and "said" are intended to mean that there are one or more of the elements. The terms "comprising," "including" and "having" are intended to be inclusive and mean that there may be additional elements other than the listed elements.

As various changes could be made in the above-described compositions and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following abbreviations are used herein: EIC=extracted ion chromatogram and TIC=total ion chromatogram.

Introduction for Example 1

Antibiotics revolutionized the treatment of infectious diseases, enabling significant reductions in deaths due to infection over the past 80 years. However, the prolific anthropogenic use of these life-saving chemotherapeutics in the clinic and agriculture has also selected for a steady increase in antibiotic resistance in both benign and pathogenic bacteria.[1] Regrettably, increasing antibiotic resistance has been accompanied by a decrease in development and regulatory approval of new antibiotics,[2] threatening the end of the modern antibiotic era. The likely origin of virtually all clinical antibiotic resistance genes are environmental microbial communities, which harbor ancient and diverse resistomes.[3-9] Indeed, environmental reservoirs have been identified for a number of recently-emerged and rapidly-disseminating resistance genes representing urgent clinical threats (e.g., plasmid-borne and chromosomally-acquired carbapenem,[10] colistin,[11] and quinolone[12] resistance genes). This motivates the need to better understand resistance mechanisms of environmental origin before they are widespread in the clinic and ultimately guide new drug discovery and therapeutic strategies that mitigate emerging mechanisms of resistance.

Despite growing resistance, the tetracyclines remain among the most widely used antibiotics in clinical and agricultural settings.[13] Indeed, tetracyclines ranked in the top three antibiotics in both clinical prescriptions in the United States in 2010 (representing 15% of all antibiotic prescriptions) and in global sales for animal use in 2009 ($500 million in sales).[14] Furthermore, next-generation derivatives are currently fueling a tetracycline renaissance, with the 2005 clinical approval of tigecycline[15] and ongoing late-stage clinical trials of eravacycline and omadacycline[16,17] justifying urgent interrogation of emerging and novel tetracycline resistance mechanisms. Previously, tetracycline resistance was thought to occur almost exclusively by two mechanisms: ribosomal protection or antibiotic efflux.[13,18] However, an alternate mechanism—enzymatic inactivation—has been documented in benign and pathogenic bacteria, such as the enzyme Tet(X).[19-27] We recently identified a new family of tetracycline-inactivating enzymes through functional metagenomic selections for tetracycline resistance from grassland[18] and agricultural soils.[9] We showed that these nine proteins, Tet(47-55), were able to enzymatically inactivate tetracycline, resulting in 16-64 fold increases in minimum inhibitory concentration (MIC)[28] when expressed in E. coli.

Here, we pursued a multi-pronged structural, in vitro enzymatic, and bacterial phenotypic investigation of the emerging tetracycline destructases. We show that a recently identified tetracycline destructase confers tetracycline resistance to a known soil-derived human pathogen. We hypothesized that structural characteristics of tetracycline-inactivating enzymes would reveal useful information about their unique activity profiles and lead to the rational design of inhibitors, similar to the widely employed β-lactamase inhibitors.[29] Discerning the structural and mechanistic details of conformational or transitional states in target proteins has been crucial for the rational design of successful inhibitors in a number of cases, as exemplified by inhibitors of HIV-1 protease[30] and mechanistic inhibitors of glycosyltransferases that involve significant conformational movement in the active site.[31] Through structure-function analyses of four tetracycline destructases alone and in complex with tetracycline-class ligands, we present the molecular basis for unexpected structural dynamics in tetracycline destructases driven by antibiotic binding.

Example 1: Inhibition of Tetracycline Destructase

Tetracycline inactivation by Legionella longbeachae: The tetracycline destructase family was initially discovered by functional metagenomic selection for tetracycline resistance from soil samples.[9] We observed that the soil-derived human pathogen Legionella longbeachae, the causative agent of Pontiac Fever and Legionnaires' Disease[32,33] encodes a homolog to the tetracycline destructases, termed tet(56). Like the other tetracycline destructases, Tet(56) is able to inactivate tetracycline in vitro and expression of tet(56) in E. coli confers high-level tetracycline resistance.[28] To confirm that tet(56) is a functional resistance determinant in L. longbeachae, we deleted the gene and examined the strain for changes in drug sensitivity. Deletion of the chromosomally-encoded tet(56) resulted in an increase in tetracycline sensitivity to L. longbeachae (FIG. 1). Moreover, overexpression of tet(56) in the *L. longbeachae* Δtet(56) strain resulted in increased tetracycline resistance to levels even higher than the wild type *L. longbeachae* strain containing vector. Finally, expression of tet(56) in *L. pneumophila*, a *Legionella* strain lacking a tetracycline destructase homolog, also dramatically increased the level of tetracycline resistance of the strain. These results demonstrate that tetracycline destructases are already functional in a known human pathogen and their introduction into a related pathogen would lead to increased antibiotic resistance.

Structural Architecture and Dynamics of Tet(50,51,55, 56):

We began our structural analysis by solving the X-ray crystal structures of four tetracycline-inactivating enzymes: Tet(50), Tet(51), Tet(55), and Tet(56) (FIG. 2A and FIG. 3, panel a, panel b, panel c, panel d, and panel e). Although only sharing ~24% amino acid identity with the previously crystallized Tet(X) and requiring initial structure determination via experimental phasing (Table 1), Tet(50,51,55,56) and Tet(X) exhibit a similar overall architecture. Each possesses a flavin adenine dinucleotide (FAD)-binding Rossmann-type fold domain, a tetracycline-binding domain, and a C-terminal α-helix that bridges the two domains (FIG. 2A). Surprisingly, each of the new structures revealed an unexpected second α-helix at the C-terminus (FIG. 2A, FIG. 2B, and FIG. 2C) that is not present in Tet(X) (FIG. 2D) and could not be predicted based on their primary sequences. Comparisons to co-crystal structures of Tet(X) in complex with either chlortetracycline [PDB 2Y6R] or iodtetracycline [PDB 2Y6Q][27] reveal that this helical extension comes in close proximity to the tetracycline binding site (FIG. 2D), contributing to the formation of a substrate-loading channel. In the Tet(50) crystal structure, we observed two distinct monomers in the asymmetric unit. In Tet(50) monomer A, this substrate-loading channel is blocked by a flexible loop (FIG. 2B and FIG. 2E), whereas in Tet(50) monomer B, the channel is open, allowing tetracycline to access the substrate-binding site (FIG. 2C and FIG. 2F). The absence of the second α-helix in Tet(X) results in a widely exposed entrance to the substrate-binding site (FIG. 2D and FIG. 2G), which likely contributes to alternate substrate specificity of this enzyme.

TABLE 1

| Data Collection and Refinement Statistics | | | | |
|---|---|---|---|---|
| | Tet(55) Native | Tet(55) SeMet | Tet(50) | Tet(51) |
| Data collection | | | | |
| Space group | $P2_12_12$ | $P2_12_12$ | $P2_12_12_1$ | $P2_1$ |
| Cell dimensions | | | | |
| a, b, c (Å) | 64.74, 124.43, 45.73 | 65.14, 123.98, 45.75 | 50.94, 107.61, 152.48 | 83.49, 81.69, 127.31 |
| α, β, γ (°) | 90, 90, 90 | 90, 90, 90 | 90, 90, 90 | 90, 96.790, 90 |
| | | Peak | | |
| Wavelength | 1.018211 | 0.976289 | 1.000029 | 1.000028 |
| Resolution (Å) | 20-2.00 (2.10-2.00) | 20-1.90 (2.00-1.90) | 20-2.10 (2.20-2.10) | 20-1.85 (1.95-1.85) |
| $R_{meas}$ | 11.0% (96.4%) | 6.4% (59.7%) | 10.8% (71.6%) | 9.7% (79.7%) |
| I/σ/ | 16.14 (2.24) | 17.45 (2.57) | 15.07 (2.47) | 11.93 (1.90) |
| Completeness (%) | 99.7 (98.8) | 99.6 (98.0) | 98.1 (99.3) | 99.7 (99.6) |
| Redundancy | 7.17 (6.85) | 3.79 (3.59) | 5.70 (5.55) | 3.77 (3.67) |

TABLE 1-continued Data Collection and Refinement Statistics

| Refinement | | | |
|---|---|---|---|
| Resolution (Å) | 20-2.00 | 20-2.10 | 20-1.85 |
| No. reflections | 25,629 | 48,794 | 144,460 |
| $R_{work}/R_{free}$ | 19.25/23.86 | 22.81/26.23 | 16.67/19.99 |
| No. atoms | | | |
| Protein | 3,284 | 6,642 | 13,097 |
| Ligand/ion | 5 | 136 | 256 |
| Water | 187 | 376 | 942 |
| B-factors | | | |
| Protein | 30.24 | 29.76 | 27.82 |
| Ligand/ion | 28.36 | 35.73 | 17.93 |
| Water | 30.51 | 29.57 | 32.19 |
| R.m.s deviations | | | |
| Bond lengths (Å) | 0.005 | 0.003 | 0.007 |
| Bond angles (°) | 0.797 | 0.667 | 1.224 |

| | Tet(56) | Tet(50) + chlortetracycline | Tet(50) + anhydrotetracycline |
|---|---|---|---|
| Data collection | | | |
| Space group | $P2_12_12$ | $P2_12_12_1$ | $P2_12_12_1$ |
| Cell dimensions | | | |
| a, b, c (Å) | 76.49, 114.02, 94.81 | 51.10, 107.22, 152.63 | 50.99, 107.37, 152.79 |
| α, β, γ (°) | 90, 90, 90 | 90, 90, 90 | 90, 90, 90 |
| Wavelength | 1.000032 | 1.000031 | 1.000031 |
| Resolution (Å) | 20-3.30 (3.40-3.30) | 20-1.75 (1.85-1.75) | 20-2.25 (2.35-2.25) |
| $R_{meas}$ | 13.2% (119.2%) | 8.6% (86.5%) | 11.5% (68.7%) |
| I/σ/ | 10.76 (1.16) | 19.31 (2.35) | 13.57 (2.37) |
| Completeness (%) | 98.5 (94.0) | 98.7 (98.1) | 98.6 (92.7) |
| Redundancy | 3.60 (3.22) | 7.42 (7.37) | 4.93 (4.92) |
| Refinement | | | |
| Resolution (Å) | 20-3.30 | 20-1.75 | 20-2.25 |
| No. reflections | 12,803 | 84,325 | 39,793 |
| $R_{work}/R_{free}$ | 23.96/29.55 | 17.80/21.90 | 20.68/25.45 |
| No. atoms | | | |
| Protein | 5,819 | 6,733 | 6,698 |
| Ligand/ion | 116 | 181 | 182 |
| Water | 0 | 444 | 337 |
| B-factors | | | |
| Protein | 97.42 | 23.42 | 30.35 |
| Ligand/ion | 82.54 | 29.83 | 38.66 |
| Water | | 26.88 | 28.68 |
| R.m.s deviations | | | |
| Bond lengths (Å) | 0.002 | 0.011 | 0.003 |
| Bond angles (°) | 0.645 | 1.273 | 0.742 |

Figure 2A:
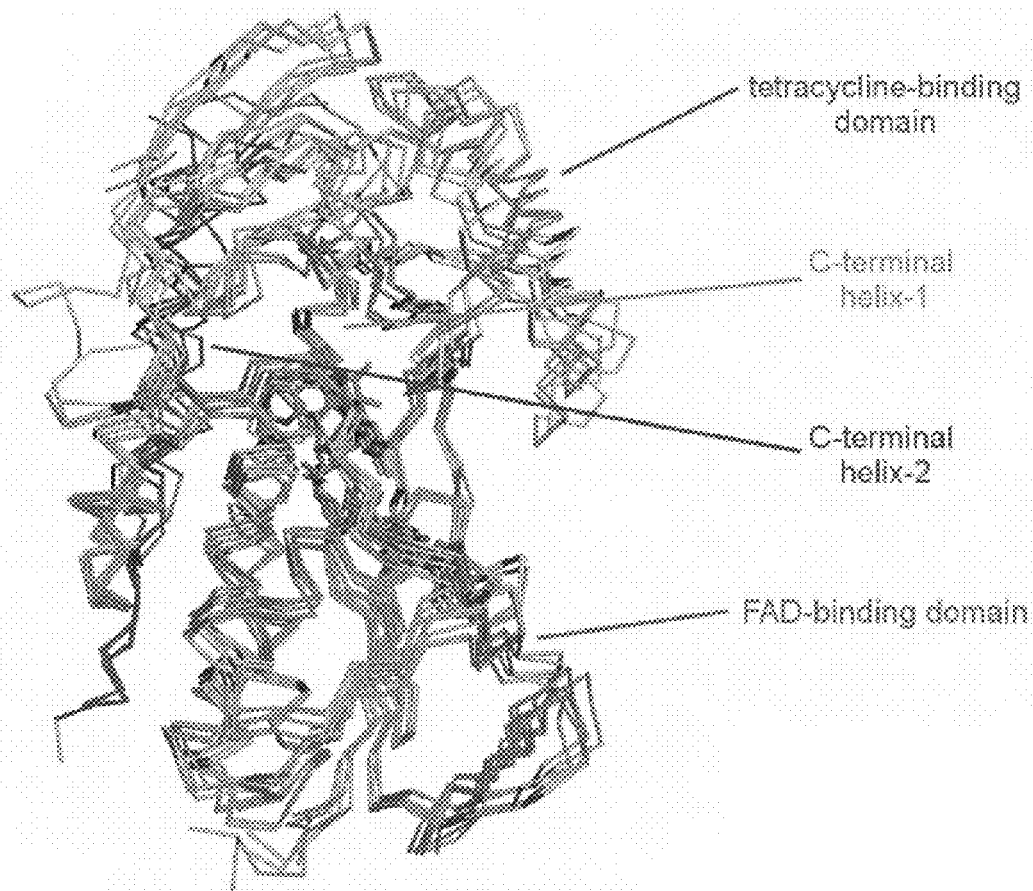
Figure 2B:
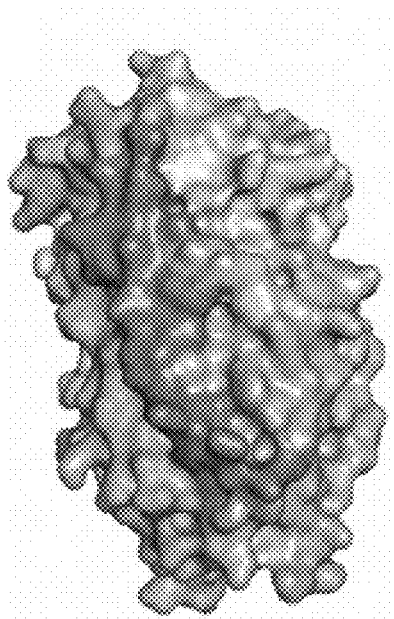
Figure 2C:
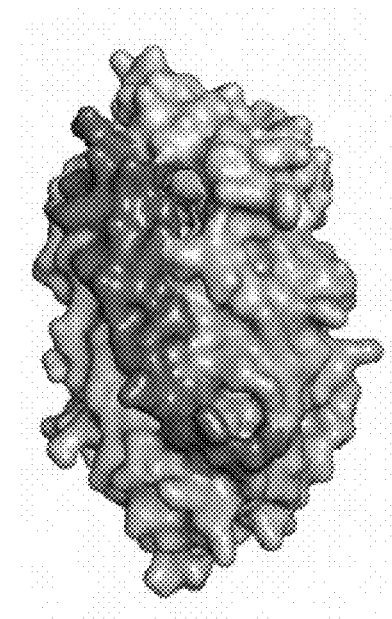
Figure 2D:
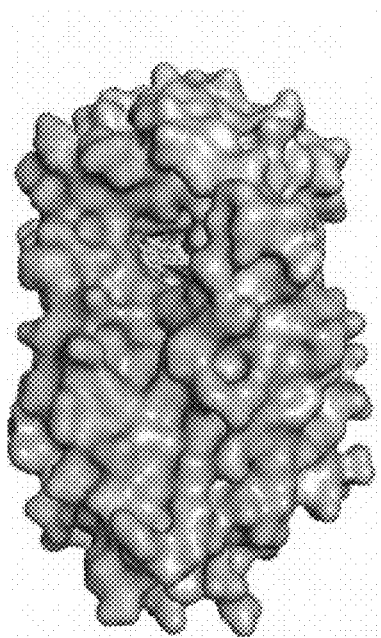
Figure 2E:
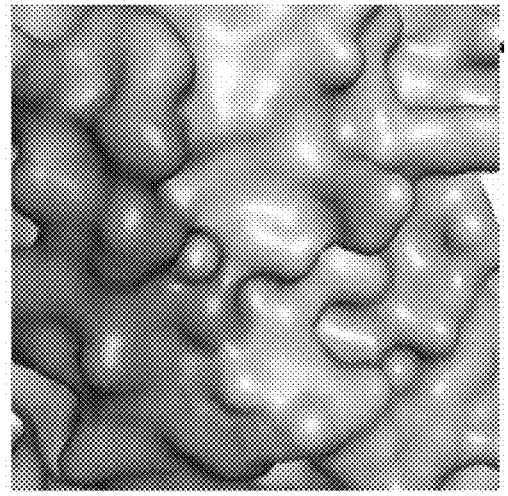
Figure 3:
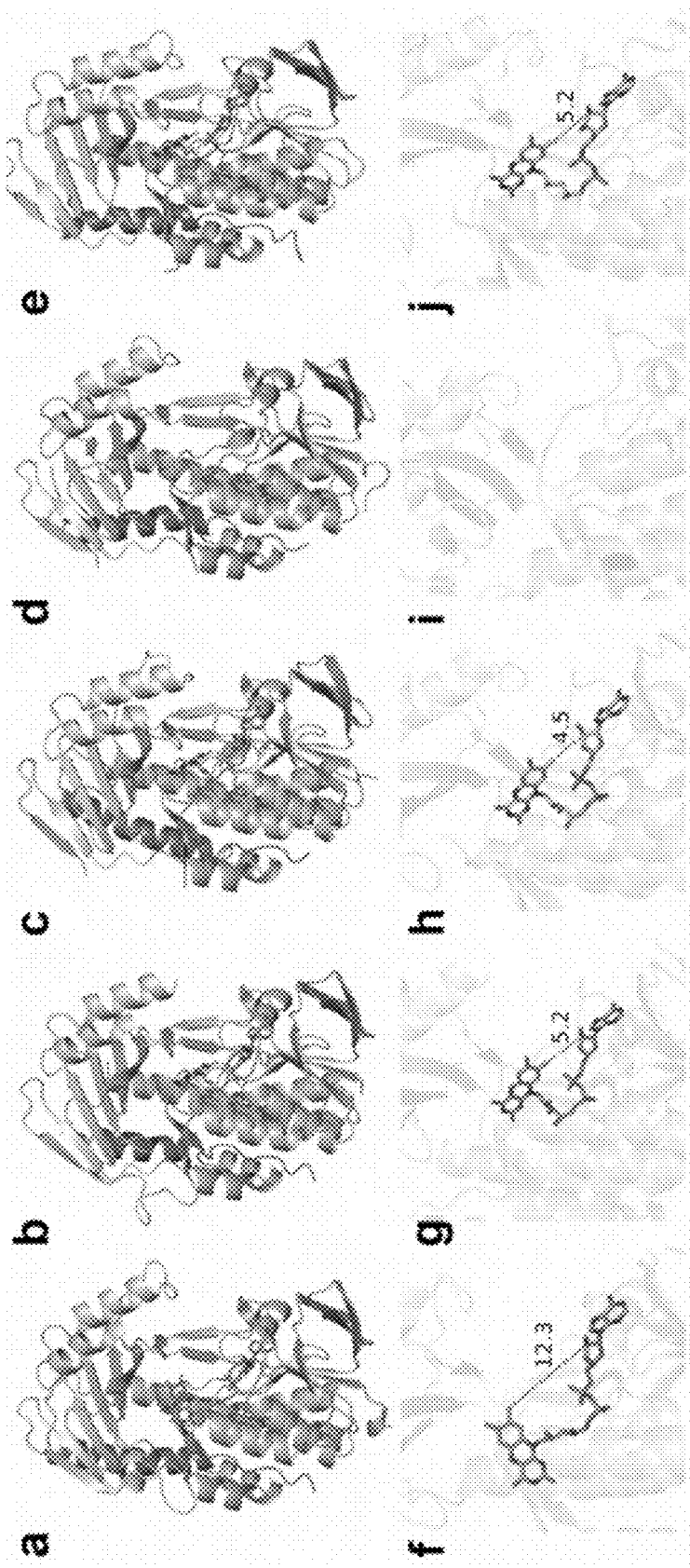

FAD Conformation Modulates Substrate Loading Channel:

Tetracycline destructases are flavoenzymes that utilize an FAD cofactor to degrade their substrate.[34,35] These enzymes bind FAD in two distinct conformations that are important for catalysis.[36] Both conformations are captured by the structures presented here (FIG. 3, panel f, panel g, panel h, panel l, and panel j). Tet(50) monomer A, which has a closed substrate-loading channel, bound FAD in an IN conformation (FIG. 2H). In this conformation the reactive isoalloxazine moiety of the FAD is stretched away from the adenosine moiety and into the substrate-binding site. This allows reaction with molecular oxygen to produce an FAD-hydroperoxide intermediate that is in close proximity to the tetracycline substrate (the C4a of FAD is ~5.9 Å away from the C11a substrate hydroxylation site in Tet(X)), allowing for hydroxylation and subsequent spontaneous degradation of the tetracycline substrate.[37] After catalysis, FAD flips away from the substrate-binding site, adopting the OUT conformation. Tet(50) monomer B, which has an open substrate-loading channel, binds FAD in an OUT conformation where the isoalloxazine moiety is bent towards the adenosine and away from the substrate-binding site (FIG. 2I). This conformational change allows for products to be released through the open channel and positions the oxidized FAD for reduction by NADPH in a distinct NADPH binding site during cofactor regeneration (FIG. 2J and FIG. 4A).[37] After reduction, FAD is poised to flip back to the IN conformation for the next round of catalysis upon substrate binding. Our observation of FAD in both IN and OUT conformations implies that FAD exists in an equilibrium between the two states in the absence of substrate binding.

Figure 4A:
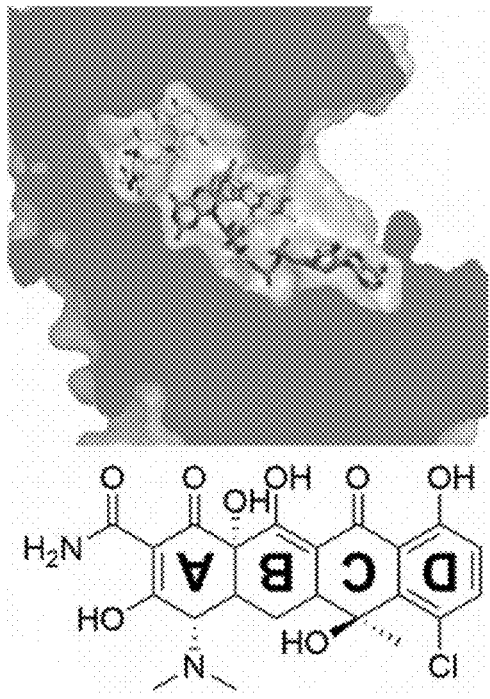
FIG. 4A, FIG. 4B, FIG. 4C, FIG. 4D, FIG. 4E, FIG. 4F, FIG. 4G, FIG. 4H, and FIG. 4I show that Tet(50)+chlortetracycline structure reveals an unexpected mode of binding that drives substrate loading channel closure and FAD conversion.
Figure 4B:
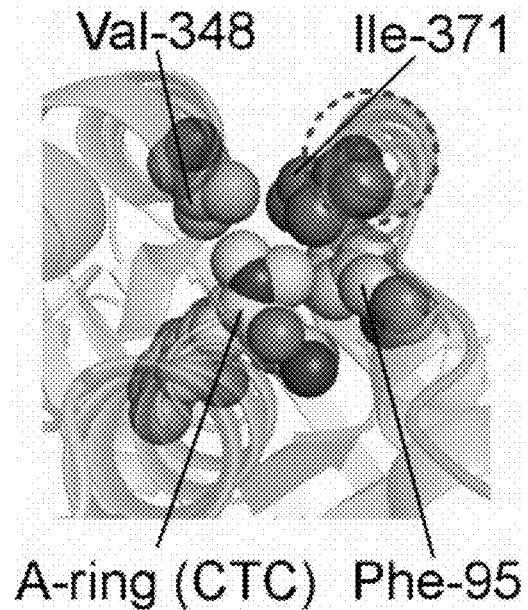
Figure 4C:
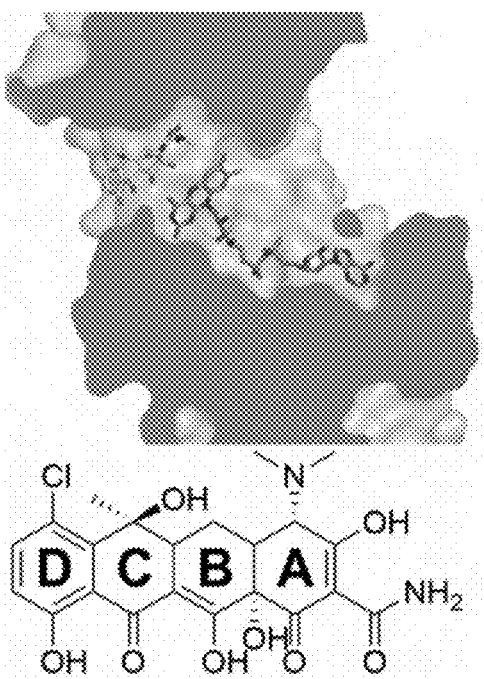
Figure 4D:
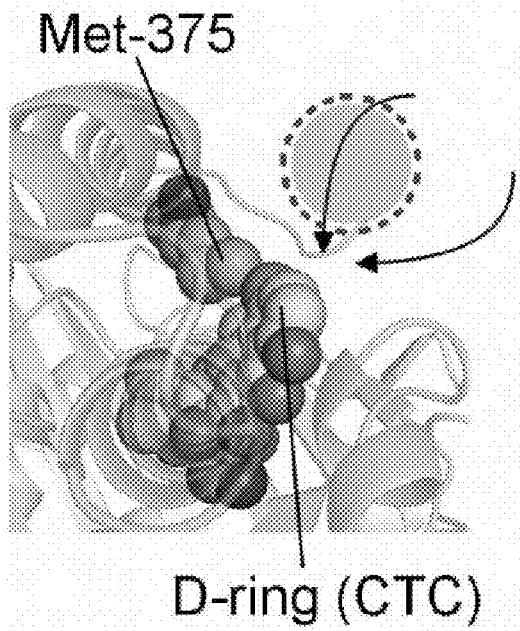
Figure 4E:
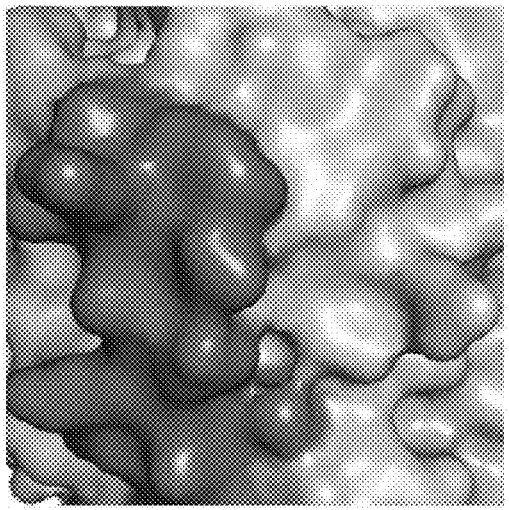
Figure 4F:
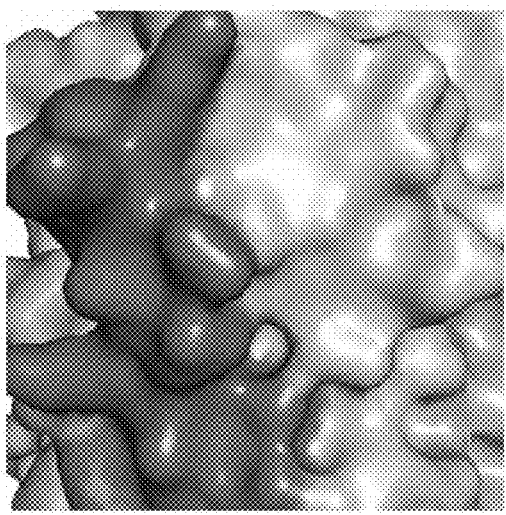
Figure 4G:
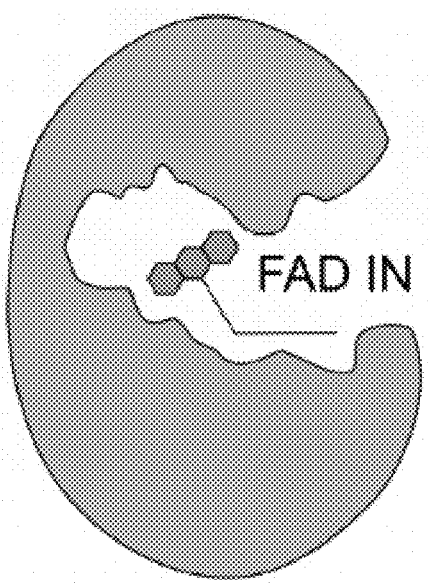

Substrate Binding Drives FAD and Channel Conversion:

Since accessibility of the substrate-loading channel appeared to be dependent on the conformation of FAD in the Tet(50) crystal structures, we soaked Tet(50) with various tetracycline compounds. Surprisingly, chlortetracycline binds to Tet(50) in a ~180° rotated orientation compared to the orientation in which chlortetracycline and other tetracycline substrates (e.g., iodtetracycline, minocycline, tigecycline) bind Tet(X)[27,38] (FIG. 4A, FIG. 4B, FIG. 4C, FIG. 4D, FIG. 5A, FIG. 5B, FIG. 5C, and FIG. 5D). Tetracycline compounds have a four-ring system (labeled A-D) (FIG. 4A and FIG. 4C), and have a distinctive three-dimensional architecture with a significant bend between rings A and B, allowing for unambiguous modeling into the electron density. In the Tet(X)+chlortetracycline structure, the chlortetracycline D-ring with the attached chlorine faces away from the substrate-binding site and towards bulk solvent (FIG. 4C and FIG. 4D). This places the C11a substrate hydroxylation site of ring C proximal to FAD. In the Tet(50)+chlortetracycline structure, the D-ring chlorine now faces FAD with the dimethylamine group of the A-ring making van der Waals contacts with Phe-95 from the flexible loop, Val-348 from the first C-terminal α-helix, and Ile-371 from the second C-terminal α-helix (FIG. 4A and FIG. 4B). Surprisingly, this new orientation positions C11a of chlortetracycline away from C4a of FAD.

Figure 4H:
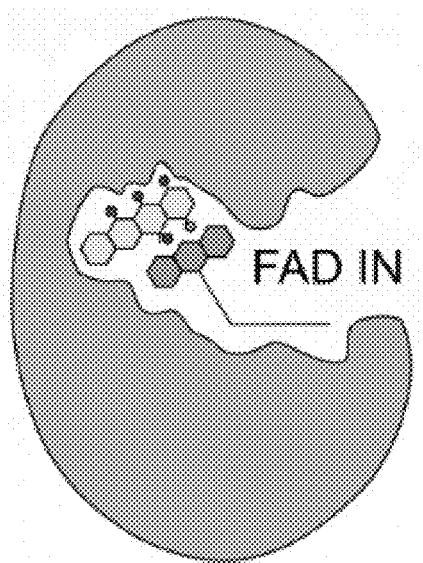
Figure 4I:
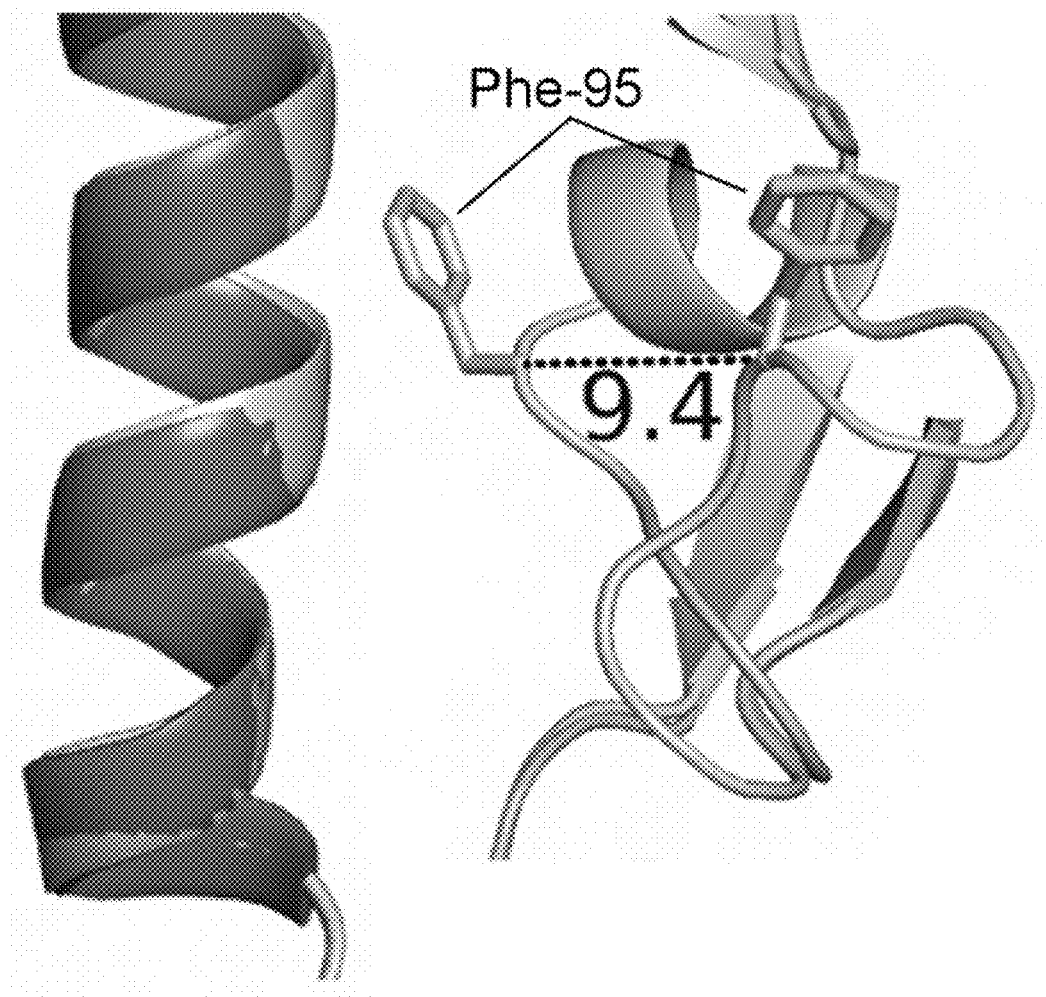
Figure 5A:
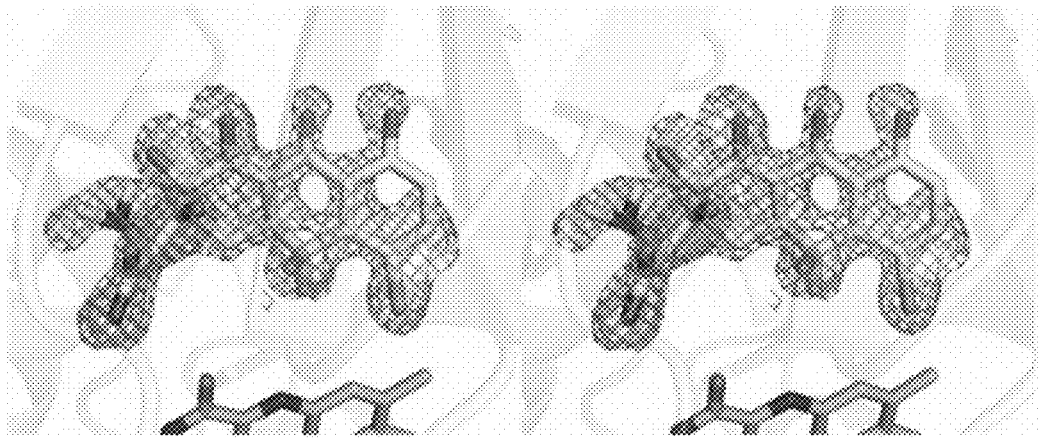
FIG. 5A, FIG. 5B, FIG. 5C, and FIG. 5D show that chlortetracycline has a distinctive three-dimensional architecture with a significant bend between rings A and B, allowing for unambiguous modeling into the electron density.
Figure 5B:
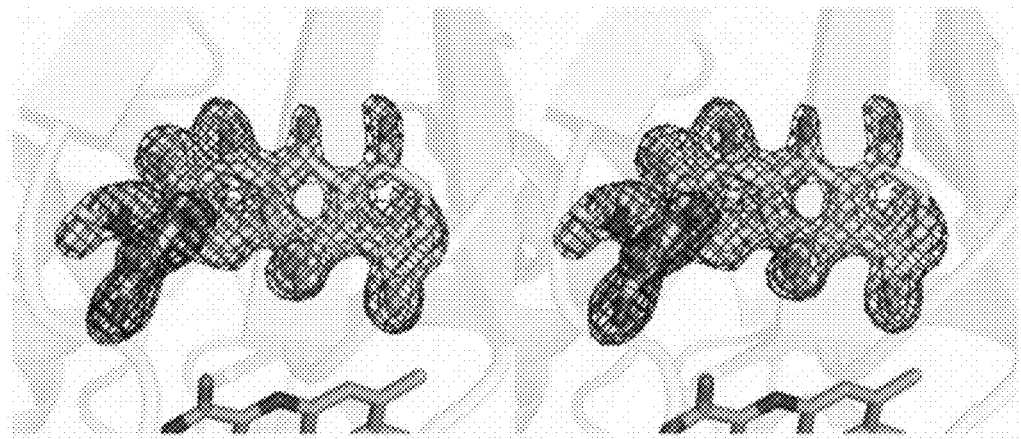
Figure 5C:
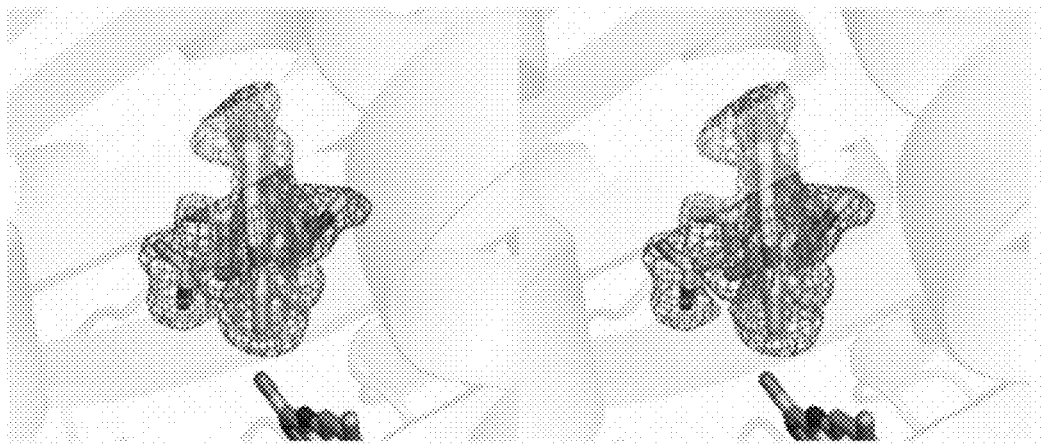
Figure 5D:
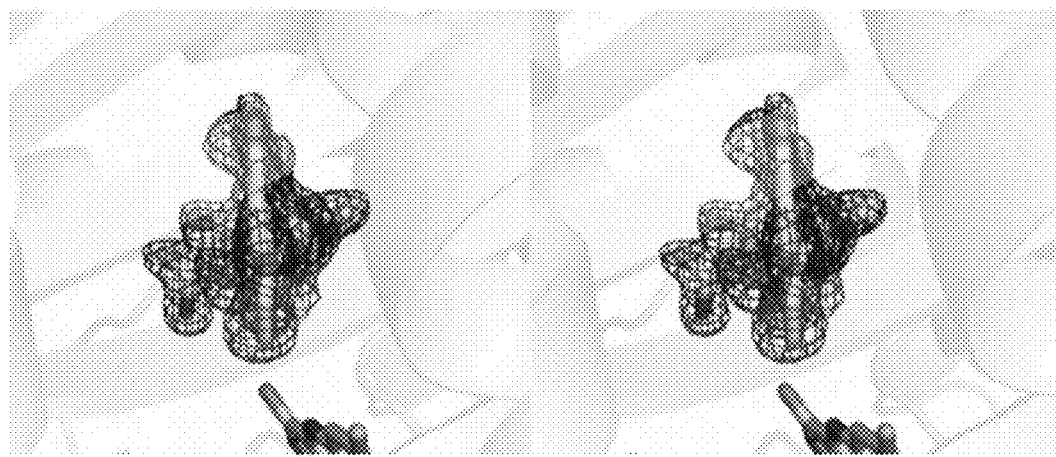

We observed a second notable characteristic when comparing the structures of Tet(50) in the presence or absence of chlortetracycline. In the absence of chlortetracycline, Tet(50) monomer A had FAD in an IN conformation with a closed channel (FIG. 2E, FIG. 2F, FIG. 2K, and FIG. 2I) and monomer B had FAD in an OUT conformation with an open channel (FIG. 2G, FIG. 2H, FIG. 2M, and FIG. 2N). However, in the presence of chlortetracycline, we only detected bound chlortetracycline in monomer B, which now had FAD in an IN conformation and a closed channel (FIG. 4E, FIG. 4F, FIG. 4G, and FIG. 4H). Thus, substrate binding to Tet(50) monomer B induced a conformational switch from FAD OUT to FAD IN and loop closure (FIG. 4H and FIG. 4I).

Figure 6A:
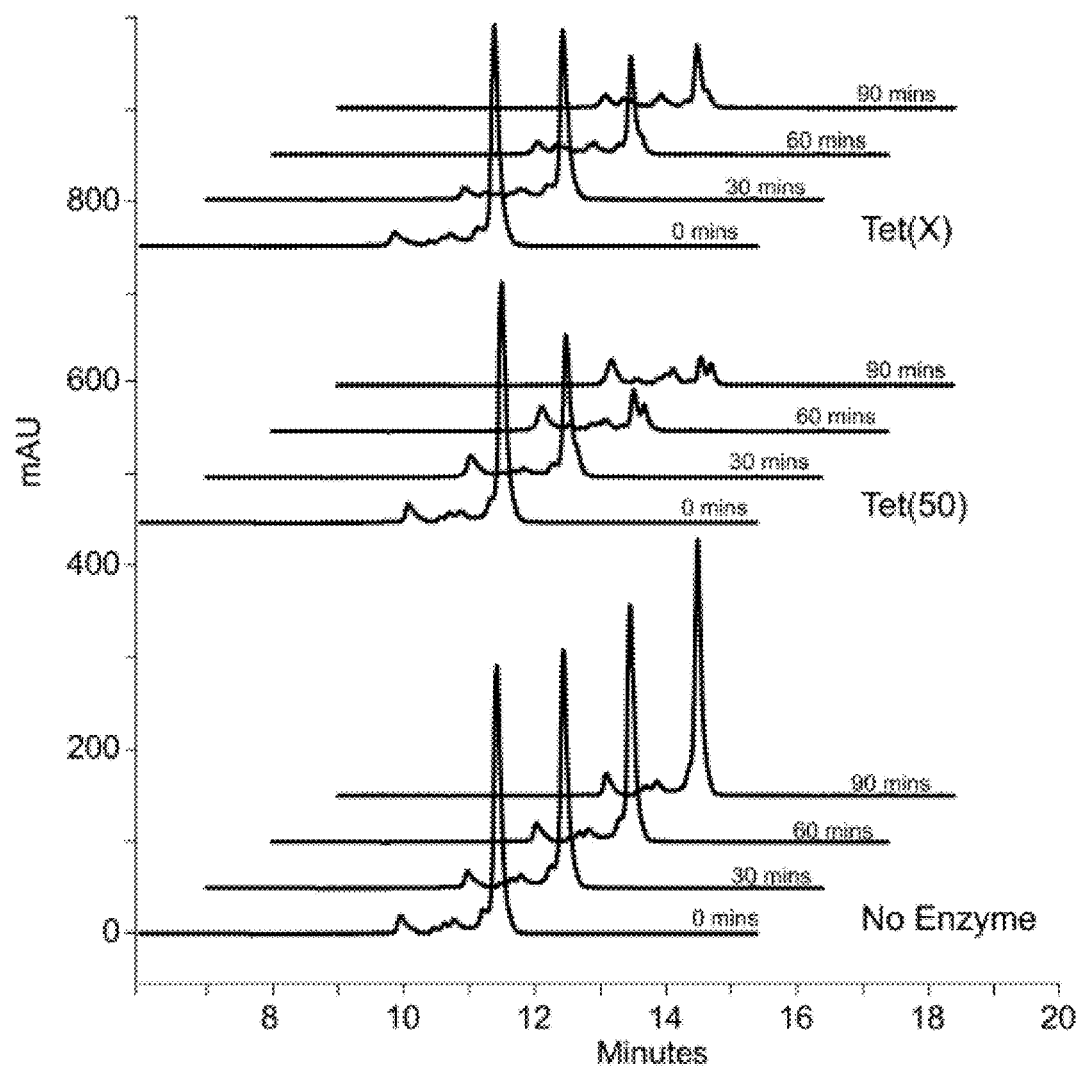

Tetracycline Destructases Degrade Chlortetracycline:

Due to the unanticipated orientation of chlortetracycline binding, we examined whether the tetracycline destructases could degrade chlortetracycline. Enzymatic reactions were analyzed at several time points by reverse-phase high-performance liquid chromatography (HPLC). We observed the time- and enzyme-dependent degradation of chlortetracycline by Tet(50) and Tet(X) (FIG. 6A). Kinetic parameters of enzymatic inactivation were determined by monitoring in vitro reaction progress using absorbance at 400 nm. The catalytic efficiency of Tet(50) was five times higher than that of Tet(X) (kcat/KM values of 0.55 and 0.11 μM-1 min-1, respectively) (Table 2). This increased efficiency is primarily due to increased turnover as the apparent KM values are comparable between Tet(50) (6.3±2.0 μM) and Tet(X) (7.9±2.7 μM) in spite of different substrate binding orientations. Tet(55) and Tet(56) also degraded chlortetracycline in vitro with 4-fold and 15-fold greater efficiency than Tet(X), respectively (Table 2). Furthermore, Tet(50,51,55, 56,X) each confer chlortetracycline resistance when expressed in E. coli at levels 16-32 fold greater than the vector-only control (Table 3). As a result, despite employing a distinct mode of substrate binding, Tet(50,51,55,56) are able to degrade chlortetracycline more efficiently than Tet(X).

TABLE 2

Kinetic parameters for Tet(50, 55, 56, X).
Data are represented as mean ± s.e.m of three technical replicates.

| | Tetracycline | | | Chlortetracycline | | |
|---|---|---|---|---|---|---|
| | $K_m$ (μM) | $k_{cat}$ (min$^{-1}$) | $k_{cat}/K_m$ (μM$^{-1}$ min$^{-1}$) | $K_m$ (μM) | $k_{cat}$ (min$^{-1}$) | $k_{cat}/K_m$ (μM$^{-1}$ min$^{-1}$) |
| Tet(50) | 17 ± 3.6 | 4.3 ± 0.23 | 0.25 | 6.3 ± 2.0 | 3.5 ± 0.25 | 0.55 |
| Tet(55) | 4.6 ± 1.6 | 1.8 ± 0.15 | 0.41 | 6.0 ± 1.3 | 2.9 ± 0.04 | 0.48 |
| Tet(56) | 7.7 ± 1.6 | 6.4 ± 0.31 | 0.83 | 3.7 ± 1.1 | 6.6 ± 0.39 | 1.8 |
| Tet(X) | 11 ± 2.6 | 0.67 ± 0.04 | 0.06 | 7.9 ± 2.7 | 0.90 ± 0.07 | 0.11 |

TABLE 3

Chlortetracycline minimum inhibitory concentrations (MIC)
for E. coli expressing tetracycline inactivating enzymes

| | MIC (μg/mL) |
|---|---|
| empty vector | 16 |
| tet(50) | 256 |
| tet(51) | 512 |
| tet(55) | 256 |
| tet(56) | 512 |
| tet(X) | 256 |

Figure 6B:
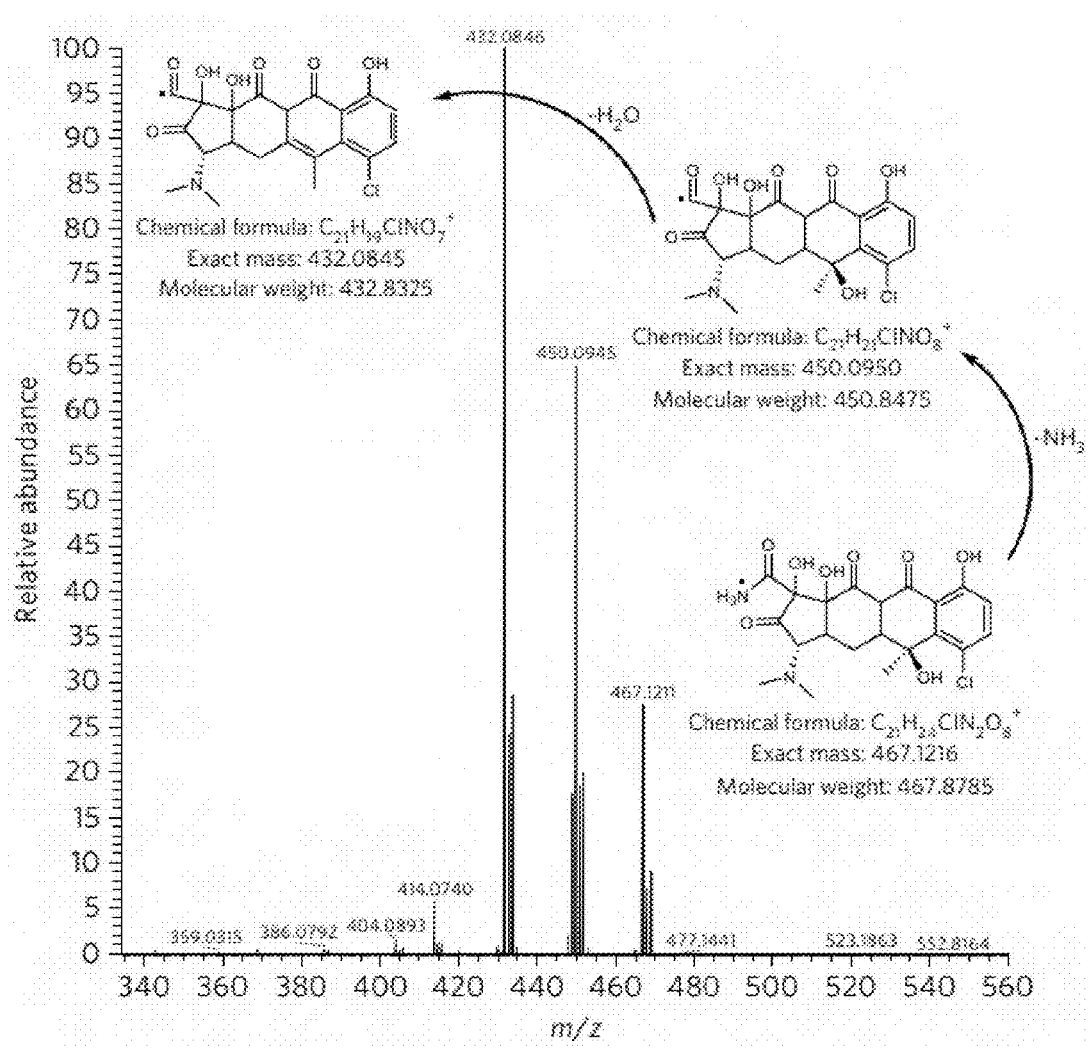

Tetracycline inactivation by Tet(X) occurs via catalysis at C11a resulting in a product of m/z 461.[28] Because chlortetracycline binds Tet(50) in an alternative mode that positions C11a far away from the reactive flavin peroxide moiety, we sought to characterize the degradation product to establish substrate hydroxylation. Enzymatic reactions were analyzed by liquid chromatography-mass spectrometry (FIG. 7 panel a and panel b), and found to convert chlortetracycline (m/z 479) to an oxidation product with an m/z of 467. This is in contrast to the m/z 461 monooxygenation product observed for tetracycline,[28] consistent with an alternate binding mode for chlortetracycline. To further characterize this product, reactions were subjected to high resolution mass spectrometry (FIG. 6B). Reactions with each enzyme assayed (Tet (50,55,56)) yielded a primary product with an exact m/z of 467.12 (FIG. 8A, FIG. 8B, FIG. 8C, and FIG. 8D).

Figure 6C:
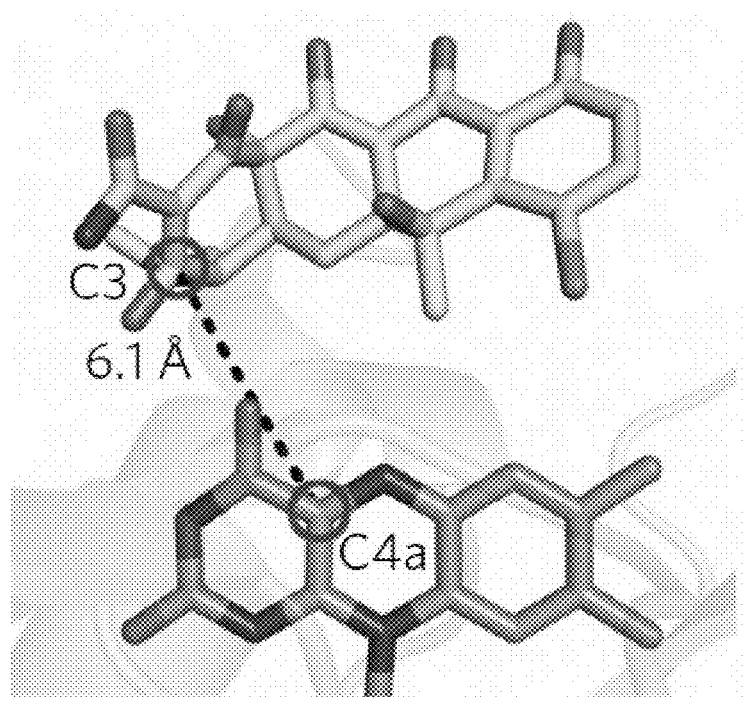
Figure 6D:
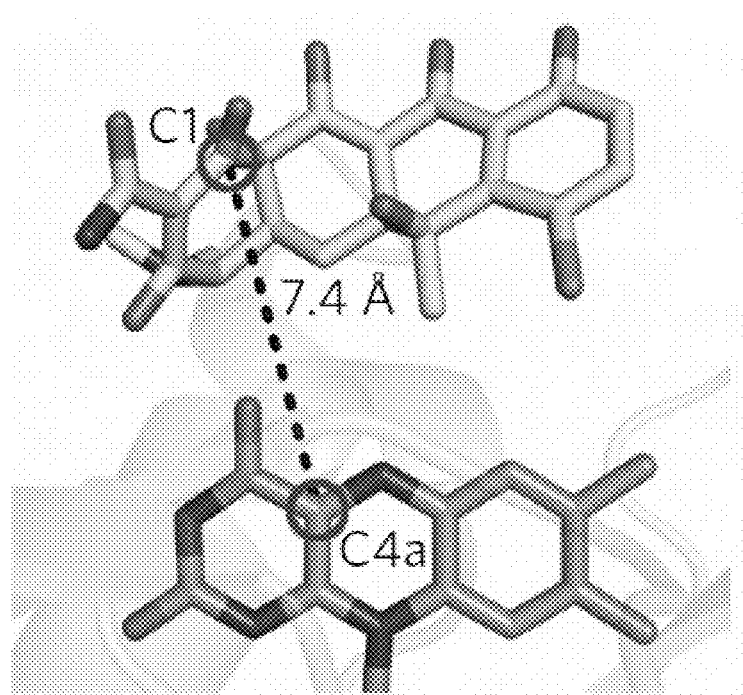
Figure 6E:
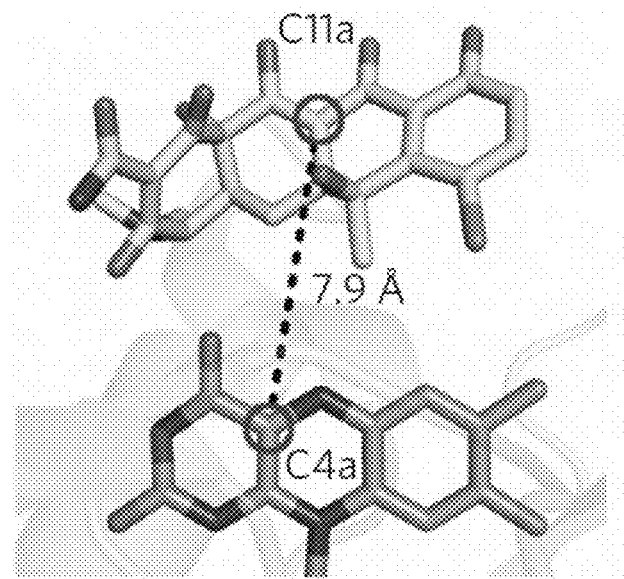
Figure 7A:
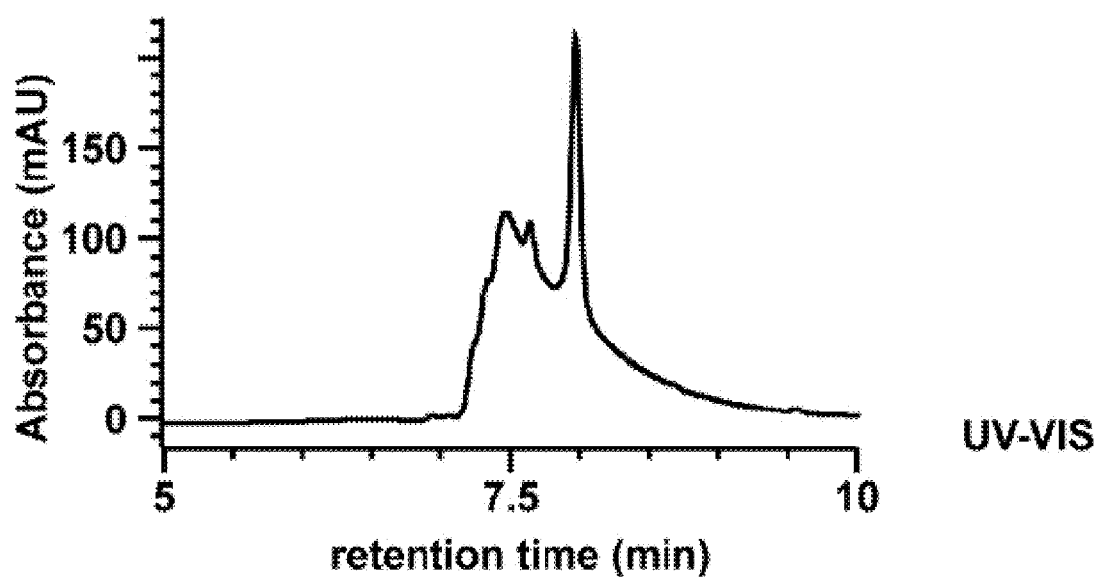
FIG. 7A, FIG. 7B, FIG. 7C, FIG. 7D, FIG. 7E, FIG. 7F, and FIG. 7G depict low-resolution LC-MS analysis of tetracycline destructase reaction with chlortetracycline shows clean conversion to the m/z 467 oxidation product.
Figure 7B:
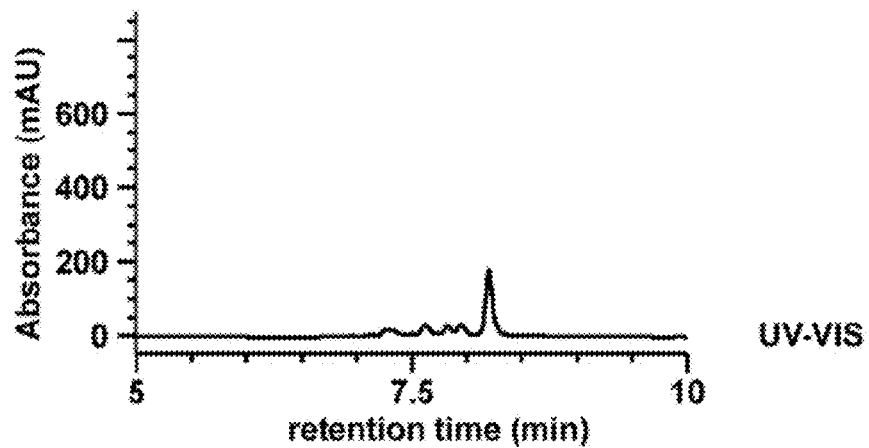
Figure 7C:
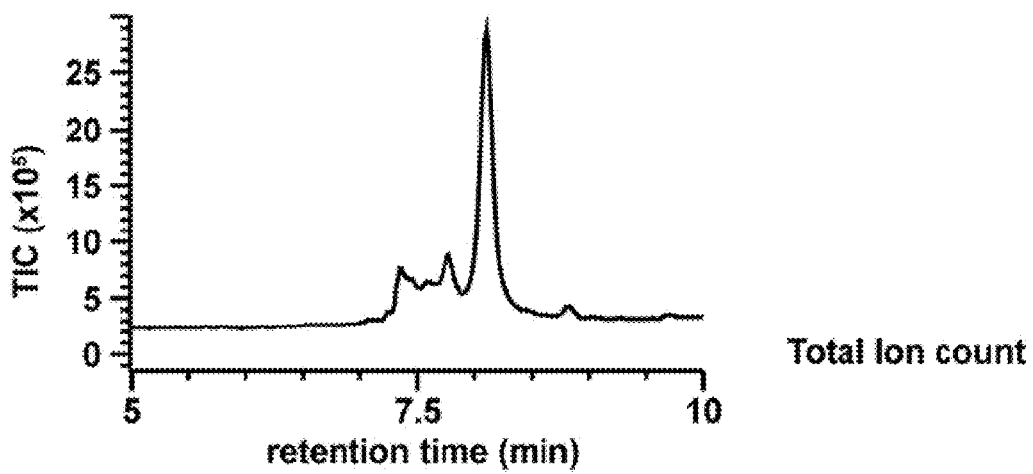
Figure 7D:
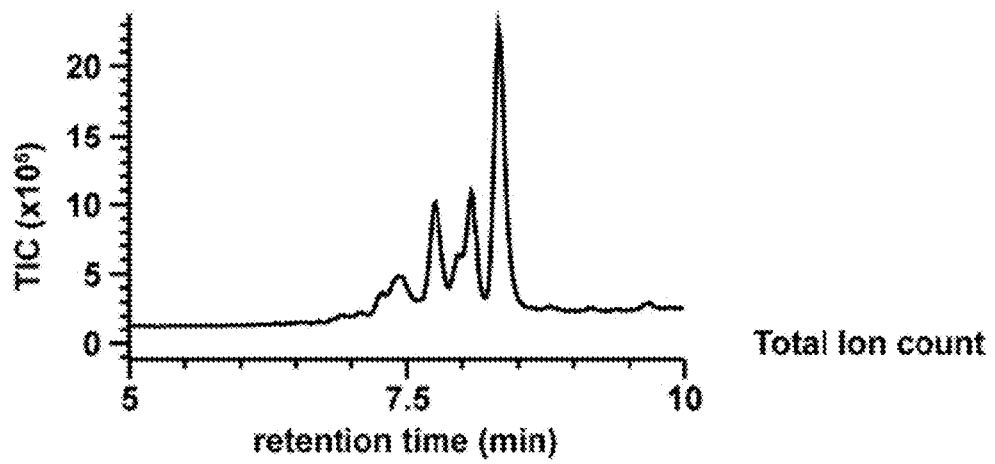
Figure 7E:
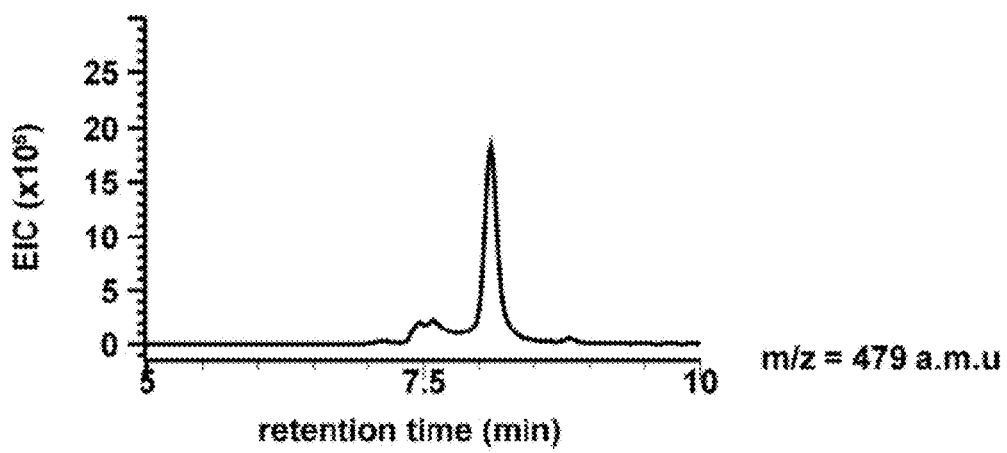
Figure 7F:
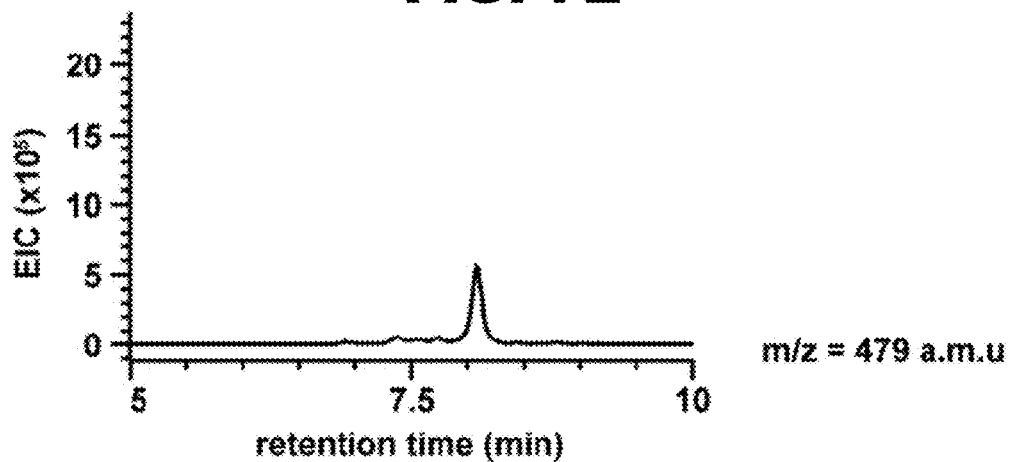
Figure 7G:
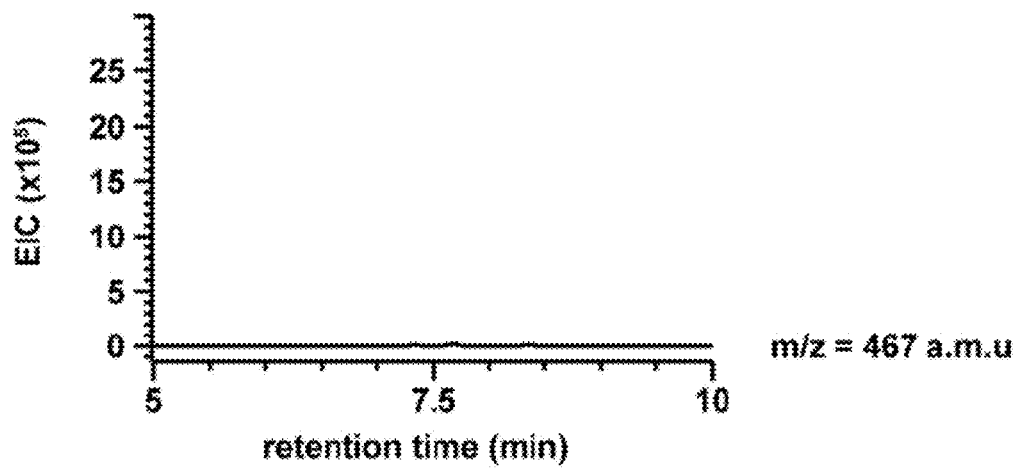
Figure 7H:
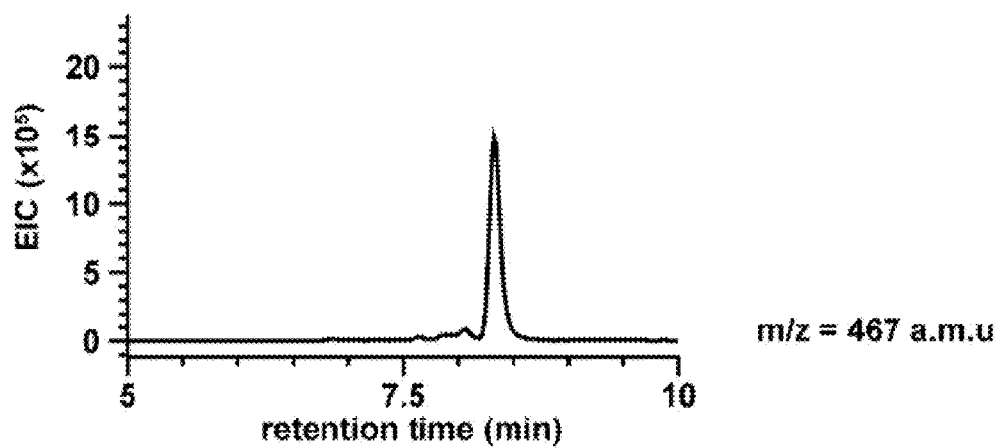
Figure 8A:
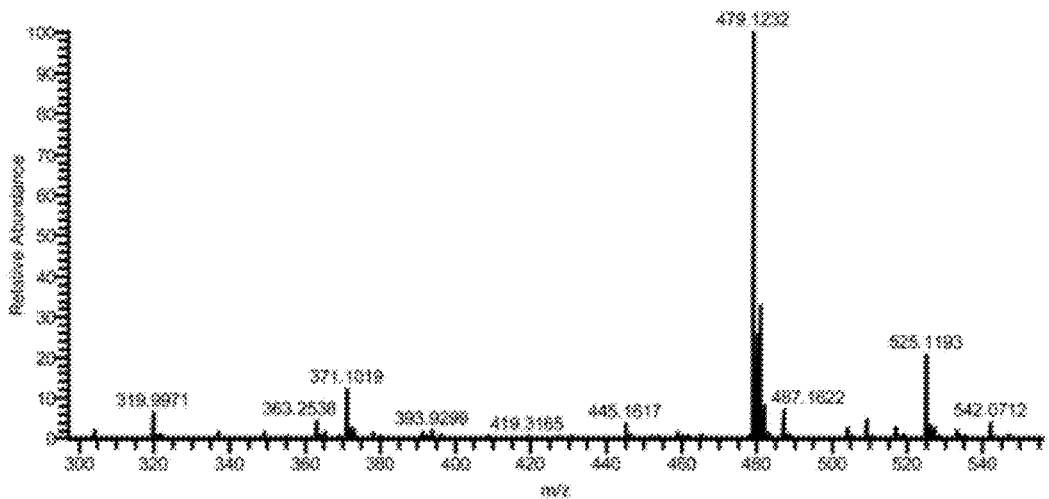
FIG. 8A, FIG. 8B, FIG. 8C, FIG. 8D, and FIG. 8E depict high-resolution MS-MS analysis of enzymatic reactions with chlortetracycline supports conversion to the m/z 467.12 oxidation product.
Figure 8B:
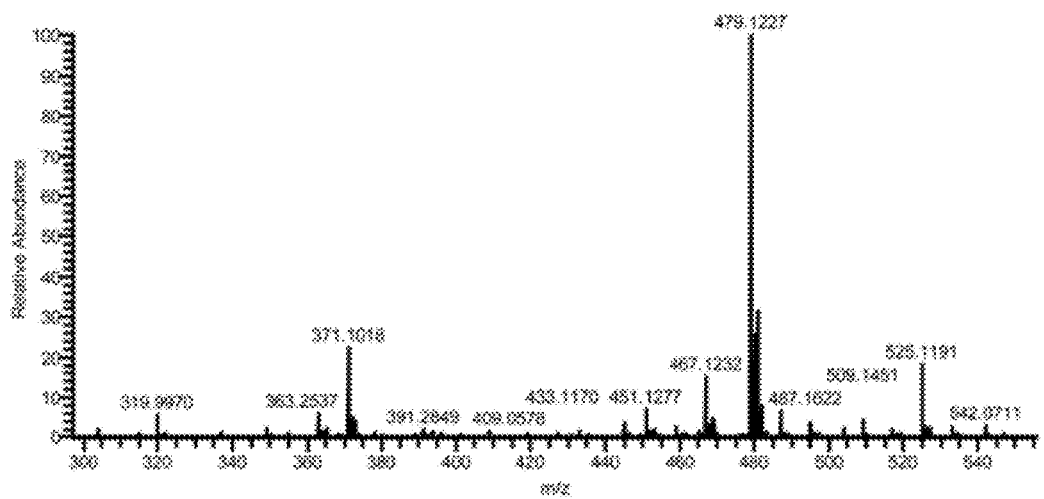
Figure 8C:
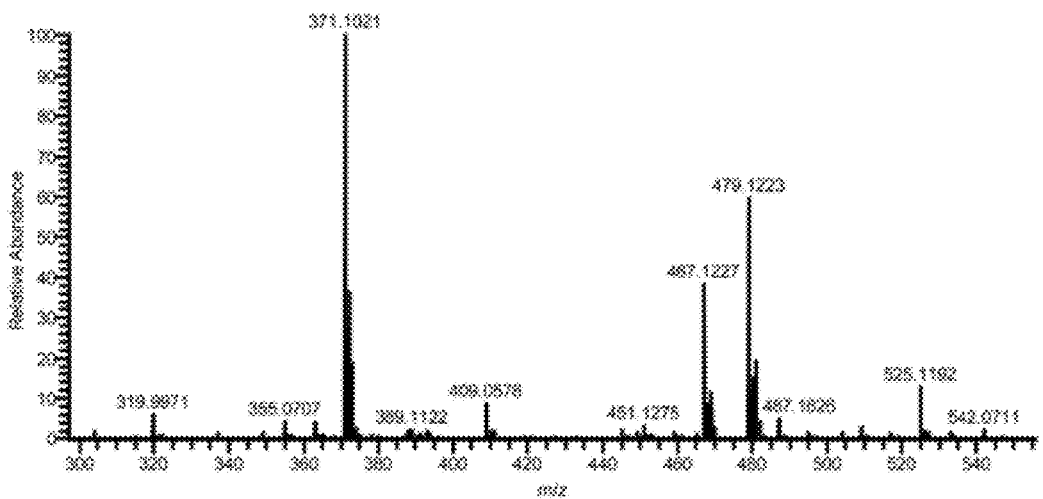
Figure 8D:
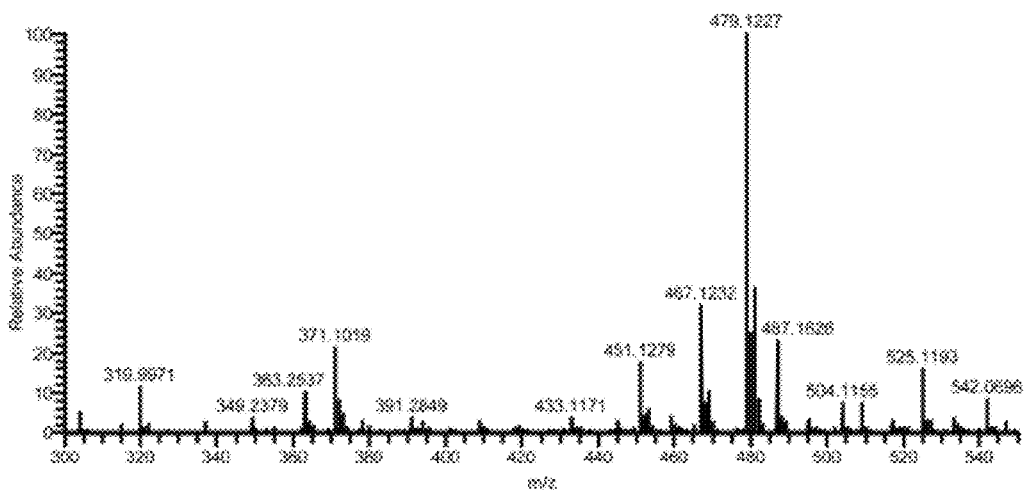
Figure 8E:
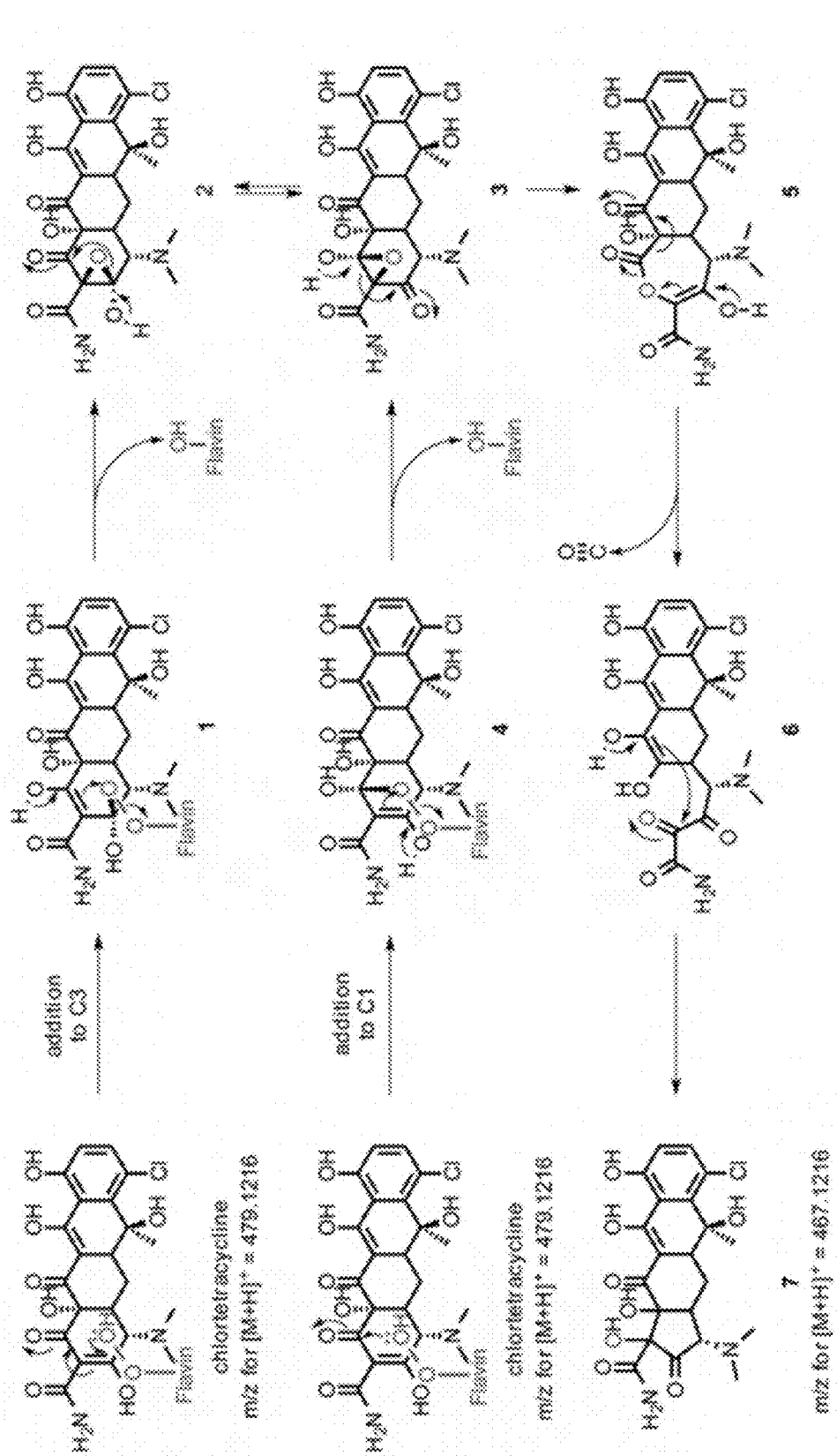

In the alternative binding mode, the nonplanarity of the chlortetracycline substrate positions the reactive A-ring C3 in closest proximity to the flavin cofactor. Notably, the C3 is 6.1 Å (FIG. 6C) and the C1 carbonyl is 7.4 Å (FIG. 6D) from the C4a of the flavin cofactor. These distances are similar to C11a of chlortetracycline and C4a of FAD in the Tet(X)+chlortetracycline structure,[27] and well within the C4a-reactive atom distances observed for flavin monooxygenases.[39] The C11a in the Tet(50)+chlortetracycline, on the other hand, is on the opposite side of the molecule and 7.9 Å away (FIG. 6E). Accordingly, we propose a mechanism in which the flavin peroxide attacks C3 of the chlortetracycline A ring, yielding intermediate 1 (FIG. 8E). Spontaneous epoxide formation gives intermediates 2 and 3, which rearranges to a cycloheptanone intermediate 5 via Baeyer-Villiger ring expansion. Expulsion of carbon monoxide yields intermediate 6, and ring contraction yields oxidation product 7, with an m/z of 467. Alternatively, intermediate 3 can be formed by flavin peroxide attack of C1 of the chlortetracycline A ring, via intermediate 4, and then similarly continuing through products 5-7. The final product 7 is consistent with the fragmentation pattern observed in tandem mass spectrometry (FIG. 6B). Similar oxidative cascades proceeding through Baeyer-Villiger reactions have been observed in the biosynthesis of the cyclic type II polyketide mithramycin by the flavin monooxygenase MtmOIV.[40] The discovery of alternative substrate binding modes and characterization of degradation products demonstrates the plasticity of tetracycline destructases for adapting flavoenzyme-mediated degradation chemistries to achieve resistance in the presence of diverse tetracycline scaffolds.

Anhydrotetracycline Locks the FAD in an OUT Conformation:

Due to the global dissemination of the β-lactamases, nearly all β-lactam antibiotics are co-developed with β-lactamase inhibitors,[29] an approach that has successfully prolonged their clinical utility. We reasoned that a similar strategy might be useful to counteract tetracycline resistance by inactivation, and therefore sought to identify small molecule inhibitors of these enzymes. Previously, we observed that anhydrotetracycline, a key biosynthetic precursor[41] and degradation product[42] of tetracycline with poor antibiotic activity was not degraded by Tet(47-56).[28] Nonetheless, it is known to be an effector of tetracycline producers and tetracycline-resistant bacteria by inducing expression of energetically expensive tetracycline efflux pumps, permitting tetracycline producers to survive and selecting against tetracycline resistance.[43] Based on the structural similarity to tetracycline and the intimate role that anhydrotetracycline plays in tetracycline biology, we hypothesized that anhydrotetracycline represents an evolutionarily-privileged chemical lead for inhibitor design.

Figure 9A:
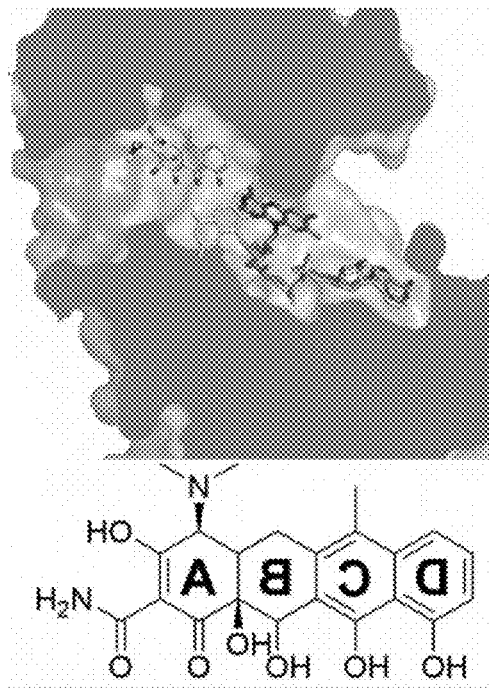
FIG. 9A, FIG. 9B, FIG. 9C, and FIG. 9D depict that anhydrotetracycline binds to the active site of Tet(50), trapping FAD in the unproductive OUT conformation.

We obtained a co-crystal structure of Tet(50) with anhydrotetracycline bound, and observed two unique features in comparison to our Tet(50)+chlortetracycline and the earlier Tet(X)+chlortetracycline structures. First, anhydrotetracycline binds to Tet(50) in a flipped orientation and in a position distinct from where chlortetracycline binds (FIG. 9A, FIG. 9B, FIG. 9C, FIG. 10A, FIG. 10B, FIG. 10C, FIG. 10D, FIG. 11A, FIG. 11B, and FIG. 11C). The unique binding mode for anhydrotetracycline is enabled by the lack of a 6-hydroxyl group of ring C present in tetracycline or chlortetracycline (FIG. 9A). Without this substitution at the 6 position, the tetracycline gains additional aromatic stabilization. The resultant planar structure allows the 6-methyl group to make van der Waals interactions with a conserved Thr/Ser at residue position 207 in Tet(47-56) (FIG. 9D, FIG. 11A, FIG. 11B, FIG. 11C, and FIG. 12). Thr-207 would cause a steric clash with the 6-methyl and 6-hydroxyl groups of ring C in tetracycline or chlortetracycline, explaining the distinct binding modes.

Figure 9B:
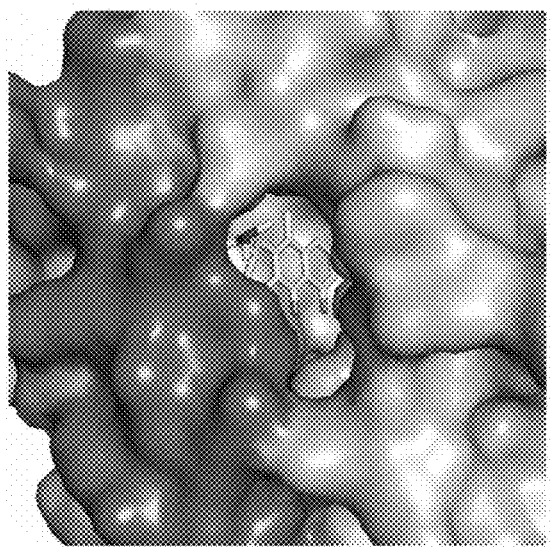
Figure 9C:
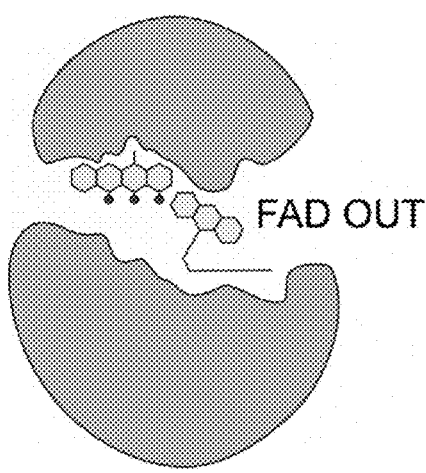
Figure 9D:
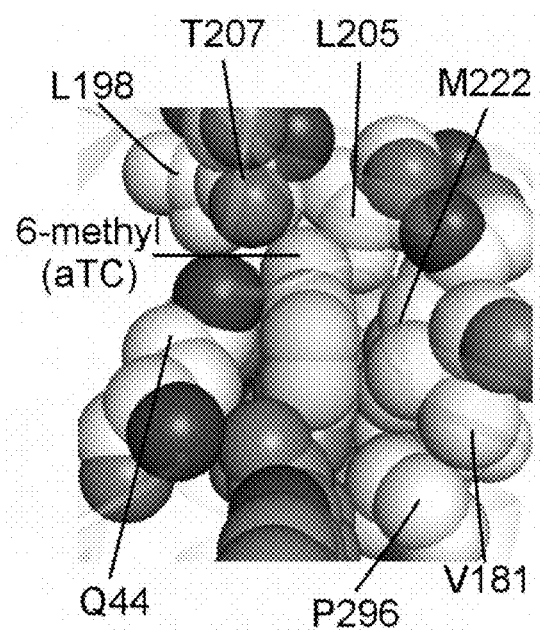
Figure 10A:
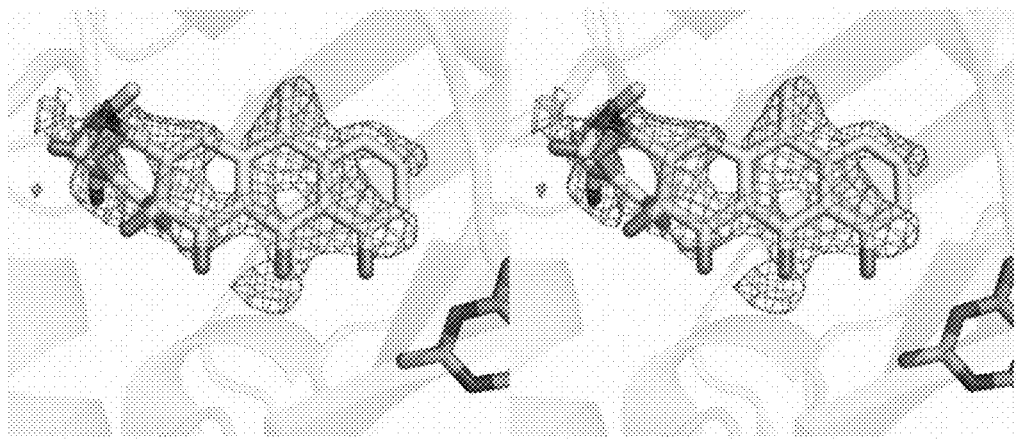
FIG. 10A, FIG. 10B, FIG. 10C, and FIG. 10D depict that anhydrotetracycline has a distinctive three-dimensional architecture with a significant bend between rings A and B, allowing for unambiguous modeling into the electron density.
Figure 10B:
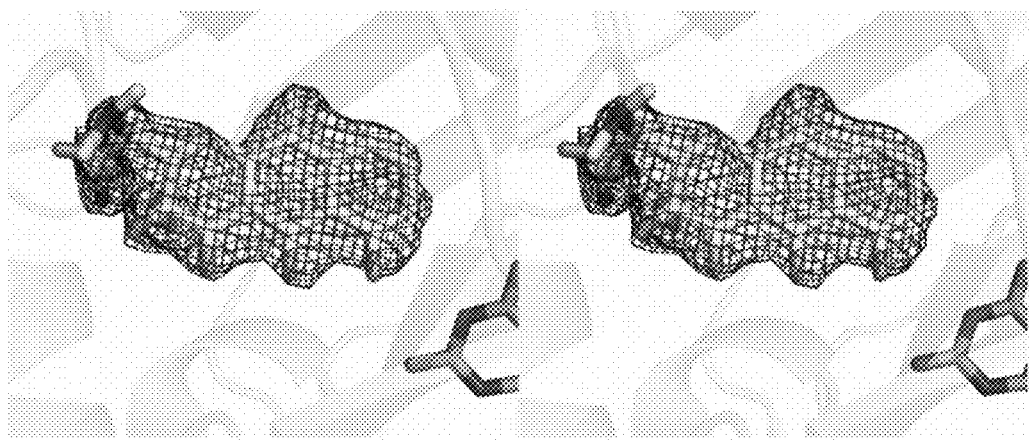
Figure 10C:
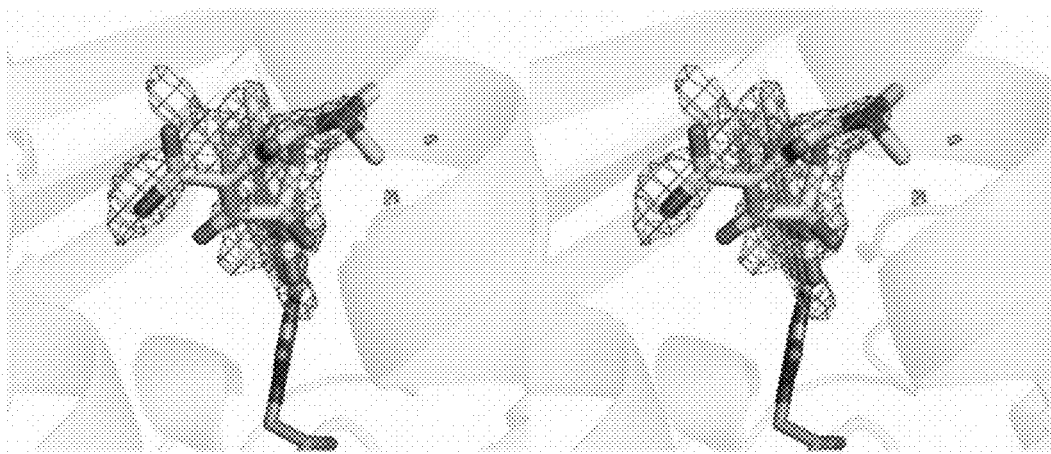
Figure 10D:
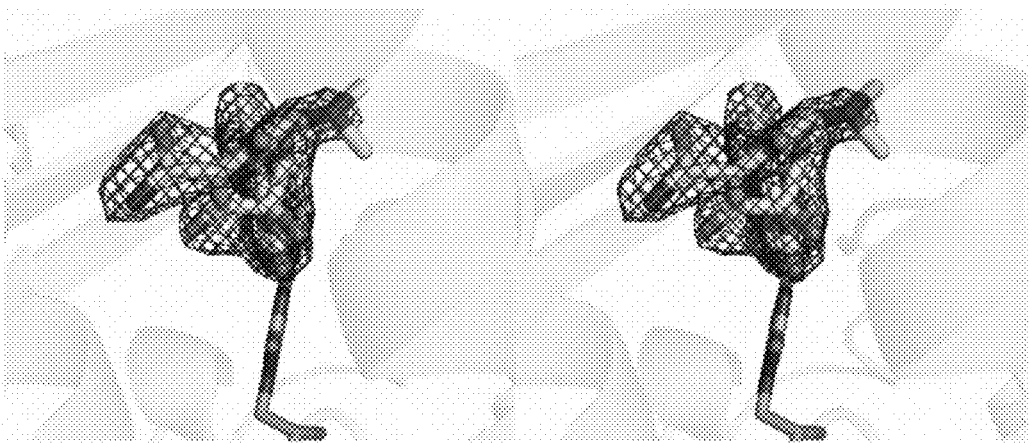
Figure 11C:
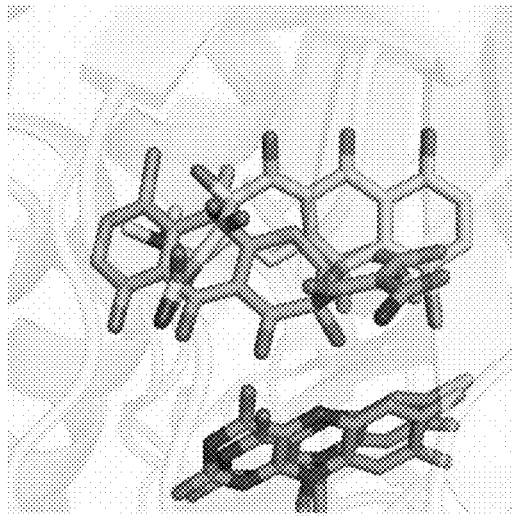
Figure 11C:
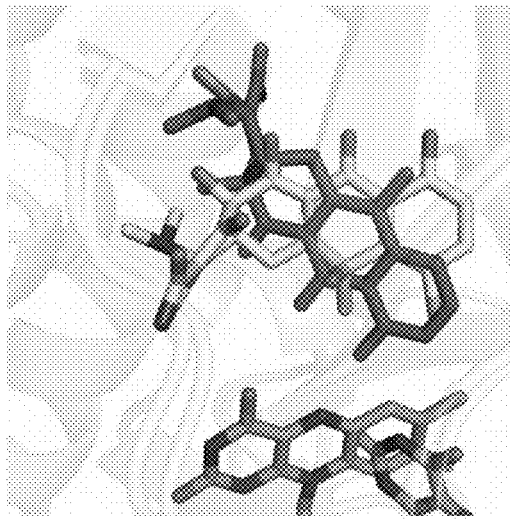
Figure 11C:
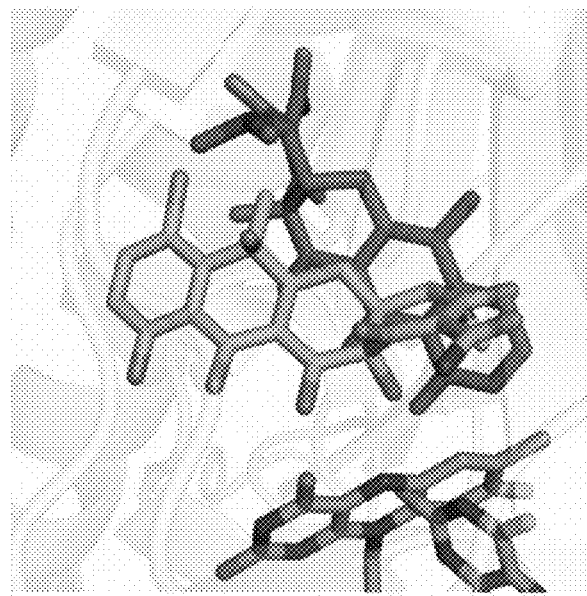
Figure 12:
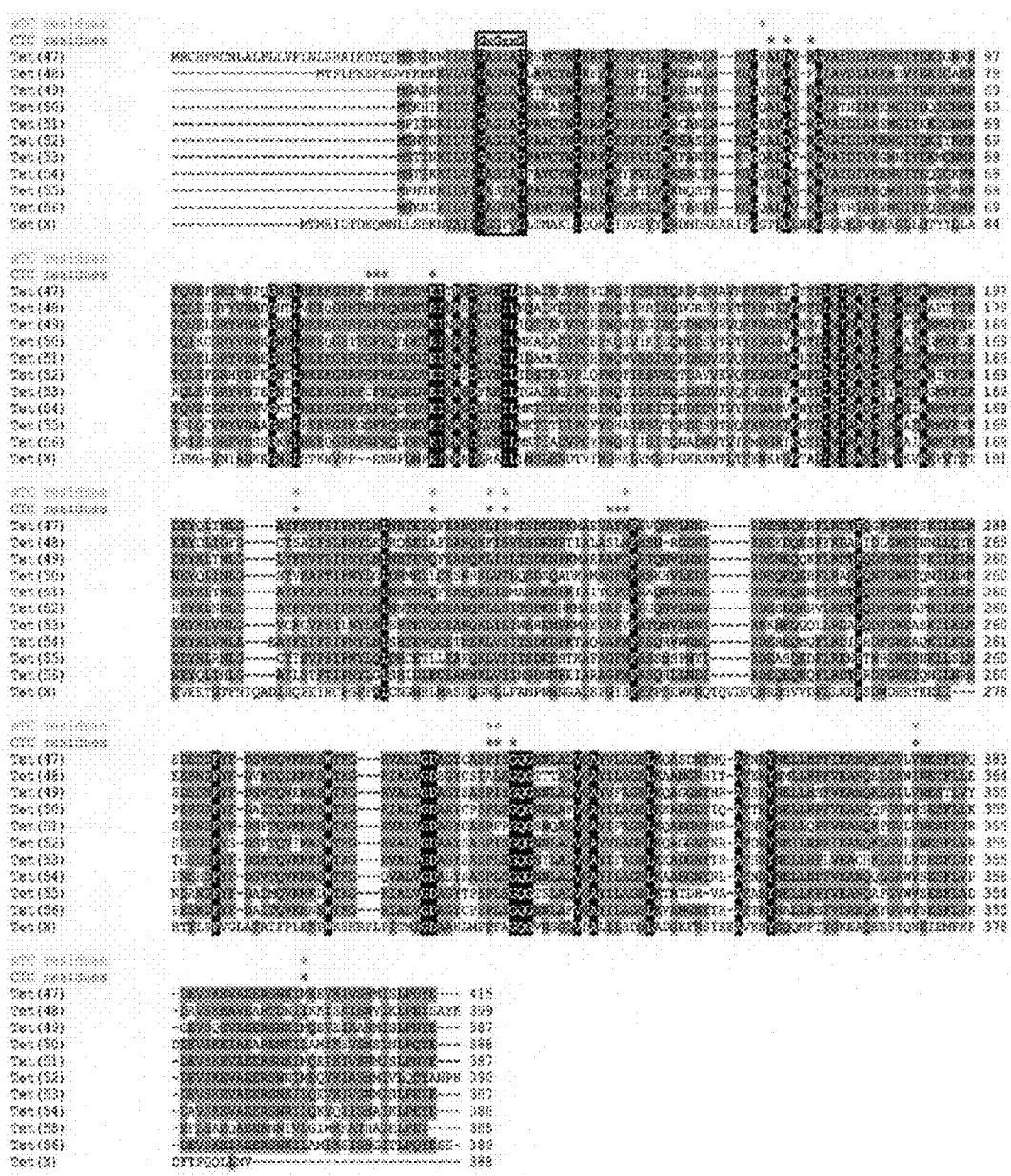
FIG. 12 depicts multiple sequence alignment of Tet(47-56, X). Tetracycline destructases have high levels of sequence similarity in the residues important for binding of anhydrotetracycline (aTC, orange) or chlortetracycline (CTC, pink). Alignment includes Tet(X), which shares at most 24.4% amino acid identity with Tet(47-56). Conserved FAD binding motif is boxed in blue.

The second interesting feature is that when anhydrotetracycline was bound, FAD was in the OUT conformation and the substrate-loading channel was open (FIG. 9B and FIG. 9C). The unique binding location of anhydrotetracycline locks the isoalloxazine moiety of FAD away from the substrate-binding site and sterically blocks the transition to the FAD IN conformation observed in the Tet(50)+chlortetracycline monomer B. This unexpected binding mode establishes a novel mechanism for inhibitors that stabilize the inactive OUT conformation of the FAD cofactor in flavoenzymes and prevents transition to the necessary FAD IN conformation for catalysis. Therefore, anhydrotetracycline is a mechanistic inhibitor of the tetracycline destructases that also competitively blocks substrate binding.

Figure 13A:
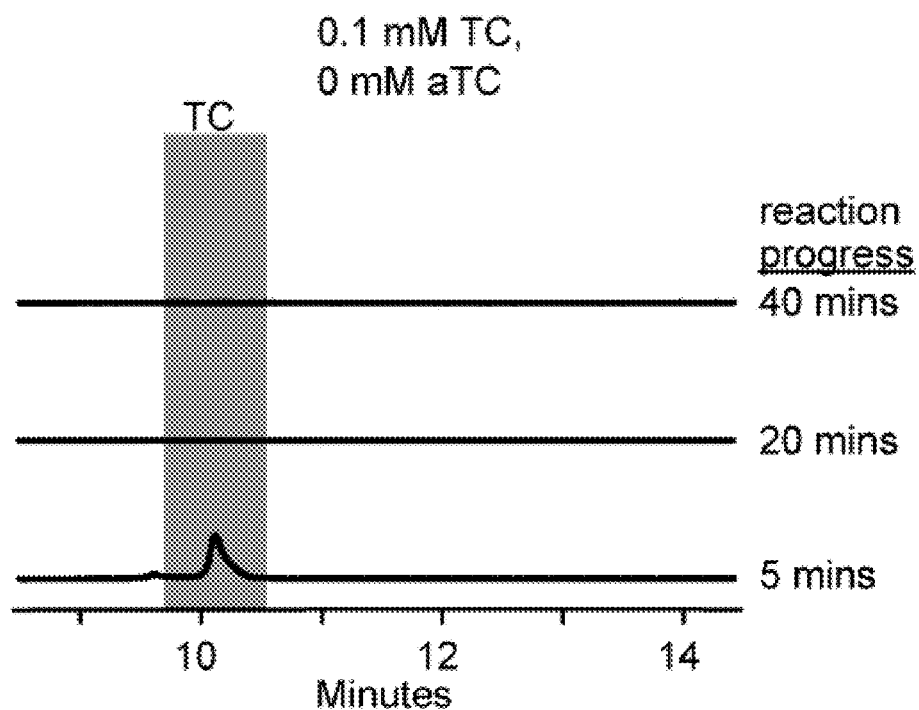
FIG. 13A, FIG. 13B, FIG. 13C, FIG. 13D, and FIG. 13E depict that anhydrotetracycline prevents enzymatic tetracycline degradation, functionally rescuing tetracycline antibiotic activity.
Figure 13B:
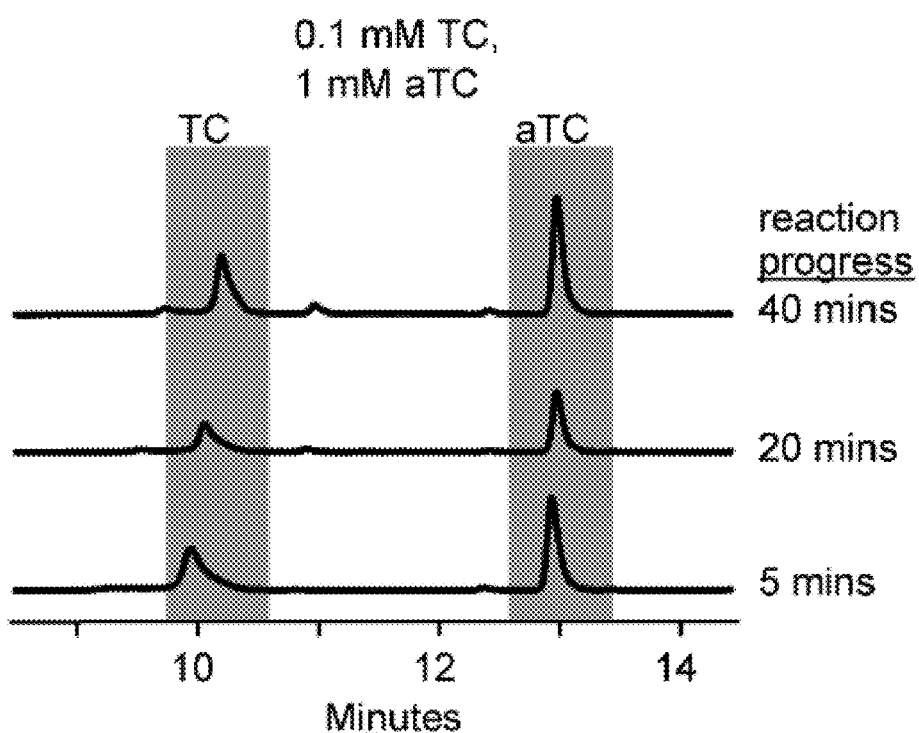
Figure 13C:
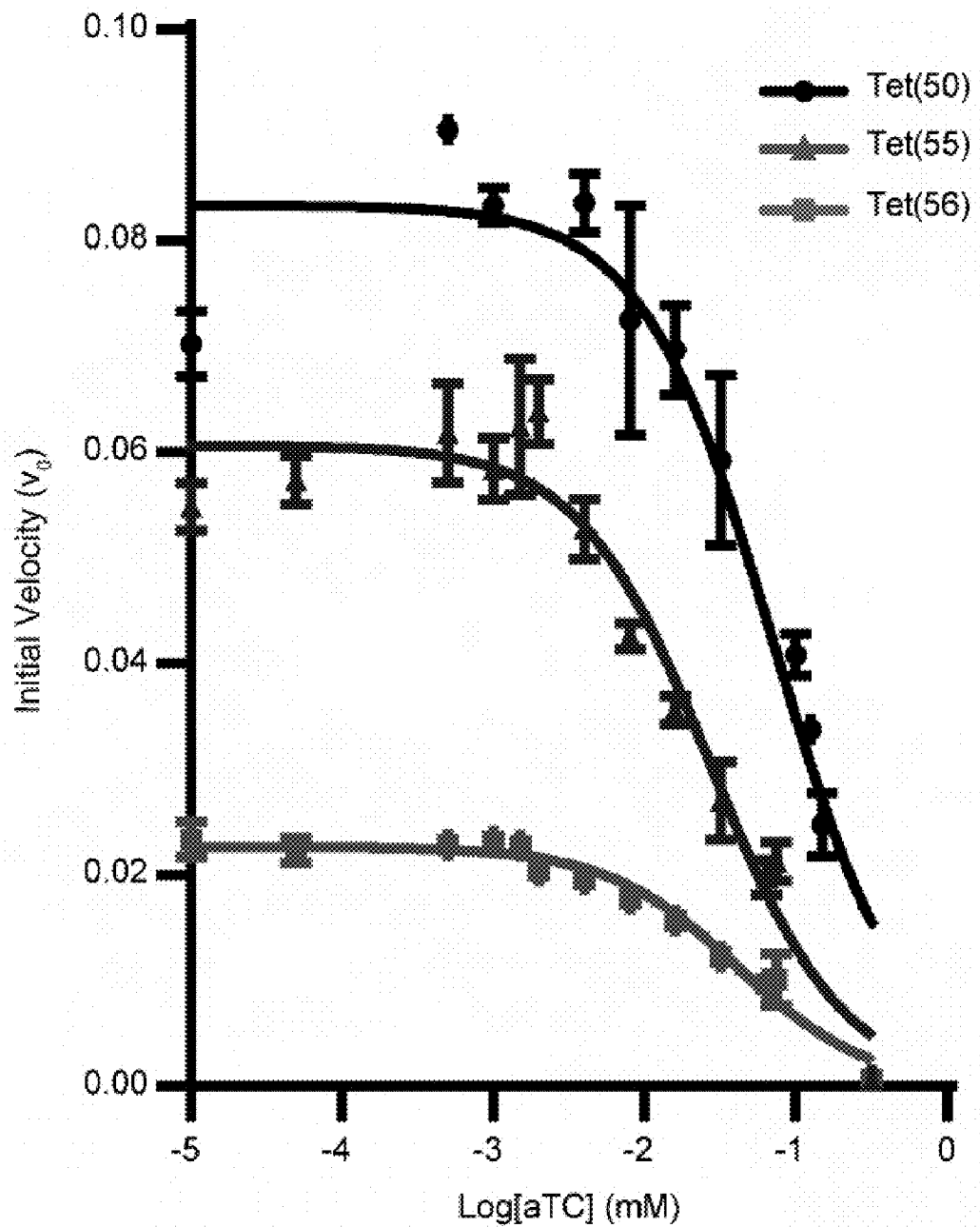

Anhydrotetracycline Inhibits Tetracycline Destructases:

We examined the effect of anhydrotetracycline on tetracycline destructase activity in vitro. We performed in vitro enzymatic reactions in the presence or absence of anhydrotetracycline followed by HPLC. For clinical relevance, we first focused on Tet(56), the tetracycline destructase from pathogenic L. longbeachae. We observed the Tet(56)-dependent degradation of 0.1 mM tetracycline over time, as demonstrated by the decrease in the tetracycline peak (FIG. 13A). However, in the presence of 1 mM anhydrotetracycline, the tetracycline peak does not change, indicating that tetracycline is not degraded (FIG. 13B). Similar results were observed for Tet(50,51,55,X) (FIG. 14A, FIG. 14B, FIG. 14C, FIG. 14D, and FIG. 14E and Table 4). We also monitored enzymatic inactivation of tetracycline using absorbance at 400 nm in the presence of a range of anhydrotetracycline concentrations. Anhydrotetracycline inhibited Tet(50,55,56) with IC50 values of 83.2±1.2 μM, 25.6±1.2 μM, and 37.1±1.1 μM, respectively (FIG. 13C). Thus, anhydrotetracycline prevents the enzyme-dependent degradation of tetracycline. Together with our structural data, this indicates a common mechanism of inhibition for tetracycline-inactivating enzymes, and establishes anhydrotetracycline as a lead compound that presents a flexible starting point for generating tetracycline destructase inhibitors with improved activity.[44] This inhibition strategy that stabilizes inactive cofactor states is widely applicable to the larger superfamily of flavoenzymes and offers new avenues for inhibiting any member of this superfamily, many of which have been implicated in human disease and represent promising targets for hypercholesterolemia and antifungal drugs.[45]

TABLE 4

HPLC peak height ratios

| Enzyme | Reaction progress (mins) | TC/aTC peak height ratio |
| --- | --- | --- |
| No Enzyme | 5 | 0.639 |
| No Enzyme | 20 | 0.579 |
| No Enzyme | 40 | 0.578 |
| Tet(50) | 5 | 0.670 |
| Tet(50) | 20 | 0.344 |
| Tet(50) | 40 | 0.249 |
| Tet(51) | 5 | 0.613 |
| Tet(51) | 20 | 0.456 |
| Tet(51) | 40 | 0.430 |
| Tet(55) | 5 | 0.668 |
| Tet(55) | 20 | 0.524 |
| Tet(55) | 40 | 0.441 |
| Tet(56) | 5 | 0.488 |
| Tet(56) | 20 | 0.472 |
| Tet(56) | 40 | 0.472 |
| Tet(X) | 5 | 0.731 |
| Tet(X) | 20 | 0.435 |
| Tet(X) | 40 | 0.387 |

Figure 13D:
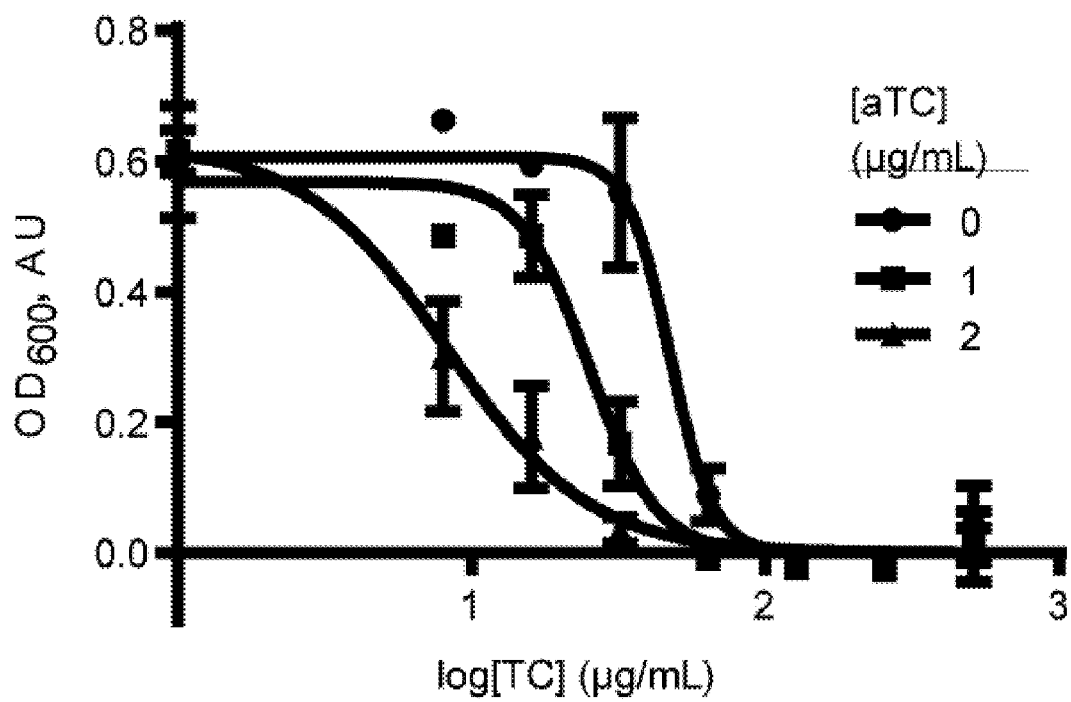
Figure 13E:
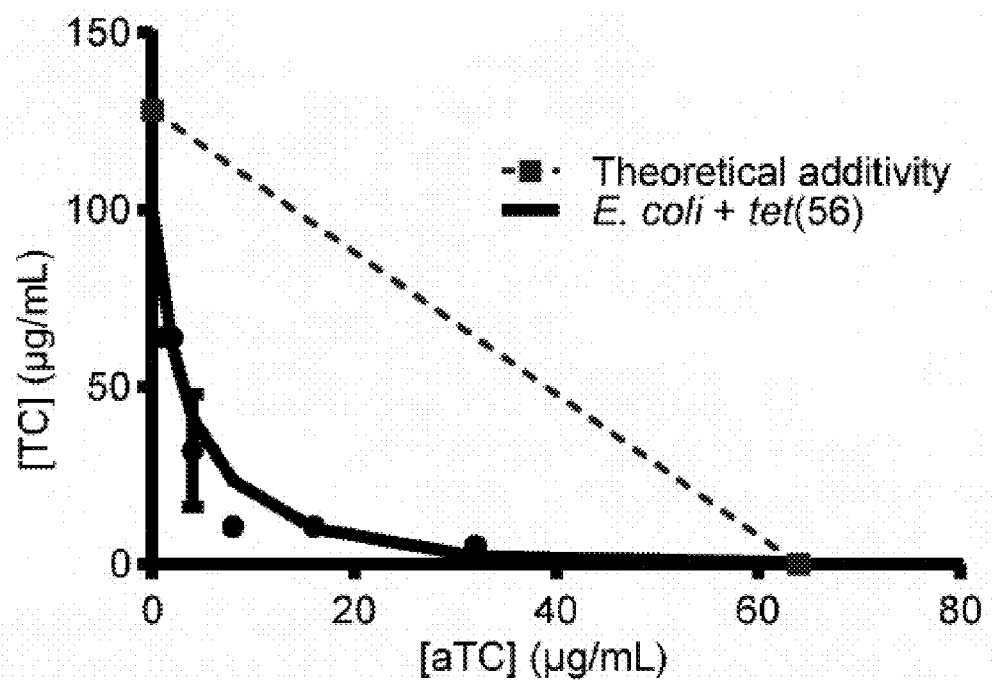
Figure 14A:
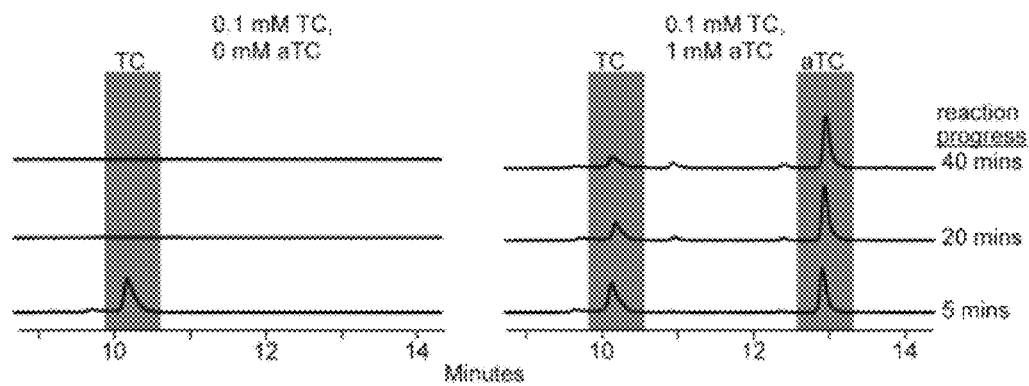
FIG. 14A, FIG. 14B, FIG. 14C, FIG. 14D, and FIG. 14E depict that anhydrotetracycline prevents enzymatic degradation of tetracycline. HPLC chromatograms indicate complete consumption of 0.1 mM tetracycline (TC) over the period assayed by Tet(50) (FIG. 14A), Tet(51) (FIG. 14B), Tet(55) (FIG. 14C), and Tet(X) (FIG. 14D), but not in the no enzyme control (FIG. 14E). 1 mM anhydrotetracycline (aTC) is sufficient to decrease or prevent tetracycline degradation.
Figure 14B:
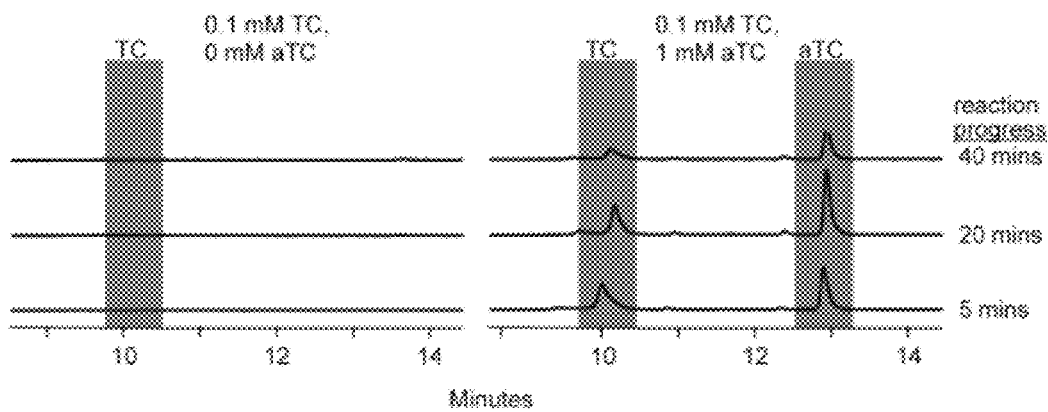
Figure 14C:
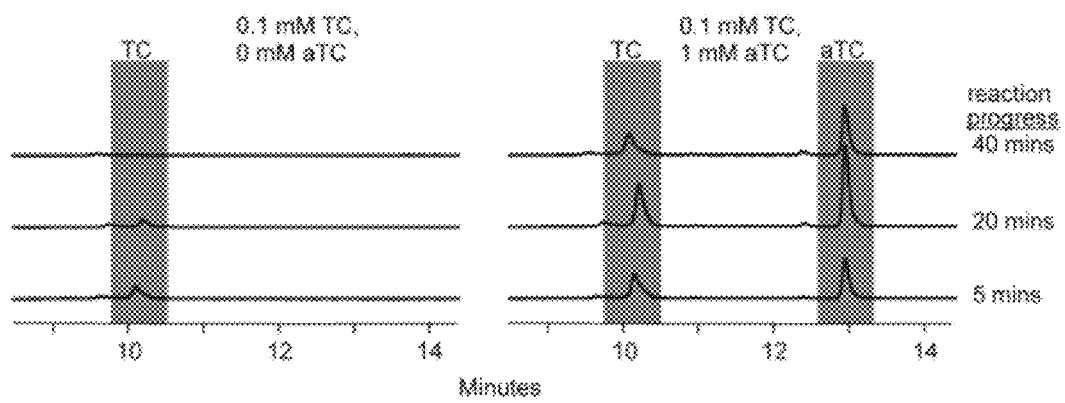
Figure 14D:
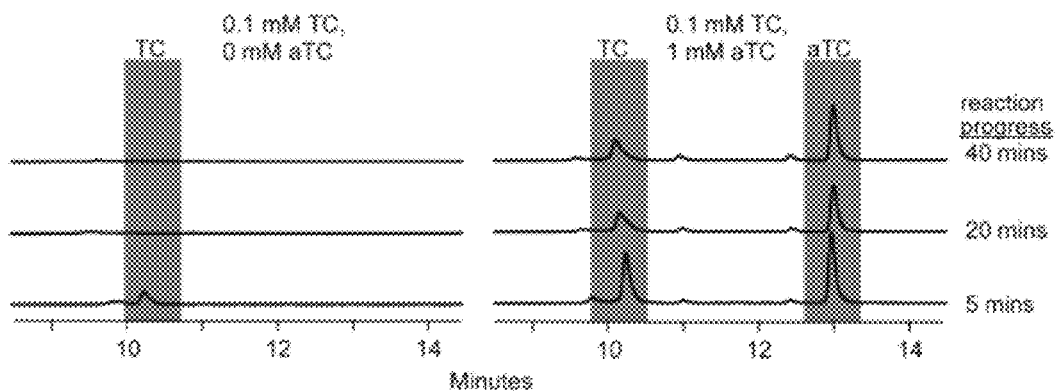
Figure 14E:
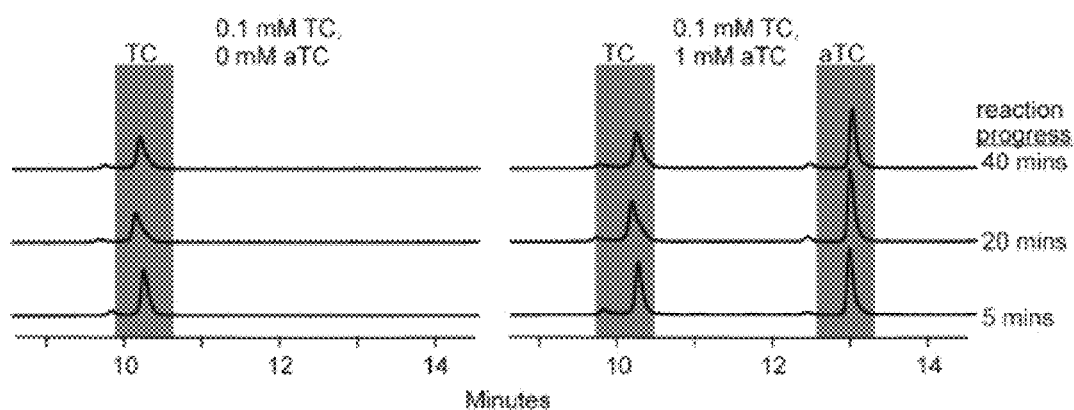
Figure 15A:
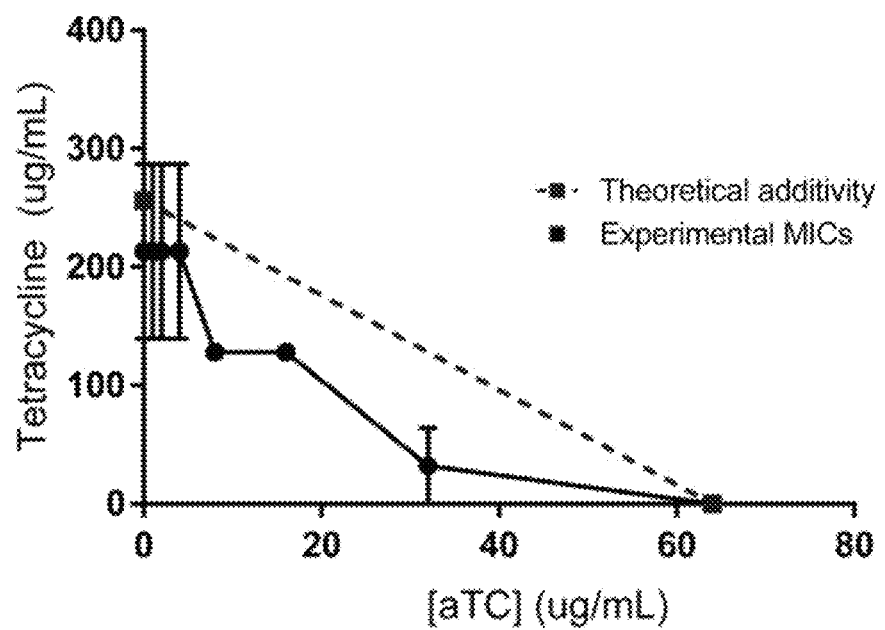
FIG. 15A, FIG. 15B, FIG. 15C, FIG. 15D, FIG. 15E, and FIG. 15F depict that anhydrotetracycline synergizes with tetracycline to kill $E. coli$ expressing tet(50,51,55,56) but not tet(X). Anhydrotetracycline exhibits synergy with tetracycline against $E. coli$ expressing tet(50) (FIG. 15A), tet(51) (FIG. 15B), tet(55) (FIG. 15C), and tet(56) (FIG. 15D), but not tet(X) (FIG. 15E) or empty vector control (FIG. 15F). Dashed blue lines indicate the theoretical concentrations of additive interactions.
Figure 15B:
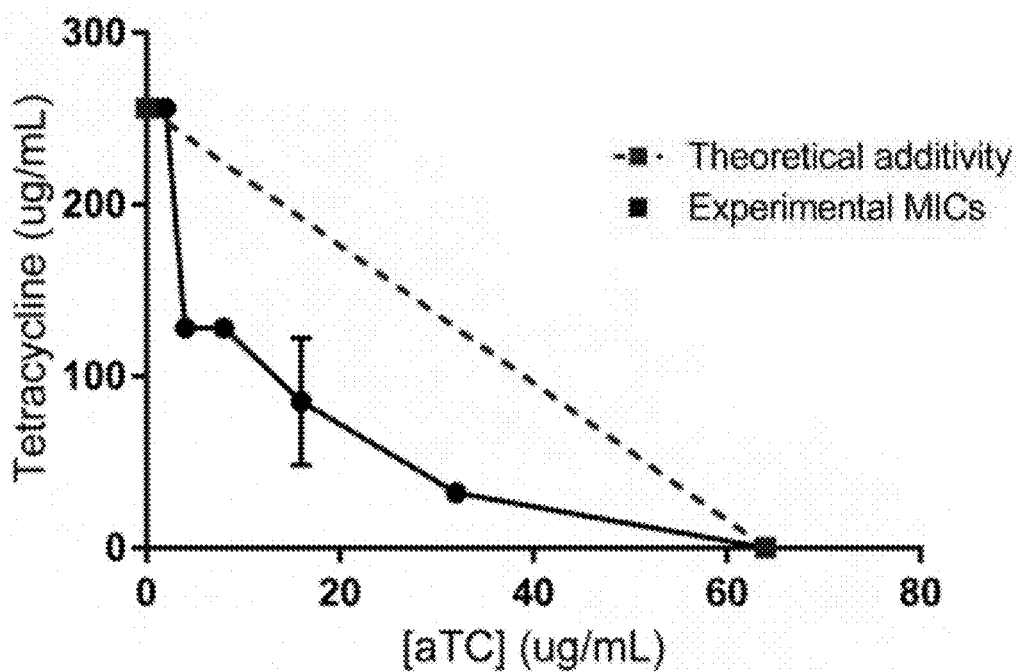
Figure 15C:
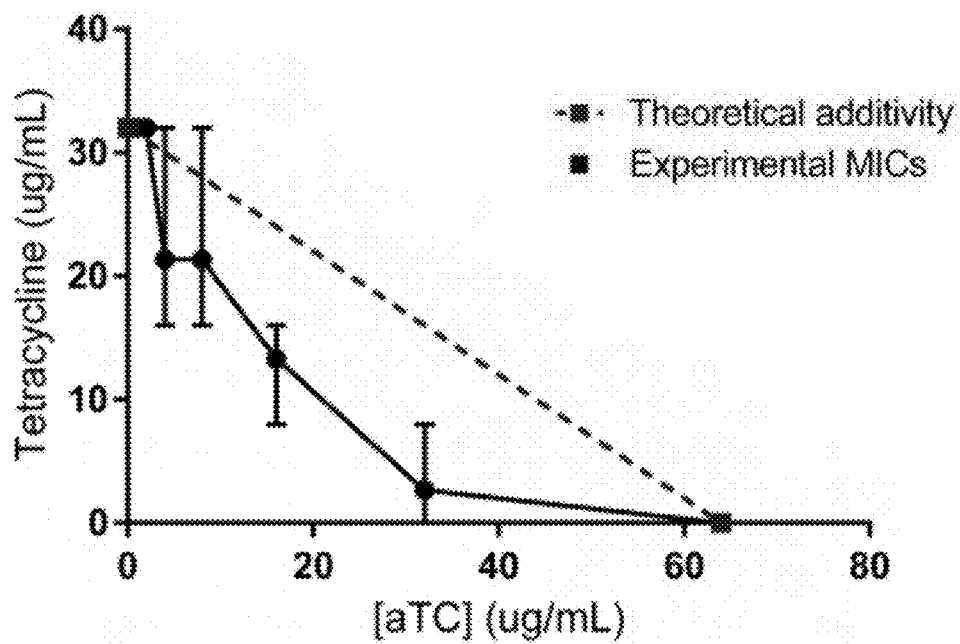
Figure 15D:
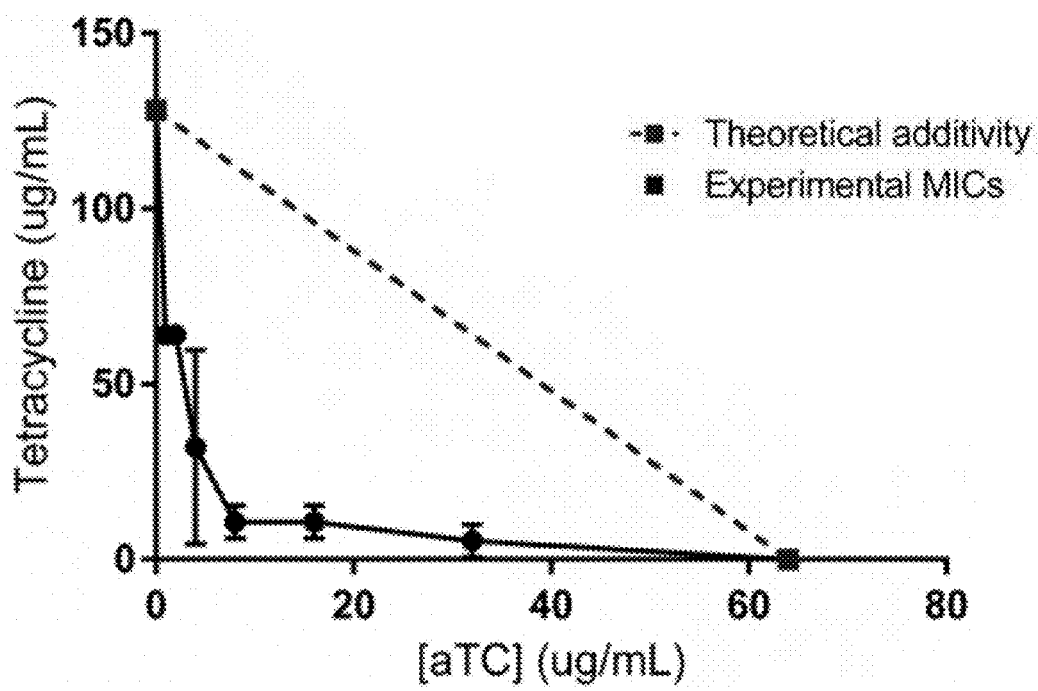
Figure 15E:
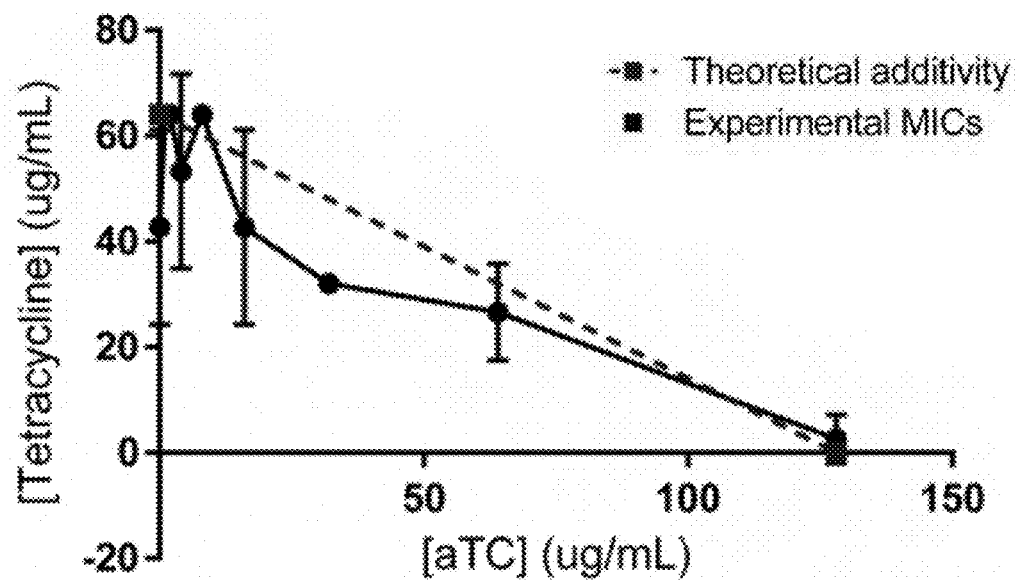
Figure 15F:
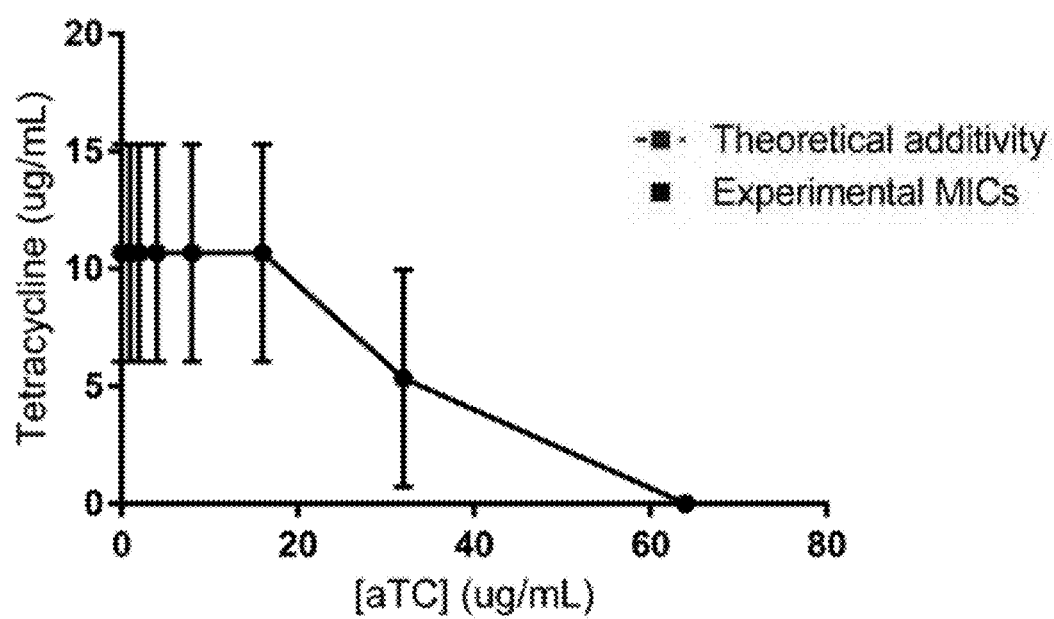

Novel inhibition mechanism restores tetracycline activity: Our data suggest that a tetracycline/tetracycline-destructase-inhibitor (e.g., anhydrotetracycline) combination therapy strategy could potentially be employed to rescue antibiotic activity of tetracyclines against bacteria that encode tetracycline-inactivating enzymes. Tet(X) and Tet(56) are of particular interest due to their clinical significance. Tet(X) has been recently identified in a number of human pathogens, including 11 nosocomial uropathogens from Sierra Leone[46] and 12 *Acinetobacter baumanni* isolates from a hospital in China.[47] We also showed that tet(56) is present and functional in *L. longbeachae*[28]—a pathogen responsible for causing Pontiac Fever and Legionnaires' Disease.[32,33] Accordingly, we tested whether anhydrotetracycline rescues tetracycline efficacy against *E. coli* expressing tet(56). Two μg/mL anhydrotetracycline caused a greater than 5-fold change in sensitivity of *E. coli* expressing tet(56) to tetracycline in liquid culture, as indicated by a change in IC50 from 47.4 to 8.27 g/mL (FIG. 13D). Further, anhydrotetracycline and tetracycline acted synergistically to inhibit growth of *E. coli* expressing Tet(50,51,55,56), with fractional inhibitory concentration indices (FICI) of 0.625, 0.5, 0.375 and 0.1875, respectively (FIG. 13E, FIG. 15A, FIG. 15B, FIG. 15C, FIG. 15D, FIG. 15E, and FIG. 15F). Although anhydrotetracycline is not degraded by Tet(47-56), it is slowly degraded by Tet(X)[28]. However, anhydrotetracycline still was able to prevent tetracycline degradation by Tet(X) in vitro (FIG. 14A, FIG. 14B, FIG. 14C, FIG. 14D, and FIG. 14E). Our proof of concept experiment, taken together with our structural and in vitro data, reveals that a co-administration strategy based on inhibition of tetracycline-inactivating enzymes could be effective for the treatment of tetracycline-resistant bacterial infections.

Discussion for Example 1

Figure 16A:
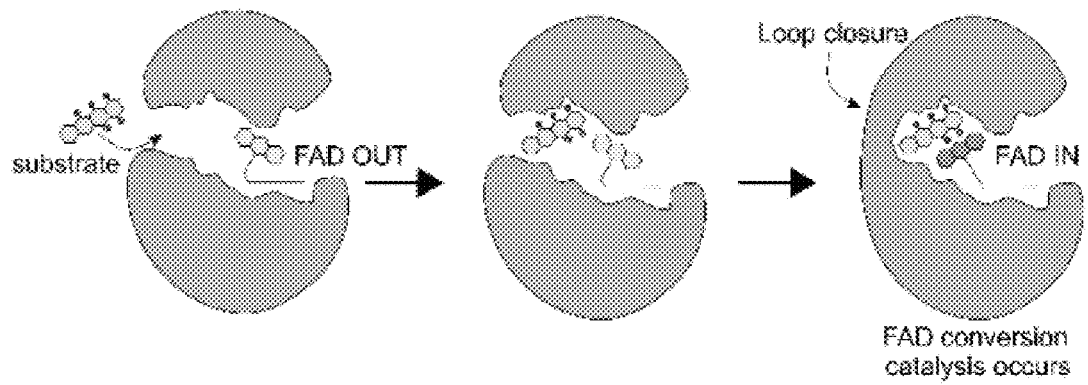
FIG. 16A and FIG. 16B depict model for binding dynamics, substrate plasticity, and inhibition of tetracycline-inactivating enzymes.
Figure 16B:
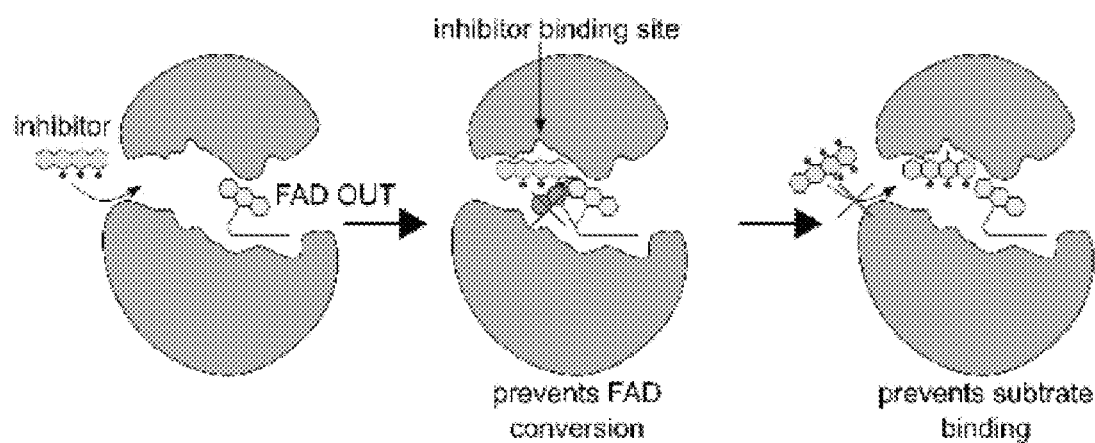

The widespread anthropogenic use of tetracycline antibiotics motivates the immediate study of emerging mechanisms of tetracycline resistance, such as enzymatic inactivation. Our data provide unprecedented insight into the dynamics of tetracycline-inactivating enzymes and reveal a novel mode of inhibition. Substrates like chlortetracycline are loaded into enzymes in the FAD OUT conformation through the substrate-loading channel (FIG. 16A), which is open as a flexible loop is pulled away from the channel. Upon substrate binding, the enzyme converts to FAD IN, the channel closes, and catalysis can occur due to the proximity of FAD to the substrate. Mechanistic inhibitors like anhydrotetracycline also enter the enzyme through the same channel but bind at a distinct site (FIG. 16B). Binding of inhibitor in this location sterically blocks FAD conversion to the IN conformation and prevents subsequent substrate binding and catalysis. Our model predicts that compounds that either bind with higher affinity to the inhibitor binding pocket, or that concomitantly bind to the inhibitor and substrate-binding sites will provide enhanced inhibition for the control of tetracycline resistance. This novel mechanism of inhibition is not only applicable to preventing antibiotic resistance, but is highly relevant to additional FAD dependent enzymes that comprise the flavoenzyme superfamily and are of clinical interest.[45]

The rise in resistance to early-generation tetracyclines has spurred the development of next-generation derivatives, including tigecycline (approved for human use in 2005),[15] and eravacycline and omadacycline (currently in late-stage clinical trials).[16,17] These newer drugs are designed to evade resistance by efflux or ribosomal protection, but they are largely untested against tetracycline-inactivating enzymes. Alarmingly, tigecycline was found to be vulnerable to oxidative inactivation by Tet(X),[27] which was recently identified for the first time in numerous pathogens of high clinical concern.[46,47] These challenges highlight the immediate importance of studying mechanisms of emerging tetracycline resistance, such as those described here that expand substrate scope.

Tetracycline resistance by enzymatic inactivation has thus far been rarely documented compared to resistance by efflux or ribosomal protection. Growing evidence, however, indicates that enzymatic tetracycline inactivation is a widespread feature in soil microbial communities,[28] and is a recently observed emerging threat in human pathogens.[46-48] Flavoenzymes display a proclivity for horizontal gene transfer and gene duplication, bestowing the potential to spread between bacteria and acquire novel functions.[49] Interestingly, the contigs on which tet(47-55) were discovered also contained mobility elements and other resistance genes,[9,28] suggesting that their original genomic context may be as part of a multidrug resistance cassette or mobile genetic element. This indicates that tetracycline-inactivating enzymes pose a threat for facile acquisition by additional human pathogens. Indeed, we show that tet(56) is present and functional in the human pathogen *L. longbeachae*, and tet(X) has now been reported in four out of six ESKAPE pathogens,[46-48] demonstrating the urgency of this threat. Our results reveal the structural basis for plasticity and dynamics in substrate binding in these enzymes.

Methods for Example 1

*Legionella* Plasmid Construction:

The Tet(56) deletion plasmid, pJB7204 (SEQ ID NO. 9), was constructed by amplifying 2 kb of DNA upstream and downstream of the Tet(56) ORF using primers JVP2913 (SEQ ID NO. 1)/JVP2910 (SEQ ID NO. 2) and JVP2911 (SEQ ID NO. 3)/JVP2912 (SEQ ID NO. 4) and *Legionella longbeachae* chromosomal DNA. The PCR products were digested with SalI/NotI and NotI/SacI, respectively, and ligated into SalI/SacI-digested suicide vector pSR47S.[50] The ligated product was transformed into EC100D::Δpir and selected on LB plates containing 20 μg/ml kanamycin. The Tet(56) complementing clone, pJB7207 (SEQ ID NO. 10), was constructed by amplifying the Tet(56) ORF using primers JVP2921 (SEQ ID NO. 5)/JVP2922 (SEQ ID NO. 6) and *Legionella longbeachae* chromosomal DNA. The PCR product was digested with BamHI/SalI and cloned into BamHI/SalI-digested expression vector pJB1625 (SEQ ID NO. 8).

*Legionella* Strain Construction:

The Tet(56) deletion strain, JV8858, was constructed by a traditional loop-in/loop-out strategy. Briefly, the wild type *Legionella longbeachae* strain JV595 (ATCC 33462) was transformed by electroporation with the ΔTet(56) suicide plasmid pJB7204 (SEQ ID NO. 9) and integrants were selected on CYE plates[51] containing 30 μg/ml kanamycin. Resolution of the merodiploid was obtained on CYE plates containing sucrose. Strains were then electroporated with the vector pJB1625 or the Tet(56) complementing clone pJB7207 (SEQ ID NO. 10) and transformants were selected on CYE plates containing 5 g/ml chloramphenicol.

Tetracycline inactivation in *Legionella*:

Antibiotic susceptibility testing was performed using *L. longbeachae* wild type and deletion strains and *L. pneumophila*,[52] bearing either the vector pJB1625 (SEQ ID NO. 8)[53] or the Tet(56) complementing clone pJB7207 (SEQ ID NO. 10). Minimum inhibitory concentrations were determined according to Clinical and Laboratory Standards Institute (CLSI) procedures with the following modifications. Results are representative of three independent experiments. The strains were initially grown as a patch on CYE plates containing chloramphenicol for 2 days at 37° C. The bacteria were swabbed into distilled water, washed one time, and resuspended at an 600 nm absorbance (OD600) of 1 (~1E9 CFU/ml). The culture was diluted 200 fold into 10 mL of buffered AYE media containing 2 μg/ml chloramphenicol and a range of tetracycline but lacking supplemental iron, as iron can interfere with tetracycline activity. The cultures were grown for 48 hours at 37° C. on a roller drum and the absorbances (OD600) were periodically measured using a GENESYS 20 Spectrophotometer.

Cloning, Expression and Purification of Tetracycline-Inactivating Enzymes:

All genes encoding tetracycline-inactivating enzymes were cloned into the pET28b(+) vector (Novagen) at BamHI and NdeI restriction sites. Constructs were transformed into BL21-Star (DE3) competent cells (Life Technologies). Cells harboring the plasmid were grown at 37° C. in LB medium containing a final concentration of 0.03 mg/mL kanamycin. Once cells reached an OD600 of 0.6, cells were cooled to 15° C. and induced with 1 mM IPTG overnight. After this period, cells were harvested by centrifugation at 4000 rpm for 10 minutes at 4° C. Cell pellets were suspended in 10 mL of 50 mM Tris (pH 8.0), 100 mM NaCl, 10 mM imidazole (pH 8.0), 1 mM PMSF, and 5 mM BME per 1 liter of LB medium and stored at −80° C.

Cells were thawed in the presence of 0.25 mg/mL lysozyme and disrupted using sonication on ice for 60 seconds. The cell extract was obtained by centrifugation at 13,000 rpm for 30 minutes at 4° C. and was applied onto nickel rapid run agarose beads (Goldbio) equilibrated with wash buffer (50 mM Tris (pH 8.0), 150 mM NaCl, 20 mM imidazole (pH 8.0), and 5 mM BME). The wash buffer was used to wash the nickel column three times with five column volumes. After washing, protein was eluted with five column volumes of elution buffer (wash buffer with 300 mM imidazole). The protein sample was further purified by gel chromatography using a HILOAD 16/600 SUPERDEX 200 pg column (GE Healthcare) equilibrated with 10 mM Tris (pH 8.0), 150 mM NaCl, and 5 mM dithioerythritol (DTT). The fractions containing the protein of interest were pooled and concentrated using a 30K MWCO AMICON centrifugal filter (Millipore).

Tet(55) Selenomethionine-Labelling:

For selenomethionine-labelled Tet(55) (Se-Met Tet(55)), cells were grown in 1 L of SELENOMET Medium supplemented with SELENOMET Nutrient Mix (Molecular Dimensions Limited). Once cells reached an OD600 of 0.6, feedback inhibition amino acid mix (0.1 g of lysine, threonine, phenylalanine; 0.05 g of leucine, isoleucine, valine; 0.05 g of L(+) selenomethionine (ACROS Organics 259960025)) was added and the cells were shaken for 15 minutes at 15° C. After 15 minutes, cells were induced at 15° C. with 1 mM IPTG overnight. All other purification conditions were the same as for the native tetracycline-inactivating enzymes.

Crystallization, Data Collection, and Structure Determination:

For crystallization, Se-Met Tet(55) was concentrated to 25 mg/mL. Crystals were obtained by vapor diffusion using hanging drops equilibrated at 18° C. Se-Met Tet(55) crystallized in 0.1 M Tris-HCl (8.5) and 20-25% PEG 3000. Se-Met Tet(55) crystals were harvested directly from the growth condition and flash-frozen under liquid nitrogen.

Native Tet(55) was concentrated to 50 mg/mL and crystallized in 0.1 M Tris-HCl (8.5) and 25-27% PEG 4000. Native Tet(55) crystals were harvested directly from the growth condition and flash-frozen. Tet(50) was concentrated to 35 mg/mL and crystallized in 0.1 M MES (pH 6.0-6.5), 1.6-2.0 M ammonium sulfate, 2-10% 1,4-Dioxane. Crystals were harvested directly from the growth condition and flash-frozen. For co-crystal structures, Tet(50) was concentrated to 17 mg/mL, and Tet(50) crystals were soaked with mother liquor plus 5 mM chlortetracycline or 4 mM anhydrotetracycline for 30 minutes before flash-freezing. Tet(51) was concentrated to 13 mg/mL and crystallized in 0.1 M MES (pH 6.0) and 10% PEG 6000. Crystals were cryo-protected with 0.1 M MES (pH 6.0), 10% PEG 6000, and 30% glycerol before flash-freezing. Tet(56) was concentrated to 38 mg/mL and crystallized in 0.1 M tri-sodium citrate (pH 5.6), 10% PEG 4000, 10% isopropanol. Tet(56) crystals were cryo-protected in 0.1 M tri-sodium citrate (pH 5.6), 10% PEG 4000, 10% isopropanol, and 20% glycerol before flash-freezing.

The crystal structure of Tet(55) was solved by selenomethionine labeling and single-wavelength anomalous dispersion (SAD) (Table 1), as molecular replacement using the previously published Tet(X) structures was unsuccessful. The inability to solve the structure by molecular replacement demonstrates that tetracycline-inactivating enzymes are structurally diverse and multiple structures are required to capture the diversity within the family. X-ray data for selenomethionine-labelled Tet(55) were collected from a single crystal using a wavelength of 0.976289 Å at synchrotron beamline 4.2.2 of the Advanced Light Source in Berkeley, Calif. All other native data sets were collected at a wavelength of 1 Å. Data were collected on the CMOS detector and were processed with XDS.[54] Structure solution for Se-Met Tet(55) was performed using PHENIX AutoSol. Thirteen selenium sites were found, which gave a figure of merit of 0.370. The resulting Tet(55) model was refined against the native Tet(55) data set. R and Rfree flags were imported from the Se-Met Tet(55) mtz file using UNIQUEIFY within the CCP4 package.[55] Tet(50,51,56) structures were solved my PHENIX AutoMR using an ensemble of three domains of Tet(55) (domain 1=aa1-70, aa100-172, aa276-319; domain 2=aa71-99, 173-275; domain 3=aa320-387). Structure solution for the Tet(50) chlortetracycline and anhydrotetracycline structures were performed by refinement with the apo Tet(50) structure, from which the R and Rfree flags were imported using UNIQUEIFY.

Subsequent iterated manual building/rebuilding and refinement of models were performed using Coot[56] and PHENIX[57], respectively. The structure validation server MolProbity[58] was used to monitor refinement of the models. All final refined models have favorable crystallographic refinement statistics (See Table 1).

In Vitro Tetracycline and Chlortetracycline Inactivation Assays:

Reactions were prepared in 100 mM TAPS buffer with 100 μM substrate, 14.4 μM enzyme, and an NADPH regenerating system consisting of the following components (final concentrations): glucose-6-phosphate (40 mM), NADP+ (4 mM), $MgCl_2$ (1 mM), and glucose-6-phosphate dehydrogenase (4 U/ml). The regeneration system was incubated at 37° C. for 30 minutes to generate NADPH before use in reactions. Reactions were sampled at various timepoints, and quenched in four volumes of an acidic quencher consisting of equal parts acetonitrile and 0.25 M HCl.

Products generated from enzymatic inactivation of both tetracycline and chlortetracycline were separated by reverse phase HPLC using a PHENOMENEX LUNA C18 column (5 μm, 110 Å, 2×50 mm) and 0.1% trifluoroacetic acid in water (A) and acetonitrile (B) as mobile phase. Injections of 25 µl sample volume were eluted using a linear gradient from 25% B to 75% B over 14 minutes at a flow rate of 1 ml/min.

Chlortetracycline reactions analyzed by high resolution tandem mass spectrometry were sampled at 75 minutes. The quenched samples were diluted 6× with 50% methanol in 0.1% formic acid and run on the Q-EXACTIVE ORBITRAP by direct infusion using the ADVION TRIVERSA NANOMATE. The data were acquired with resolution of 140,000. The MS scan was acquired from m/z 300-550. MS/MS spectra were acquired on the m/z 467.12 compounds.

Tetracycline Inactivation in E. coli:

Antibiotic susceptibility testing was performed in E. coli MegaX cells (INVITROGEN) bearing the pZE21 expression vector with the tetracycline inactivating gene of interest. Minimum inhibitory concentrations were determined according to Clinical and Laboratory Standards Institute (CLSI) procedures[59] using Mueller-Hinton broth with 50 µg/mL kanamycin and a range of chlortetracycline concentrations profiled via absorbance measurements at 600 nm (OD600) at 45 minute intervals using the SYNERGY H1 microplate reader (Biotek Instruments, Inc) for 48 hours at 37° C.

Kinetic Characterization of Tetracycline and Chlortetracycline Inactivation:

The optimal enzyme concentration for steady-state kinetics assays was determined by varying the concentration of enzyme while keeping chlortetracycline and NADPH concentration constant. 0.4 µM enzyme was found to give linear slopes for all concentrations of substrate tested, and was used as the enzyme concentration for all kinetics experiments.

Reactions were prepared in 100 mM TAPS buffer at pH 8.5 with 0-160 µM substrate, 1.6 mM NADPH, and 0.4 µM enzyme. UV-visible spectroscopy measurements were taken in triplicate at 400 nm wavelength light with a Cary 60 UV/Vis system (AGILENT) for 10 minutes at room temperature. Initial reaction velocities were determined by linear regression using the AGILENT Cary WinUV Software, and fitted to the Michaelis-Menten equation:

$$v_0 = \frac{V_{max}[S]}{K_M + [S]}$$

using GRAPHPAD PRISM 6.

LC-MS Characterization of Chlortetracycline Degradation Products:

Reactions were prepared in 100 mM phosphates buffer at pH 8.5 with 1 mM CTC, 0.5 mM NADPH, 5 mM MgCl$_2$ and 0.4 µM Tet(55). After 10 minutes, the reaction was centrifuge filtered for 10 minutes using a Millipore Amicon Ultracel (3 kDa MW cutoff) to remove enzyme. Prior to centrifugation, filters were triply rinsed with phosphate buffer to remove excess glycerol. The filtrate was collected and analyzed by LC-MS using an AGILENT 6130 single quadrupole instrument with G1313 autosampler, G1315 diode array detector, and 1200 series solvent module. Reaction products were separated using a PHENOMENEX Gemini C18 column, 50×2 mm (5 µm) with guard column cassette was used with a linear gradient of 0% acetonitrile+ 0.1% formic acid to 95% acetonitrile+0.1% formic acid over 14 min at a flow rate of 0.5 mL/min prior to analysis by electrospray ionization.

In Vitro Characterization of Anhydrotetracycline Inhibition:

IC50 values were determined for Tet(50), Tet(55), and Tet(56) by measuring the initial velocity of tetracycline degradation in the presence of varying concentrations of anhydrotetracycline. The concentrations of tetracycline and NADPH were kept constant at 25 µM and 500 µM, respectively. Assays were prepared by combining all components except for enzyme and equilibrating to 25° C. for five minutes. After the addition of enzyme, absorbance at 400 nm was measured for five minutes. All measurements were taken in triplicate. The final concentrations for assay components were 100 mM TAPS buffer (pH 8.5), 25 µM tetracycline, 500 µM NADPH, 16 mM MgCl$_2$, 0.4 µM enzyme, and 0.05-150 µM anhydrotetracycline. A control assay using no anhydrotetracycline was assigned a concentration of $1.0 \times 10^{-15}$ µM for analysis. A second control using no enzyme and 100 µM anhydrotetracycline was assigned a concentration of 1.0×1015 µM to simulate full inhibition of enzyme. IC50 values were determined by plotting the log of anhydrotetracycline concentration against v0 in GRAPHPAD PRISM 6. Functional Tet(51) expressed poorly, so Tet(51) was omitted from these and other in vitro experiments.

Checkerboard Synergy Assay:

Tetracycline (1024 µg/mL) and anhydrotetracycline (256 µg/mL) were dissolved in cation-adjusted Mueller-Hinton broth supplemented with 50 ug/mL kanamycin. A twofold dilution series of each drug was made independently across 8 rows of a 96 well master plate before 100 µL of each drug dilution series were combined into a 96 well culture plate (Costar), with rows included for no-drug and no-inocula controls. A sterile 96-pin replicator (Scinomix) was used to inoculate plates with ~1 µL of E. coli MegaX (INVITROGEN) expressing a tetracycline inactivating enzyme, diluted to OD600 0.1. Plates were sealed with Breathe-Easy membranes (Sigma-Aldrich) and incubated at 37° C. with shaking at 220 rpm. Endpoint growth was determined by OD600 at 20 and 36 hours of growth using a SYNERGY H1 plate reader (BioTek, Inc.). Three independent replicates were performed for each strain on separate days. Synergy of anhydrotetracycline and tetracycline combinations was determined using the fractional inhibitory concentration index (FICI) method,[60]

$$FICI = \frac{MICA_{combo}}{MICA_{alone}} + \frac{MICB_{combo}}{MICB_{alone}}$$

where FICI>1 indicates antagonism, FICI=1 indicates additivity, and FICI <1 indicates synergy. The efficacy of the drug combination was also evaluated in the L. longbeacheae background, but synergy was not observed.

REFERENCES FOR EXAMPLE 1

1 Knapp, C. W., Dolfing, J., Ehlert, P. A. & Graham, D. W. Evidence of increasing antibiotic resistance gene abundances in archived soils since 1940. *Environ Sci Technol* 44, 580-587, doi:10.1021/es901221x (2010).
2 Kinch, M. S., Patridge, E., Plummer, M. & Hoyer, D. An analysis of FDA-approved drugs for infectious disease: antibacterial agents. *Drug Discov Today* 19, 1283-1287, doi:10.1016/j.drudis.2014.07.005 (2014).
3 Davies, J. Inactivation of antibiotics and the dissemination of resistance genes. *Science* 264, 375-382 (1994).

4 Allen, H. K. et al. Call of the wild: antibiotic resistance genes in natural environments. *Nat Rev Microbiol* 8, 251-259, doi:10.1038/nrmicro2312 (2010).

5 Berendonk, T. U. et al. Tackling antibiotic resistance: the environmental framework. *Nat Rev Microbiol* 13, 310-317, doi:10.1038/nrmicro3439 (2015).

6 Benveniste, R. & Davies, J. Aminoglycoside Antibiotic-Inactivating Enzymes in Actinomycetes Similar to Those Present in Clinical Isolates of Antibiotic-Resistant Bacteria. *Proc Natl Acad Sci USA* 70, 2276-2280 (1973).

7 D'Costa, V. M. et al. Antibiotic resistance is ancient. *Nature* 477, 457-461, doi:10.1038/nature10388 (2011).

8 Forsberg, K. J. et al. The shared antibiotic resistome of soil bacteria and human pathogens. *Science* 337, 1107-1111, doi:10.1126/science.1220761 (2012).

9 Forsberg, K. J. et al. Bacterial phylogeny structures soil resistomes across habitats. *Nature* 509, 612-616, doi: 10.1038/nature13377 (2014).

10 Yong, D. et al. Characterization of a new metallo-beta-lactamase gene, bla(NDM-1), and a novel erythromycin esterase gene carried on a unique genetic structure in *Klebsiella pneumoniae* sequence type 14 from India. *Antimicrob Agents Chemother* 53, 5046-5054, doi: 10.1128/aac.00774-09 (2009).

11 Liu, Y. Y. et al. Emergence of plasmid-mediated colistin resistance mechanism MCR-1 in animals and human beings in China: a microbiological and molecular biological study. *Lancet Infect Dis* 16, 161-168, doi:10.1016/s1473-3099(15)00424-7 (2016).

12 Poirel, L., Rodriguez-Martinez, J. M., Mammeri, H., Liard, A. & Nordmann, P. Origin of plasmid-mediated quinolone resistance determinant QnrA. *Antimicrob Agents Chemother* 49, 3523-3525, doi:10.1128/aac.49.8.3523-3525.2005 (2005).

13 Thaker, M., Spanogiannopoulos, P. & Wright, G. D. The tetracycline resistome. *Cell Mol Life Sci* 67, 419-431, doi:10.1007/s00018-009-0172-6 (2010).

14 State of the World's Antibiotics, 2015. (Center for Disease Dynamics, Economics & Policy, Washington, D.C., 2015).

15 Kasbekar, N. Tigecycline: a new glycylcycline antimicrobial agent. *Am J Health Syst Pharm* 63, 1235-1243, doi:10.2146/ajhp050487 (2006).

16 Sutcliffe, J. A., O'Brien, W., Fyfe, C. & Grossman, T. H. Antibacterial activity of eravacycline (TP-434), a novel fluorocycline, against hospital and community pathogens. *Antimicrob Agents Chemother* 57, 5548-5558, doi: 10.1128/AAC.01288-13 (2013).

17 Macone, A. B. et al. In vitro and in vivo antibacterial activities of omadacycline, a novel aminomethylcycline. *Antimicrob Agents Chemother* 58, 1127-1135, doi: 10.1128/aac.01242-13 (2014).

18 Chopra, I. & Roberts, M. Tetracycline antibiotics: mode of action, applications, molecular biology, and epidemiology of bacterial resistance. *Microbiol Mol Biol Rev* 65, 232-260; second page, table of contents, doi:10.1128/mmbr.65.2.232-260.2001 (2001).

19 Park, B. H. & Levy, S. B. The cryptic tetracycline resistance determinant on Tn4400 mediates tetracycline degradation as well as tetracycline efflux. *Antimicrob Agents Chemother* 32, 1797-1800 (1988).

Speer, B. S. & Salyers, A. A. Characterization of a novel tetracycline resistance that functions only in aerobically grown *Escherichia coli*. *J Bacteriol* 170, 1423-1429 (1988).

21 Whittle, G., Hund, B. D., Shoemaker, N. B. & Salyers, A. A. Characterization of the 13-kilobase ermF region of the *Bacteroides* conjugative transposon CTnDOT. *Appl Environ Microbiol* 67, 3488-3495, doi:10.1128/aem.67.8.3488-3495.2001 (2001).

22 Nonaka, L. & Suzuki, S. New Mg2+-dependent oxytetracycline resistance determinant tet 34 in *Vibrio* isolates from marine fish intestinal contents. *Antimicrob Agents Chemother* 46, 1550-1552 (2002).

23 Diaz-Torres, M. L. et al. Novel tetracycline resistance determinant from the oral metagenome. *Antimicrob Agents Chemother* 47, 1430-1432 (2003).

24 Ghosh, S., Sadowsky, M. J., Roberts, M. C., Gralnick, J. A. & LaPara, T. M. *Sphingobacterium* sp. strain PM2-P1-29 harbours a functional tet(X) gene encoding for the degradation of tetracycline. *J Appl Microbiol* 106, 1336-1342, doi:10.1111/j.1365-2672.2008.04101.x (2009).

25 Yang, W. et al. TetX is a flavin-dependent monooxygenase conferring resistance to tetracycline antibiotics. *J Biol Chem* 279, 52346-52352, doi:10.1074/jbc.M409573200 (2004).

26 Moore, I. F., Hughes, D. W. & Wright, G. D. Tigecycline is modified by the flavin-dependent monooxygenase TetX. *Biochemistry* 44, 11829-11835, doi:10.1021/bi0506066 (2005).

27 Volkers, G., Palm, G. J., Weiss, M. S., Wright, G. D. & Hinrichs, W. Structural basis for a new tetracycline resistance mechanism relying on the TetX monooxygenase. *FEBS Lett* 585, 1061-1066, doi:10.1016/j.febslet.2011.03.012 (2011).

28 Forsberg, K. J., Patel, S., Wencewicz, T. A. & Dantas, G. The tetracycline destructases: a novel family of tetracycline inactivating enzymes. *Chemistry and Biology* 22, 888-897 (2015).

29 Drawz, S. M., Papp-Wallace, K. M. & Bonomo, R. A. New beta-lactamase inhibitors: a therapeutic renaissance in an MDR world. *Antimicrob Agents Chemother* 58, 1835-1846, doi:10.1128/aac.00826-13 (2014).

30 Hornak, V., Okur, A., Rizzo, R. C. & Simmerling, C. HIV-1 protease flaps spontaneously close to the correct structure in simulations following manual placement of an inhibitor into the open state. *J Am Chem Soc* 128, 2812-2813, doi:10.1021/ja058211x (2006).

31 Pesnot, T., Jorgensen, R., Palcic, M. M. & Wagner, G. K. Structural and mechanistic basis for a new mode of glycosyltransferase inhibition. *Nat Chem Biol* 6, 321-323, doi:10.1038/nchembio.343 (2010).

32 Cazalet, C. et al. Analysis of the *Legionella longbeachae* genome and transcriptome uncovers unique strategies to cause Legionnaires' disease. *PLoS Genet* 6, e1000851, doi:10.1371/journal.pgen.1000851 (2010).

33 Whiley, H. & Bentham, R. *Legionella longbeachae* and legionellosis. *Emerg Infect Dis* 17, 579-583, doi:10.3201/eid1704.100446 (2011).

34 Ballou, D. P., Entsch, B. & Cole, L. J. Dynamics involved in catalysis by single-component and two-component flavin-dependent aromatic hydroxylases. *Biochem Biophys Res Commun* 338, 590-598, doi:10.1016/j.bbrc.2005.09.081 (2005).

35 van Berkel, W. J., Kamerbeek, N. M. & Fraaije, M. W. Flavoprotein monooxygenases, a diverse class of oxidative biocatalysts. *J Biotechnol* 124, 670-689, doi:10.1016/j.jbiotec.2006.03.044 (2006).

36 Gatti, D. L. et al. The mobile flavin of 4-OH benzoate hydroxylase. *Science* 266, 110-114 (1994).

37 Massey, V. Activation of molecular oxygen by flavins and flavoproteins. *J Biol Chem* 269, 22459-22462 (1994).

38 Volkers, G. et al. Putative dioxygen-binding sites and recognition of tigecycline and minocycline in the tetracycline-degrading monooxygenase TetX. *Acta Crystallogr D Biol Crystallogr* 69, 1758-1767, doi:10.1107/s0907444913013802 (2013).
39 Liu, L. K. et al. The Structure of the Antibiotic Deactivating, N-hydroxylating Rifampicin Monooxygenase. *J Biol Chem* 291, 21553-21562, doi:10.1074/jbc.M116.745315 (2016).
Gibson, M., Nur-e-alam, M., Lipata, F., Oliveira, M. A. & Rohr, J. Characterization of kinetics and products of the Baeyer-Villiger oxygenase MtmOIV, the key enzyme of the biosynthetic pathway toward the natural product anticancer drug mithramycin from *Streptomyces argillaceus*. *J Am Chem Soc* 127, 17594-17595, doi:10.1021/ja055750t (2005).
41 Wang, P., Bashiri, G., Gao, X., Sawaya, M. R. & Tang, Y. Uncovering the enzymes that catalyze the final steps in oxytetracycline biosynthesis. *J Am Chem Soc* 135, 7138-7141, doi:10.1021/ja403516u (2013).
42 Yuen, P. H. & Sokoloski, T. D. Kinetics of concomitant degradation of tetracycline to epitetracycline, anhydrotetracycline, and epianhydrotetracycline in acid phosphate solution. *J Pharm Sci* 66, 1648-1650 (1977).
43 Palmer, A. C., Angelino, E. & Kishony, R. Chemical decay of an antibiotic inverts selection for resistance. *Nat Chem Biol* 6, 105-107, doi:10.1038/nchembio.289 (2010).
44 Liu, F. & Myers, A. G. Development of a platform for the discovery and practical synthesis of new tetracycline antibiotics. *Curr Opin Chem Biol* 32, 48-57, doi:10.1016/j.cbpa.2016.03.011 (2016).
Lienhart, W. D., Gudipati, V. & Macheroux, P. The human flavoproteome. *Arch Biochem Biophys* 535, 150-162, doi:10.1016/j.abb.2013.02.015 (2013).
46 Leski, T. A. et al. Multidrug-resistant tet(X)-containing hospital isolates in Sierra Leone. *Int J Antimicrob Agents* 42, 83-86, doi:10.1016/j.ijantimicag.2013.04.014 (2013).
47 Deng, M. et al. Molecular epidemiology and mechanisms of tigecycline resistance in clinical isolates of *Acinetobacter baumannii* from a Chinese university hospital. *Antimicrob Agents Chemother* 58, 297-303, doi:10.1128/aac.01727-13 (2014).
48 Boucher, H. W. et al. Bad bugs, no drugs: no ESKAPE! An update from the Infectious Diseases Society of America. *Clin Infect Dis* 48, 1-12, doi:10.1086/595011 (2009).
49 Walsh, C. T. & Wencewicz, T. A. Flavoenzymes: versatile catalysts in biosynthetic pathways. *Nat Prod Rep* 30, 175-200, doi:10.1039/c2np20069d (2013).
50 Merriam, J. J., Mathur, R., Maxfield-Boumil, R. & Isberg, R. R. Analysis of the *Legionella pneumophila* fliI gene: intracellular growth of a defined mutant defective for flagellum biosynthesis. *Infect Immun* 65, 2497-2501 (1997).
51 Feeley, J. C. et al. Charcoal-yeast extract agar: primary isolation medium for *Legionella pneumophila*. *J Clin Microbiol* 10, 437-441 (1979).
52 Berger, K. H. & Isberg, R. R. Two distinct defects in intracellular growth complemented by a single genetic locus in *Legionella pneumophila*. *Mol Microbiol* 7, 7-19 (1993).
53 Sexton, J. A. et al. The *Legionella pneumophila* PilT homologue DotB exhibits ATPase activity that is critical for intracellular growth. *J Bacteriol* 186, 1658-1666 (2004).
54 Kabsch, W. XDS. *Acta Crystallogr D Biol Crystallogr* 66, 125-132, doi:10.1107/s0907444909047337 (2010).
55 Winn, M. D. et al. Overview of the CCP4 suite and current developments. *Acta Crystallogr D Biol Crystallogr* 67, 235-242, doi:10.1107/s0907444910045749 (2011).
56 Emsley, P. & Cowtan, K. Coot: model-building tools for molecular graphics. *Acta Crystallogr D Biol Crystallogr* 60, 2126-2132, doi:10.1107/s0907444904019158 (2004).
57 Adams, P. D. et al. PHENIX: a comprehensive Python-based system for macromolecular structure solution. *Acta Crystallogr D Biol Crystallogr* 66, 213-221, doi:10.1107/s0907444909052925 (2010).
58 Chen, V. B. et al. MolProbity: all-atom structure validation for macromolecular crystallography. *Acta Crystallogr D Biol Crystallogr* 66, 12-21, doi:10.1107/s0907444909042073 (2010).
59 CLSI. *Methods for Dilution Antimicrobial Susceptibility Testing for Bacteria That Grow Aerobically; Approved Standard—Tenth Edition*. Vol. M07-A10 (Clinical and Laboratory Standards Institute, 2015).
60 Berenbaum, M. C. A method for testing for synergy with any number of agents. *J Infect Dis* 137, 122-130 (1978).

All cited references are herein expressly incorporated by reference in their entirety.

Example 2: Synthesis of Anhydrotetracycline Analogs

General Methods: All reactions were carried out in oven- or flame-dried glassware under argon atmosphere using standard gas-tight syringes, cannulae, and septa. Stirring was achieved with oven-dried magnetic stir bars. Methanol was purchased from Sigma Aldrich and used without further purification. Chlortetracycline hydrochloride was purchased from Sigma Aldrich, demeclocycline hydrochloride was purchased from Carbosynth, and anhydrotetracycline hydrochloride was purchased from Chemodex, and all were used without further purification (confirmed by LC-MS prior to use). Reactions were monitored by LC-MS, and samples for LC-MS were prepared in 0.45 mM PTFE mini-UniPrep vials from Agilent. All LC-MS was performed on an Agilent 6130 quadrupole LC-MS (in positive ion mode) with G1313 autosampler, G1315 diode array detector (DAD), and 1200 series solvent module. A PHENOMENEX Gemini C18 column, 50 2 mm, 5 mm with guard column was used for all LC-MS separations. LC-MS mobile phases were 0.1% formic acid in (A) water and (B) acetonitrile, and data was processed using G2710 ChemStation software. Optical absorbance chromatograms at 263 nm were collected along with total ion chromatograms (TICs) and extracted ion chromatograms (EICs). LC-MS data was processed using G2710 CHEMSTATION software. All preparatory HPLC was performed using a Beckman Coulter SYSTEM GOLD 127P solvent module and 168 detector with a PHENOMENEX LUNA 10 u C18(2) 100 A column, 250 21.20 mm, 10 mm with guard column. Prep HPLC was performed with a mobile phase of 0.1% formic acid in (A) water and (B) acetonitrile, and data was processed using 32 Karat software, version 7.0. All NMRs were collected on a 300 MHz Varian NMR instrument in fully deuterated dimethylsulfoxide or fully deuterated methanol as solvent.

Synthesis of (4S,4aS,12aS)-7-chloro-4-(dimethylamino)-3,10,11,12a-tetrahydroxy-6-methyl-1,12-dioxo-1,4,4a,5,12,12a-hexahydrotetracene-2-carboxamide hydrochloride (also Abbreviated as anhydrochlortetracycline, aChlortetracycline, A-CTc, or JLM-2-42)

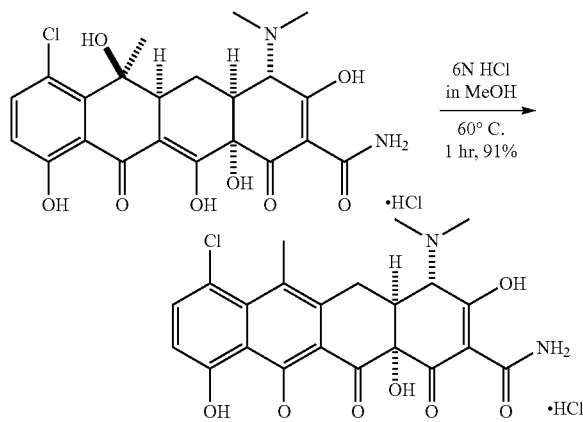

To a clean, dry round bottom flask, equipped with stirbar and reflux condenser, was added chlortetracycline hydrochloride (50 mg, 0.097 mmol) and 6 N HCl in methanol (5 mL) under argon atmosphere. The reaction was heated to 60° C. and allowed to stir at 60° C. for 1.5 hours (monitored by LCMS). When the reaction was complete, the reaction was concentrated under reduced pressure and purified by preparative HPLC (Si—C18 reverse phase column, gradient of $CH_3CN/H_2O$ with 0.1% formic acid, $t_R$=16 minutes) to provide (4S,4aS,12aS)-7-chloro-4-(dimethylamino)-3,10,11,12a-tetrahydroxy-6-methyl-1,12-dioxo-1,4,4a,5,12,12a-hexahydrotetracene-2-carboxamide, which was reconstituted as the hydrochloride salt to provide the title compound as an orange solid (44 mg, 0.089 mmol, 91% yield).

Synthesis of (4S,4aS,12aS)-7-chloro-4-(dimethylamino)-3,10,11,12a-tetrahydroxy-1,12-dioxo-1,4,4a,5,12,12a-hexahydrotetracene-2-carboxamide ydrochloride (also Abbreviated as anhydrodemeclocycline, aDemeclocycline, A-Demeclo, JLM-2-43)

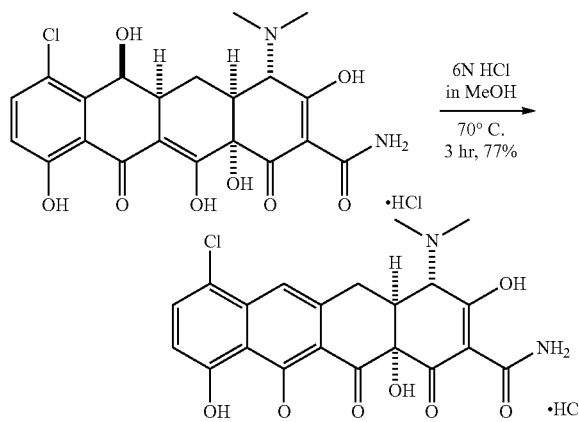

To a clean, dry round bottom flask, equipped with stirbar and reflux condenser, was added demeclocycline hydrochloride (50 mg, 0.10 mmol) and 6 N HCl in methanol (5 mL) under argon atmosphere. The reaction was heated to 70° C. and allowed to stir at 60° C. for 3 hours (monitored by LCMS). When the reaction was complete, the reaction was concentrated under reduced pressure and purified by preparative HPLC (Si—C18 reverse phase column, gradient of $CH_3CN/H_2O$ with 0.1% formic acid, $t_R$=15 minutes) to provide (4S,4aS,12aS)-7-chloro-4-(dimethylamino)-3,10,11,12a-tetrahydroxy-1,12-dioxo-1,4,4a,5,12,12a-hexahydrotetracene-2-carboxamide, which was reconstituted as the hydrochloride salt to provide the title compound as a light orange solid (37 mg, 0.077 mmol, 77% yield).

Synthesis of (4S,4aS,12aS)-4-(dimethylamino)-3,10,11,12a-tetrahydroxy-7-iodo-6-methyl-1,12-dioxo-1,4,4a,5,12,12a-hexahydrotetracene-2-carboxamide hydrochloride (also Abbreviated as 7-iodoanhydrotetracycline, aIodotetracycline, I-ATc, JLM-2-21)

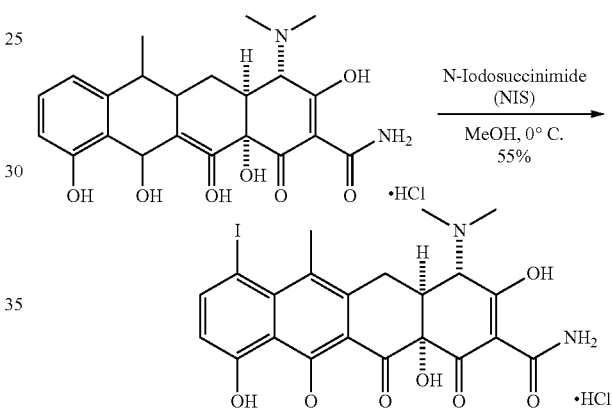

To a clean, dry round bottom flask, equipped with stirbar, was added anhydrotetracycline hydrochloride (100 mg, 0.216 mmol) and methanol (2.2 mL) under argon atmosphere. The flask was cooled to −10° C., and N-iodosuccinimide (58.3 mg, 0.259 mmol) was added in one portion. The reaction was allowed to warm to room 0° C. over 2 hours, then stirred at 00° C. for 1 hour (monitored by LCMS). When the reaction was complete, the reaction was diluted with methanol (to 10 mL total volume) and immediately purified by preparative HPLC (Si—C18 reverse phase column, gradient of $CH_3CN/H_2O$ with 0.1% formic acid, $t_R$=16 min) to provide (4S,4aS,12aS)-4-(dimethylamino)-3,10,11,12a-tetrahydroxy-7-iodo-6-methyl-1,12-dioxo-1,4,4a,5,12,12a-hexahydrotetracene-2-carboxamide, which was reconstituted as the hydrochloride salt to provide the title compound as an orange solid (70.0 mg, 0.119 mmol, 55% yield).

Example 3: Inhibition of Tet55 by Anhydrotetracycline Analogs

Experimental Procedure:

The concentrations of chlortetracycline and NADPH were kept constant at 25 μM and 1 mM, respectively. Assays were prepared by combining all components except for enzyme and equilibrating to 25° C. for five minutes. After the addition of enzyme, absorbance at 400 nm was measured for five minutes. All data points were taken in triplicate. The final concentrations for assay components were 100 mM TAPS buffer (pH 8.5), 25 µM chlortetracycline, 1 mM NADPH, 10 mM $MgCl_2$, 100 nM Tet(55), and 0-64 µM inhibitor. A control assay using no inhibitor was assigned an inhibitor concentration of $1.0 \times 10^{-15}$ µM for analysis. A second control using no enzyme and 25 µM inhibitor was assigned a concentration of $1.0 \times 10^{15}$ µM to simulate full inhibition of enzyme and account for any non-enzymatic substrate degradation. A control assay was also done to account for any inhibitor degradation in the presence of Tet(55) but no chlortetracycline. $IC_{50}$ values were determined by plotting the log of inhibitor concentration against v0 in GRAPHPAD PRISM 7.

Figure 17:
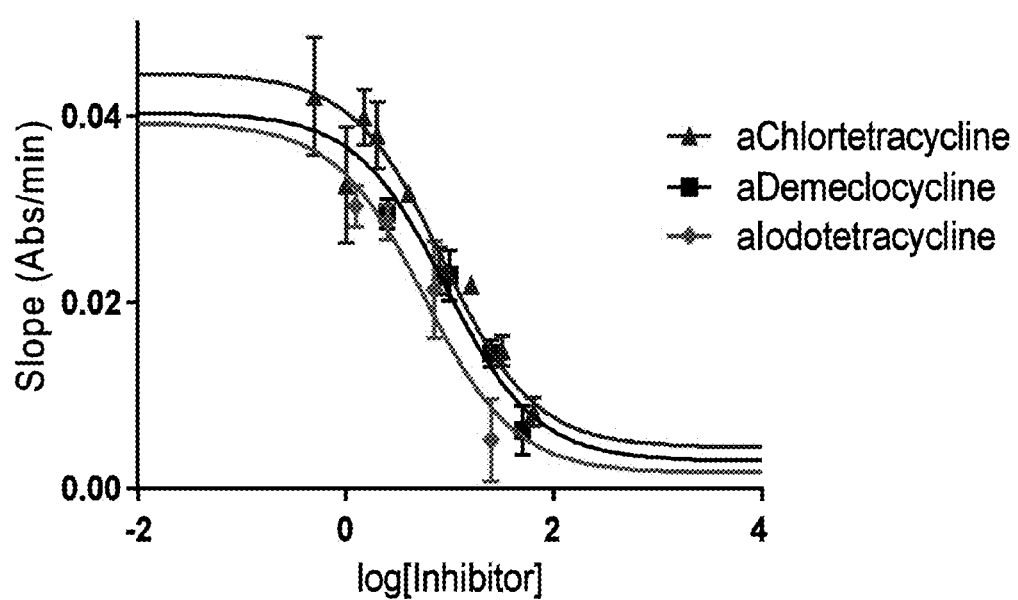
FIG. 17 depicts inhibition of Tet(55) by three anhydrotetracycline variants (i.e., aChlortetracycline, aIodotetracycline, and aDemeclocycine).

$IC_{50}$ values were determined for Tet(55) by measuring the initial velocity of substrate chlortetracycline degradation in the presence of varying concentrations of the inhibitor, either anhydrochlortetracycline (aChlortetracycline), anhydroiodotetracycline (aIodotetracycline), or anhydrodemeclocycline (aDemeclocycine) (FIG. 17). When substrate concentration was kept constant, an increased concentration of inhibitor led to decreased activity of chlortetracycline degradation by Tet(55). Plotting the log of the inhibitor concentration against v0 allows the $IC_{50}$ to be determined, which is defined as the concentration of inhibitor that leads to a 50% decrease of uninhibited enzyme activity. The measured $IC_{50}$ values for anhydrochlortetracycline (aChlortetracycline), anhydroiodotetracycline (aIodotetracycline), and anhydrodemeclocycline (aDemeclocycine) were 9±1 µM, 6±1 µM, and 9±1 µM, respectively.

---

What is claimed is:

1. A method of treating a bacterial infection in a subject, wherein the bacteria encodes a tetracycline destructase selected from the group consisting of Tet (50), Tet (51), Tet (55), Tet (56), and combinations thereof, the method comprising administering to a subject a therapeutically effective amount of a compound that binds to the tetracycline destructase, competitively blocks substrate binding and/or sterically blocks the transition of FAD into the active site, wherein the compound is selected from the group consisting of anhydrotetracycline, aChlortetracycline, aIodotetracycline, aDemeclocyine, and combinations thereof, and administering a therapeutically effective amount of a tetracycline or pharmaceutically acceptable salt thereof.

2. The method of claim 1, wherein the tetracycline is selected from the group consisting of tetracycline, chlorotetracycline, demecocylcine, doxycycline, epi-tetracycline, epi-anhydrotetracycline, lymecycline, meclocycline, metacycline, methacycline, minocycline, oxytetracyline, tigecycline or pharmaceutically acceptable salt thereof.

3. The method of claim 1, wherein the tetracycline is tetracycline.

4. A method of treating a tetracycline resistant bacterial infection in a subject, wherein the bacteria encodes a tetracycline destructase selected from the group consisting of Tet (50), Tet (51), Tet (55), Tet (56), and combinations thereof, the method comprising administering to a subject a therapeutically effective amount of a compound that binds to the tetracycline destructase, competitively blocks substrate binding and/or sterically blocks the transition of FAD into the active site, wherein the compound is selected from the group consisting of anhydrotetracycline, aChlortetracycline, aIodotetracycline, aDemeclocyine, and combinations thereof, and administering a therapeutically effective amount of a tetracycline or pharmaceutically acceptable salt thereof.

5. The method of claim 4, wherein the tetracycline is selected from the group consisting of tetracycline, chlorotetracycline, demecocylcine, doxycycline, epi-tetracycline, epi-anhydrotetracycline, lymecycline, meclocycline, metacycline, methacycline, minocycline, oxytetracyline, tigecycline or pharmaceutically acceptable salt thereof.

6. The method of claim 5, wherein the tetracycline is tetracycline.

* * * * *